United States Patent [19]

Venuti et al.

[11] Patent Number: 4,593,029
[45] Date of Patent: Jun. 3, 1986

[54] NOVEL ω-(N-IMIDAZOLYL)ALKYL ETHERS OF 1,2,3,5-TETRAHYDROIMIDAZO[2,1-B]QUINAZOLIN-2-ONES

[75] Inventors: Michael C. Venuti, San Francisco; John J. Bruno, Redwood City, both of Calif.

[73] Assignee: Syntex (U.S.A.) Inc., Palo Alto, Calif.

[21] Appl. No.: 580,411

[22] Filed: Feb. 15, 1984

[51] Int. Cl.[4] .................. A61K 31/505; C07D 487/04
[52] U.S. Cl. ............................ 514/267; 544/250; 560/266; 560/254; 568/424; 548/342
[58] Field of Search ............... 544/250; 424/251; 514/267

[56] References Cited

U.S. PATENT DOCUMENTS 4,416,895 11/1983 Thorogood ............... 424/273 R
4,490,371 12/1984 Jones et al. ............... 424/248.54

OTHER PUBLICATIONS

K. Honn, et al., Prog. in Clin. and Biol. Res., 89, 295-331 (1982).

Primary Examiner—Donald G. Daus
Assistant Examiner—Diana G. Rivers
Attorney, Agent, or Firm—Grant D. Green; Tom M. Moran; Alan M. Krubiner

[57] ABSTRACT

Novel compound of the formula

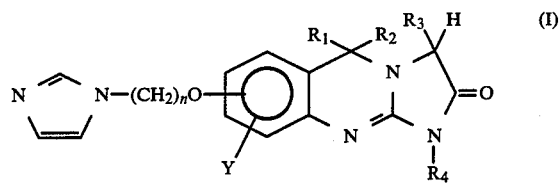

wherein
n is an integer of 1 to 8;
$R_1$ is hydrogen or alkyl of 1-6 carbons;
$R_2$ is hydrogen;
$R_3$ is hydrogen, alkyl of 1-6 carbons, phenyl, benzyl, hydroxy lower alkyl, carbamoyl alkyl, carboxyalkyl, alkoxycarbonylalkyl;
$R_4$ is hydrogen, alkyl of 1-6 carbons, benzyl, or hydroxy lower alkyl;
Y is hydrogen, alkyl of 1 to 4 carbon atoms, halo or lower alkoxy;
any of its optical isomers, the mixture thereof, or the pharmaceutically acceptable acid addition salt.

These compounds are inhibitors of thromboxane synthetase and cyclic AMP phosphodiesterase and are therefore potential cardiovascular agents particularly useful as platelet aggregation inhibitors and anti-thrombotic agents. Accordingly, these compounds will preferably be useful in treating cardiovascular disorders with thrombotic complications. However, they also possess vasodilatory, antisecretory, antihypertensive, inotropic and antimetastatic activities.

147 Claims, No Drawings

NOVEL ω-(N-IMIDAZOLYL)ALKYL ETHERS OF 1,2,3,5-TETRAHYDROIMIDAZO[2,1-B]QUINAZOLIN-2-ONES

BACKGROUND OF THE INVENTION

1. Field of the Invention

This invention relates to novel ω-(N-imidazolyl)alkyl ethers of substituted 1,2,3,5-tetrahydroimidazo[2,1-b]quinazolines which possess thromboxane synthetase and cyclic AMP phosphodiesterase inhibitory activity and are therefore potentially useful as cardiovascular agents. Particularly, these compounds are useful as platelet aggregation inhibitors and anti-thrombotic agents. Accordingly, these compounds will preferably be used in treating cardiovascular disorders with thrombotic complications. However, they also assert vasodilary, antisecretory, antihypertensive, inotropic and antimetastatic activities and could, therefore be used for treatment of hypertension, complication of gastrointestinal track, heart failure and cancer.

More specifically the compounds of interest are ω-(N-imidazolyl)alkyl ethers of unsubstituted or substituted 1,2,3,5-tetrahydroimidazo[2,1-b]quinazolin-2-one and their pharmaceutically acceptable acid addition salts.

2. Related Disclosure

Publication of possible interest herein are: F. Kienzle, et al, *Eur. J. Med.*, 17(6):547–556, 1982, disclosing 1,5-dihydroimidazoquinazolinones as blood platelet aggregation inhibitors; Japanese patent No. 54-163825; and U.S. Pat. Nos. 3,932,407, 3,983,120; and 3,988,340. Dutch patent NL No. 7,512,965 discloses the process of preparing 1,2,3,5-tetrahydroimidazo[2,1-b]quinazolin-2-ones. Great Britain patent GB No. 2,001,638 discloses imidazo quinazolines which have blood platelet aggregation inhibiting activities. E.P. patent application discloses 1,5-dihydro-3-methyl-imidazoquinazolin useful as blood platelet aggregation inhibitors. Research Disclosure RD-183-003 describes 1,5-dihydroimidazo[2,1-b]quinazolin-2-ones preparation.

These references may be primarily relevant for their disclosure of similarly acting compounds, not because the compounds therein are structural analogues to the compounds of the current invention.

SUMMARY OF THE INVENTION

One aspect of this invention relates to a compound of the formula

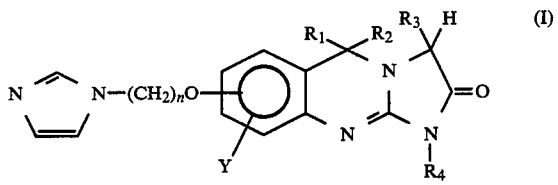

wherein:
  n is an integer of 1 to 8;
  $R_1$ is hydrogen or alkyl of 1–6 carbons;
  $R_2$ is hydrogen;
  $R_3$ is hydrogen, alkyl of 1–6 carbons, phenyl, benzyl, hydroxy lower alkyl, carbamoyl alkyl, carboxyalkyl, alkoxycarbonylalkyl;
  $R_4$ is hydrogen, alkyl of 1–6 carbons, benzyl, or hydroxy lower alkyl;
  Y is hydrogen, alkyl of 1 to 4 carbon atoms, halo or lower alkoxy;
  any of its optical isomers, the mixture thereof, or a pharmaceutically acceptable acid addition salt.

Another aspect of this invention concerns the method of treating cardiovascular disorders with thrombotic complications.

Yet another aspect of this invention relates to a method for inhibiting thromboxane synthetase and 3',5'-cyclic AMP phosphodiesterase activity in a mammal.

In yet another aspect this invention relates to a method of treating heart failure by stimulating suppressed heart activity which occurs during heart failure.

In yet another aspect this invention relates to a method of inhibiting tumor growth.

Still another aspect of this invention relates to a method of treating hypertension.

Still another aspect of this invention relates to a method of treating disorders of the gastro-intestinal tract.

In still another aspect, this invention relates to a pharmaceutically acceptable composition containing a suitable pharmaceutical excipient in admixture with a therapeutically effective amount of a compound of formula I.

DETAILED DESCRIPTION OF THE INVENTION

Definitions

For the purpose of this invention, the following phrases should be understood to have the recited meaning.

"Mammals" means a class of warm-blooded vertebrates characterized by mammary glands, including but not limited to humans, laboratory or domestic animals such as dogs, cats, mice, rats or rabbits, and livestock.

"Treatment" covers any treatment of the disease in a mammal, particularly human, and includes:
  (i) preventing the disease from occurring in a subject which may be predisposed to the disease but has not yet been diagnosed as having it;
  (ii) inhibiting the disease, i.e. arresting the development of said disease; or
  (iii) relieving the disease, i.e. causing regression of the disease.

"Thrombosis" means the formation or presence of a thrombus or clotting within a blood vessel which may cause infarction of tissues supplied by the vessel.

"Coronary thrombosis" means coronary occlusion by thrombus formation. Coronary thrombosis usually appear as a result of atheromatous changes in the arterial wall and usually leads to myocardial infarction.

"Platelet thrombosis" means thrombosis due to an abnormal accumulation of platelets.

"Thrombocytopenia" means a platelet disorder characterized by the abnormally small number of platelets circulating in the blood. Thrombocytopenia has many causes such as failure of production, increased destruction, increased utilization, dilution or disseminated intravascular coagulation-intravascular thrombosis.

"Transient ischemic attack" means focal neurologic abnormalities of sudden onset and brief duration, usually shorter than 24 hours, that reflect dysfunction in the distribution of either the internal carotid-middle cerebral or the vertebral-basilar arterial system. These attacks are usually recurrent and at times presage a stroke. Transient ischemic attacks most often result from atherosclerotic stenosis, thrombosis or embolism.

"Alkyl of 1 to 6 carbon atoms" means a branched or unbranched saturated hydrocarbon chain containing no more than six carbon atoms. The phrase refers specifically to such substituents as, for example, methyl, ethyl, n-propyl, i-propyl, n-butyl, tert-butyl, n-pentyl, n-hexyl and the like.

The terms "lower alkyl" and "alkyl of 1 to 4 carbon atoms" are used interchangeably and mean methyl, ethyl, n-propyl, i-propyl, n-butyl, t-butyl and the like.

"Lower alkoxy" means the group —OR wherein R is lower alkyl is defined in the foregoing paragraph.

"Hydroxyalkyl" means an alkyl of 1 to 6 carbon atoms. Herein the alkyl chain may be straight, preferably, or branched, is fully saturated and, except for the hydroxyl group, has no other substitution. Examples of hydroxyalkyl substituents are 2-hydroxyethyl, 3-hydroxypropyl, 4-hydroxybutyl, 5-hydroxypentyl and 6-hydroxyhexyl. However, the other unnamed hydroxyalkyls are also covered by this definition.

"Halo" means fluorine, chlorine, bromine or iodine.

The phrase "unsubstituted or substituted" is used herein to indicate that the ring may have on it the hydrogen or, alternatively, it may be substituted with one or more of the enumerated radicals as specifically indicated.

The prefix D- and L- are used to describe the individual optical isomers having an asymmetric center at the 3 or 5 position of the 1,2,3,5-tetrahydroimidazo[2,1-b]quinazolin-2-one structure.

"Pharmaceutically acceptable acid addition salt" refers to those salts which retain the biological properties and efficacy of the free bases and which are not biologically or otherwise undesirable, formed with inorganic or organic acids. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The compounds of the present invention are numbered as follows:

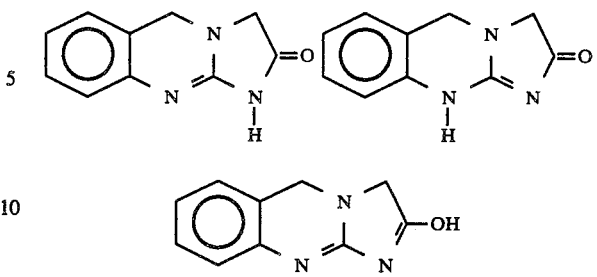

It is to be understood that all tautomers are part of the present invention.

In addition, both imidazolylalkyloxy and Y substituent(s) may be attached at any of one or more of the ring positions such as for example in position 6, 7, 8, or 9, as indicated by formula I. The attachment at position 7 is preferred for imidazolylalkyloxy. The attachment at position 6 is preferred for Y substituents.

Also within the scope of this invention are the optical isomers of those compounds having an asymmetric center, such as when positions 3 and/or 5 of the 1,2,3,5-tetrahydroimidazo[2,1-b]quinazolin-2-one structure are substituted with a substituent other than hydrogen.

Accordingly, the compounds of the present invention may be prepared either in optically active form or as racemic mixtures. Unless otherwise specified, where appropriate, products of the various synthetic steps described herein will be a racemic mixture. However, the scope of the subject invention herein is not limited to the racemic mixture, but is to encompass the separated individual optical isomers of the disclosed compounds.

If desired, the compounds herein may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, methoxyacetic acid, tartaric acid, malic acid, diacetyltartaric acid, pyrrolidine-5-carboxylic acid and the like. The separated pure diasteremeric salts may then be cleaved by standard means to afford the respective optical isomers.

PREFERRED EMBODIMENTS

This invention concerns compound of the formula

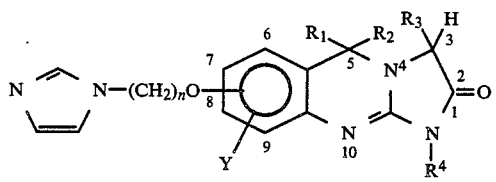

For the purpose of this disclosure, the compounds of the present invention are represented as having the single structure formulation represented by formula I. However, compounds of formula I can exist in several possible tautomeric forms established by the following core structures:

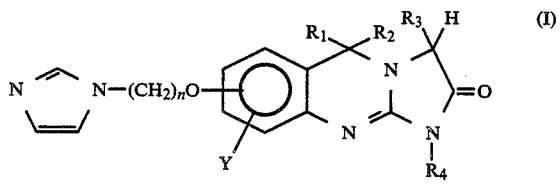

wherein:
n is an integer of 1 to 8;
$R_1$ is hydrogen or alkyl of 1–6 carbons;
$R_2$ is hydrogen;
$R_3$ is hydrogen, alkyl of 1–6 carbons, phenyl, benzyl, hydroxy lower alkyl, carbamoyl alkyl, carboxyalkyl, alkoxycarbonylalkyl;

$R_4$ is hydrogen, alkyl of 1-6 carbons, benzyl, or hydroxy lower alkyl;

Y is hydrogen, alkyl of 1 to 4 carbon atoms, halo or lower alkoxy;

any of its optical isomers, the mixture thereof, or a pharmaceutically acceptable acid addition salt.

Presently preferred embodiments of this invention are the following groups:

One preferred group of compounds of formula I are those wherein Y is hydrogen or chlorine and $R_1$, $R_2$, $R_3$, $R_4$ and n are as indicated above.

Another preferred group of compounds of formula I are those wherein $R_1$, $R_2$ and $R_4$ are hydrogen, and $R_3$ is hydrogen, methyl or hydroxymethyl, Y is hydrogen or chlorine and n is as indicated above.

Still more preferred group of compounds of formula I are those wherein n is an integer of 2-6, $R_1$, $R_2$, $R_3$ and $R_4$ are hydrogen, methyl or hydroxymethyl, and Y is hydrogen or chlorine.

Most preferred group of compounds are those wherein n is 6, and $R_1$, $R_2$, $R_3$, $R_4$ and Y are all hydrogen and imidazolylalkyl is attched at position 7. The representative compound of this group is 7-[6-(N-imidazolyl)hexyl]oxy-1,2,3,5-tetrahydroimidazo[2,1-b]quinazolin-2-one.

PREPARATIONS

Compound of this invention may be prepared by two alternate pathways. The first pathway is illustrated in Reaction Scheme 1, the second pathway is illustrated in Reaction Scheme 2.

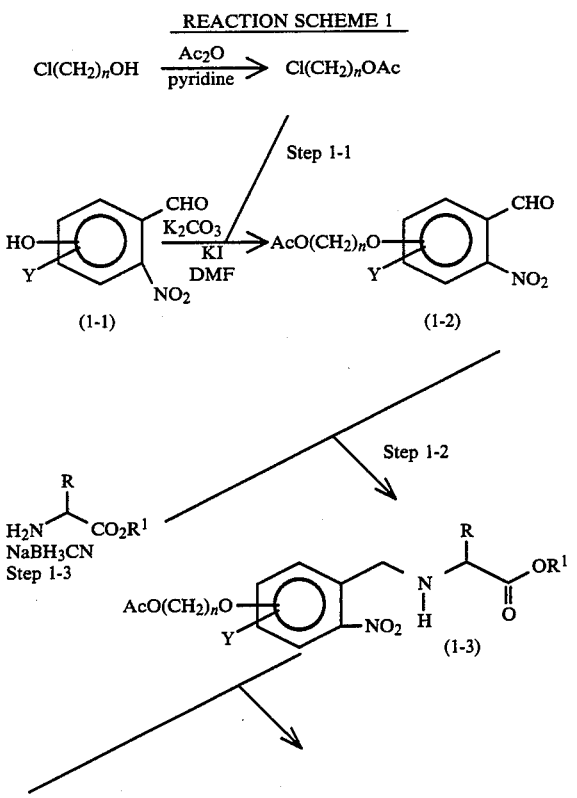

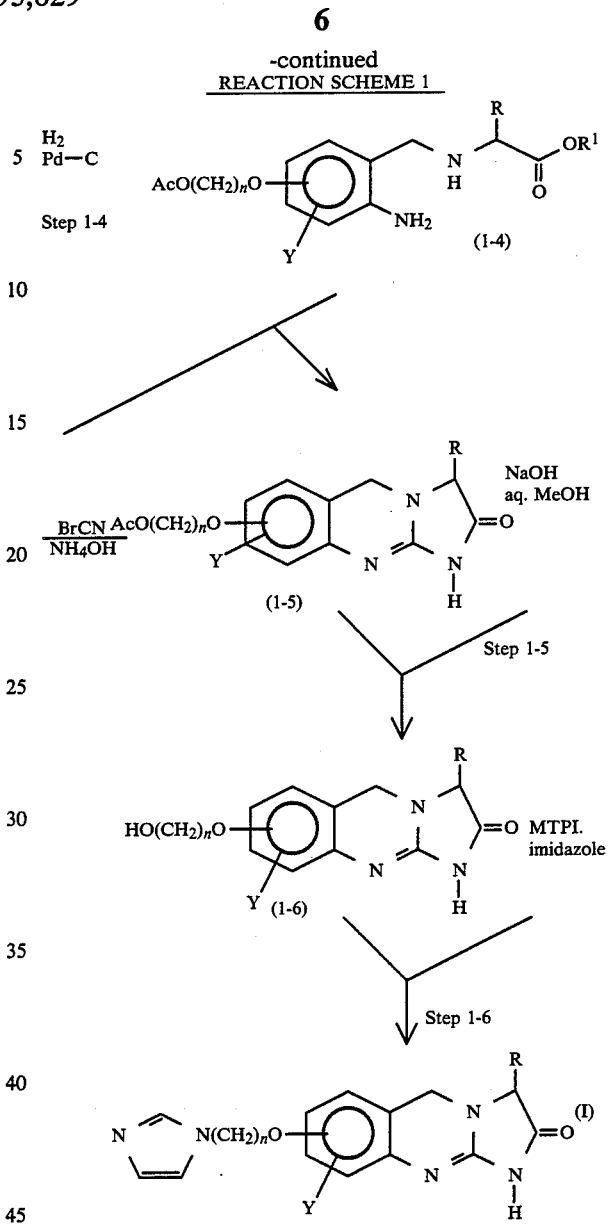

In Reaction Scheme 1 the process for preparing the claimed compounds begins with reacting a source of the n-alkyl chain such as for example 2-chloro-1-ethanol, 3-chloro-1-propanol, 4-chloro-1-butanol, 5-chloro-1-pentanol, 6-chloro-1-hexanol, 7-chloro-1-heptanol, or 8-chloro-1-octanol, preferably 6-chloro-1-hexanol, acid anhydride, tertiary amine, preferably pyridine and organic solvent such as propyl ether, isopropyl ether, butylethyl ether, preferably ethyl ether, in amounts of approximately 100:85:67:300/v:v:v:v, to obtain chloroalkanol acetate.

Step 1-1 Acetoxyalkyl-2-nitrobenzaldehyde (1-2) is prepared by reacting 3, 4, 5 or 6-hydroxy-2-nitrobenzaldehyde (1-1) with chloroalkanol acetate in presence of halogen salt, preferably potassium iodide, base, preferably potassium carbonate, in an organic solvent, preferably in dry DMF, in appropriate amounts of 50:59:5:50:500/w:w:w:w:v.

Step 1-2 7-(acetoxyalkyl)oxy-1,2,3,5-tetrahydroimidazo[2,1-b]quinazolin-2-one (1-5) is prepared by reacting α-amino acid alkyl ester hydrochloride with an acetate, preferably sodium acetate, in a polar organic solvent such as methanol, propanol, butanol, preferably ethanol, with compound (1-2) and cyanoborohydride salt, preferably sodium cyanoborohydride, for approximately 1-15 hours, preferably 4 hours, at the temperature of 10°-35° C., preferably ambient to give compound (1-3).

The α-amino alkyl ester hydrochloride will preferably be a glycine ethyl ester hydrochloride, however, whenever the other $R_3$ substitution is different than hydrogen, the glycine ethyl ester hydrochloride will be substituted with other α-amino alkyl ester hydrochlorides, such as alanine, serine, phenylalanine, phenylglycine, asparagine, aspartic acid, aminobutyric acid, and valine.

Step 1-3 The obtained residue (1-3) is dissolved in a polar organic solvent, preferably ethanol, is submitted to a catalytic hydrogenation with a noble metal catalyst, preferably over 10% Pd-C, for a period of time necessary to a cessation of the uptake of hydrogen, preferably for about 4 hours to give compound (1-4).

Step 1-4 The residue (1-4) is treated with cyanogen bromide and the resulting solution is stirred for 5-25 hours, preferably for 16 hours, followed by treatment with ammonium hydroxide, to give 7-(acetoxyalkyl-)oxy-1,2,3,5-tetrahydroimidazo[2,1-b]quinazolin-2-one (1-5).

Step 1-5 The acetate compound (1-5) dissolved in a polar organic solvent, preferably methanol, is alkalized with a base, preferably sodium hydroxide, dissolved in water in amounts of approximately 14:100:2:20/w:v:w:v to give compound (1-6).

Step 1-6 The alcohol compound (1-6) is converted to a corresponding iodide by reacting said compound (1-6) with phosphonium salt, preferably with methyltriphenoxyphosphonium iodide in an organic solvent, preferably DMF. The reaction mixture is heated to 80°-110° C., preferably 100° C. for 15 minutes to 3 hours, preferably for 30 minutes. The iodide is then added to molten imidazole to provide alkylated imidazole, compound (I).

The procedure outlined in Reaction Scheme 1, can be summarized as follows: An alkyl chlorohydrin is first converted to the ω-chloroacetate, which is used to alkylate the aforementioned hydroxy-2-nitrobenzaldehyde. The nitroaldehyde is then subjected to reductive amination with an α-amino acid ester using sodium cyanoborohydride, to give the nitro amine. Reduction of the nitro moiety, followed by cyclization with a halo cyanogen followed by base, affords the ω-acetoxyalkyloxy heterocycle system. Base-induced hydrolysis, followed by conversion of the resulting alcohol to the corresponding iodide, and alkylation of imidazole in a melt, complete the preparation.

REACTION SCHEME 2

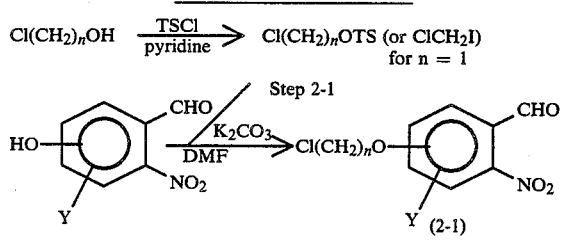

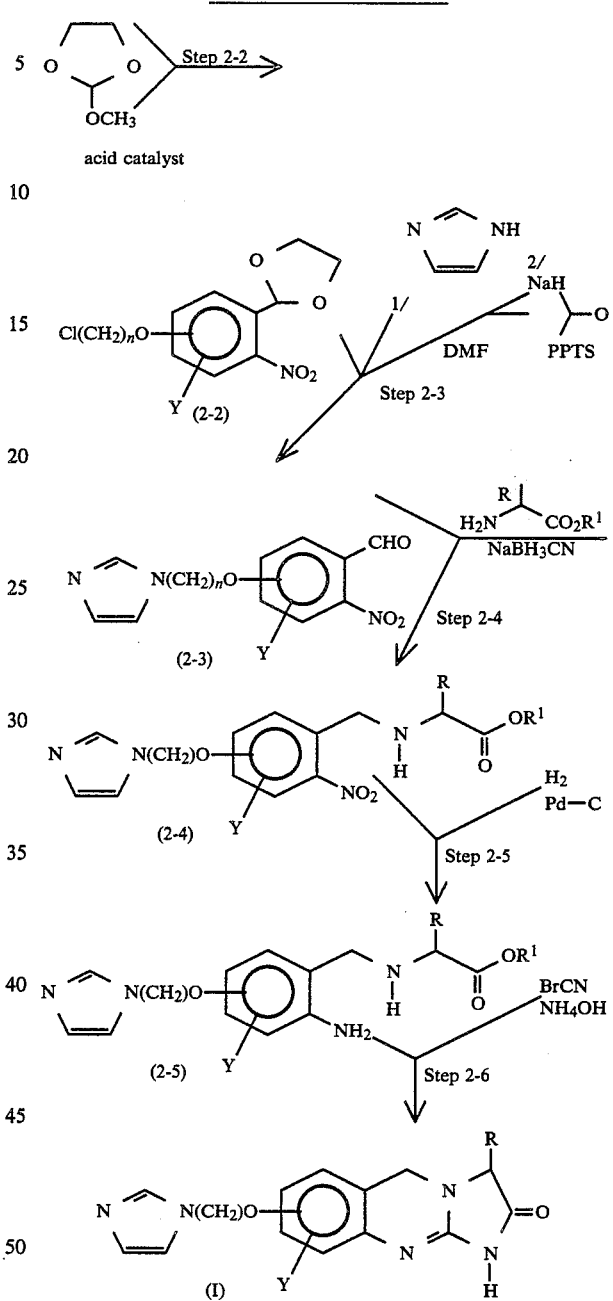

The Reaction Scheme 2 represents an alternate pathway of preparation of compounds of the current invention.

In Reaction Scheme 2, TSCl means toluenesulfonyl chloride and TS means toluenesulfonate and PPTS means pyridinium p-toluenesulfonate.

Chloroalkyl-p-toluenesulfonate, a starting compound for preparation of compound (2-1), is prepared by reacting chloro-1-alkanol in an organic solvent, preferably in dry pyridine and toluenesulfonyl chloride for a time of 1-10 hours, preferably for 2 hours, at a temperature of 2°-15° C., preferably at 10° C.

Step 2-1 Chloroalkyl-p-toluenesulfonate and compound (1-1), described in Reaction Scheme 1, is reacted with a base, preferably potassium carbonate, in an organic solvent, preferably dry DMF, in amounts of approximately 32:17:17:250/w:w:w:v. The reaction mixture is heated to 80°–120° C., preferably to 100° C., for a time of one half hour to 6 hours, preferably 3 hours, in an inert atmosphere to give compound (2-1), 5-(chloroalkyl)oxy-2-nitrobenzaldehyde.

Step 2-2 Chloroacetal compound (2-2) is prepared by reacting the aldehyde (2-1) with dioxolane, preferably with 2-methoxy-1,3-dioxolane, and optically active acid, preferably camphor-10-sulfonic acid, in an organic solvent such as acetone, benzene, ethyl acetate, preferably toluene, in approximate amounts of 26:17:2:100/w:v:w:v, for 8–24 hours, preferably overnight, at the temperature of 60°–100° C., preferably 80° C.

Step 2-3 Chloroacetal compound (2-2) dissolved in an organic solvent, preferably DMF, is added to a chilled solution of imidazole and hydride, preferably sodium hydride, in the same solvent. The mixture is stirred for half an hour to 5 hours, preferably for 1 hour at a temperature of 15°–25° C., preferably ambient. After the solvent evaporation, the residue is dissolved in an organic solvent, preferably acetone, and pyridinium p-toluenesulfonate is added. The mixture is heated at reflux temperature for 8–24 hours, preferably 12 hours, to afford compound (2-3) 5-(N-imidazolylalkyl)oxy-2-nitrobenzaldehyde.

Step 2-4 5-(N-imidazolylalkyl)oxy-1,2,3,5-tetrahydroimidazo[2,1-b]quinazolin-2-one (2-4) is prepared by reacting α-amino acid alkyl ester hydrochloride with an acetate, preferably sodium acetate, in a polar organic solvent such as methanol, propanol, butanol, preferably ethanol, with compound (2-3) and cyanoborohydride salt, preferably sodium cyanoborohydride, for approximately 1–15 hours, preferably 4 hours, at the temperature of 10°–35° C., preferably ambient to give compound (2-4).

α-amino alkyl ester hydrochloride will preferably be a glycine ethyl ester hydrochloride, however, whenever the other $R_3$ substitution is different than hydrogen, the glycine ethyl ester hydrochloride will be substituted with other α-amino alkyl ester hydrochlorides, such as alanine, serine, phenylalanine, phenylglycine, asparagine, aspartic acid, aminobutyric acid, and valine.

Step 2-5 The obtained residue (2-4) is dissolved in a polar organic solvent, preferably ethanol, is submitted to a catalytic hydrogenation with a noble metal catalyst, preferably over 10% Pd-C, for a period of time necessary to a cessation of the uptake of hydrogen, preferably for about 4 hours to give compound (2-5).

Step 2-6 The obtained residue (2-5) is treated with cyanogen bromide and the resulting solution is stirred for 5–25 hours, preferably for 16 hours, followed by treatment with ammonium hydroxide, to give 7-(N-imidazolylalkyl)oxy-1,2,3,5-tetrahydroimidazo[2,1-b]quinazolin-2-one (I).

The procedure outlined in Reaction Scheme 2, can be summarized as follows: Alkyl chlorohydrin is converted to the corresponding tosylate, which is used to alkylate the hydroxy-2-nitrobenzaldehydes. The ω-chloroalkoxy nitroaldehyde is converted to the corresponding acetal, which is then used to alkylate the sodium salt of imidazole. Deprotection of the aldehyde moiety, followed by ring construction as illustrated in Scheme 1, gives compound I.

In the special case of n=1, the chlorotosylate of Scheme 2 is replaced by chloroiodomethane.

The compounds of formula I in free base form may be converted to the bis acid addition salts of compound I by treating the base with two portions of a stoichiometric excess of the appropriate organic or inorganic acid, for example 1 mol of compound of formula I will be treated with at least 2 moles of appropriate acid. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of formula I may be interchanged by taking advantage of differential solubilities of the salts, volatilities or acidities of the acids, or by treating with the appropriately loaded ion exchange resin. For example, the interchange is effected by the reaction of a salt of the compounds of formula I with a slight stoichiometric excess of an acid of a lower pKa than the acid component of the starting salt. This conversion is carried out at a temperature between about 0° C. and the boiling point of the solvent being used as the medium for the procedure.

UTILITY AND ADMINISTRATION

Utility

This invention concerns novel compounds which are potent inhibitors of thromboxane synthetase and human platelet cyclic AMP phosphodiesterase activity. As a consequence, these compounds inhibit the ADP-induced aggregation of human platelets.

Cyclic AMP is known to regulate the activity of numerous enzymes and mediates the action of several hormones. Studies have demonstrated that a deficiency in cyclic AMP or an increase in the activity of a high affinity cyclic AMP phosphodiesterase is associated with a variety of disease states. Inhibitors of 3',5'-cyclic AMP phosphodiesterase are known to be useful in the treatment or prevention of hypertension, asthma, diabetes, obesity, immune disfunctions, psoriasis, inflammation, cardiovascular disease, tumor metastasis, cancer and hyperthyroidism. A full and more complete description of the various prophylactic and therapeutic activities of cyclic AMP phosphodiesterase inhibiting compounds can be found in the following several references: Amer, S. M., "Cyclic Nucleotides As Targets For Drug Design," *Advances in Drug Research*, Vol. 12, 1977, Acedamic Press, London, pp 1–38; Weinryh, I. et al, *J. Pharm. Sci.*, pp 1556–1567, (1972); Amer. S. M. & W. E. Kreighbaum, *J. Pharm. Sci.*, V 64, pp 1–37, (1975); and Harris, D. N., et al, *Enzyme Inhibitors As Drugs*, McMillan & Co., Ed-M. Sandler, pp 127–146, (1980).

Compounds of this invention are useful in the prevention or treatment of a variety of conditions related to platelet aggregation and thrombosis, particularly in treatment of cardiovascular disorders with thrombotic complications such as:

intravascular thrombosis;

coronary thrombosis,
transient ischemic attacks;
platelet thrombosis;
thrombosis;
thrombocytopenia;
platelet activation associated with the use of prosthethic devices such as for example artificial heart valves, etc.

The compounds of the present invention also have inotropic activity. They can strengthen myocardial contraction force by which the heart ventricles can pump the blood into the periphery. Consequently, these compounds also are useful in treating myocardial failure.

The compounds of the current invention are a vasodilatory, and thus show antihypertensive activities and would therefore be useful for treatment of hypertension.

Moreover, these compounds show anti-metastatic activity and would be useful in the treatment of cancer.

Administration

Administration of the active compounds and salts described herein can be via any of the accepted modes of administration for cardiovascular system regulating agents. These methods include oral, parenteral or otherwise systemic routes of administration such as intravenous, subcutaneous, intradermal, intramuscular or in the form of suppository.

The amount of active ingredient administered will, of course, be dependent on the subject being treated, on the severity of the affliction, on the manner of administration and on the judgment of the prescribing physician. However, an effective dosage is in the range of 0.001-15 mg/kg/day, preferably 0.01-3 mg/kg/day. For an average 70 kg human, this would amount to 0.07-1000 mg/day, preferably 0.7-210 mg/day.

For oral administration, which is preferred, a pharmaceutical composition takes the form of solutions, suspensions, tablets, pills, capsules, powders, sustained release formulations and the like.

Parenteral route of administration is the administration of drugs to a patient by injection under or through one or more layers of the skin or mucous membrane. Parenteral administration would preferably be reserved for crisis situations, wherein the subject is unable to swallow or administer the medication to himself.

A more recently devised approach for parenteral administration employs the implantation of a slow-release or sustained-release system, such that a constant level of dosage is maintained. See, e.g., U.S. Pat. No. 3,710,795 and 3,773,919.

Systemic administration via suppository is the administration of the drug in a solid but readily meltable cone or cylinder made of suitable pharmaceutical excipient. Suppositories must be suitable for insertion into a bodily passage or cavity, and are usually inserted into the rectum. This way of administration would be preferred in the patient with severe ingestion disturbance such as repeated vomiting usually occurring in cases of poisoning.

Pharmaceutical Composition

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient, a compound of this invention or the pharmaceutically acceptable salts as an active ingredient thereof. In addition, it may include other medicinal or pharmaceutical agents, carriers, adjuvants, etc.

A pharmaceutical composition may contain 0.1%-95% active ingredient, preferably 1%-70%. In any event, the composition or formulation to be administered will contain a quantity of the active ingredient(s) in an amount effective to alleviate the symptoms of the subject being treated.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. The active ingredient as defined above may be formulated as suppositories using as the carrier, for example, polyalkylene glycols, such as propylene glycol.

Liquid pharmaceutically administerable compositions can be prepared by dissolving or dispersing, or otherwise preparing an active ingredient (as defined above), and mixing it optionally with a pharmaceutical adjuvant in a carrier, such as, for example, water, saline, aqueous dextrose, glycerol, ethanol, and the like, to thereby form a solution or suspension.

For parenteral administration, such as, for example, intravenous injections, the compound is dissolved in a vehicle. Vehicle may be, for example, aqueous vehicle, such as sodium chloride injection, Ringer's injection, dextrose injection and others, water miscible vehicle, such as ethyl alcohol, polyethylene glycol of the liquid series or propylene glycol, or nonaqueous vehicles such a corn oil, peanut oil or sesame oil. Vehicle will be buffered to the proper pH in order to stabilize a solution against chemical degradation and formed in such a way as to control isotonicity of injection. Other substances may also be added as antimicrobial or antioxidant agents.

For systemic administration via suppository, traditional binders and carriers include, e.g. polyalkylene glycols or triglycerides. Such suppositories may be formed from mixtures containing active ingredient in the range of 0.5%-10%; preferably 1-2%.

If desired, the pharmaceutical composition to be administered may also contain minor amounts of nontoxic auxiliary substances such as wetting or emulsifying agents, pH buffering agents and the like, such as for example, sodium acetate, sorbitan monolaurate, triethanolamine sodium acetate, sorbitan monolaurate, triethanolamine oleate, etc.

Methods of preparing various pharmaceutical compositions with a certain amount of active ingredient are known, or will be apparent, to those skilled in this art. For examples, see *Remington's Pharmaceutical Sciences,* Mack Publishing Company, Easton, Pa., 15th Edition (1975).

EXAMPLES

The following examples serve to illustrate the invention. They should not be construed as narrowing or limiting its scope.

EXAMPLE 1

Preparation of Chloroalkanol Acetates

This example illustrates preparation of various chloroalkanol acetates. Alkanol has a chain of 2-8 carbon atoms.

I. Preparation of 6-Chlorohexanol Acetate

A solution of 100 ml of 6-chloro-1-hexanol, 85 ml of acetic anhydride and 67 ml of pyridine in 300 ml of dry ethyl ether was stirred at room temperature for 1 h. The reaction mixture was washed 3 times with 100 ml of water and twice with 100 ml of saturated brine, dried over $Na_2SO_4$, filtered and evaporated. Distillation afforded 133 g of 6-chlorohexanol acetate (99%), b.p. 132° C. (10 mm).

Preparation of Other Chloroalkanol Acetates

Similarly, using the above procedure but substituting 6-chloro-1-hexanol with:
2-chloro-1-ethanol;
3-chloro-1-propanol;
4-chloro-1-butanol;
5-chloro-1-pentanol;
7-chloro-1-heptanol; or
8-chloro-1-octanol; one can obtain respectively:
2-chloro-1-ethanol acetate;
3-chloro-1-propanol acetate;
4-chloro-1-butanol acetate;
5-chloro-1-pentanol acetate;
7-chloro-1-heptanol acetate; or
8-chloro-1-octanol acetate.

EXAMPLE 2

Preparation of 5-(X-Acetoxyalkyl)Oxy-2-Nitrobenzaldehydes

This example illustrates preparation of 5-(X-acetoxyalkyl)oxy-2-nitrobenzaldehydes wherein X is an integer of 2-8 and depends on the length of the alkyl which has the 2-8 carbon atoms chain.

I. Preparation of 5-(6-Acetoxyhexyl)Oxy-2-Nitrobenzaldehyde a. A mixture of 50 g (300 mmol) of 5-hydroxy-2-nitrobenzaldehyde, 59 g (330 mmol) 6-chlorohexanol acetate, 5 g of potassium iodide, and 50 g of potassium carbonate in 500 ml of dry DMF was heated to 100° C. under dry nitrogen for 3 h. The reaction was cooled, filtered and evaporated to a dark oil. The crude product was dissolved in 500 ml of ethyl acetate, and the organic layer was washed twice with 300 ml of saturated sodium carbonate, and twice with 300 ml of brine, dried filtered and evaporated. Distillation (180° C., 0.2 mm) gave a yellow oil which solidified on cooling, to yield 81.5 g (263 mmol, 88%) of 5-(6-acetoxyhexyl)oxy-2-nitrobenzaldehyde, m.p. 42°-43° C.

b. Compounds which are attached to the ring in another than 7 position, can be prepared by substituting 5-hydroxy-2-nitrobenzaldehyde with 6-hydroxy-2-nitrobenzaldehyde for compounds attached at position 6, with 4-hydroxy-2-nitrobenzaldehyde for compounds attached at position 8, with 3-hydroxy-2-nitrobenzaldehyde for compounds attached at position 9. It is to be understood that although all following examples are illustrative of preparation of compounds attached at the position 7, all other compounds attached at positions 6, 8, or 9 may be similarly prepared by substituting 5-hydroxy-2-nitrobenzaldehyde with other hydroxy-2-nitrobenzaldehydes which are commercially available.

II. Preparation of Other Acetoxyalkyl Nitrobenzaldehydes

Similarly, using the above procedure but substituting 5-(6-acetoxyhexyl)oxy-2-nitrobenzaldehyde, 5-(6-acetoxyhexyl)oxy-6-chloro-2-nitrobenzaldehyde, or 5-(6-acetoxyhexyl)oxy-6-methoxy-2-nitrobenzaldehyde with compounds obtained in Example 1, Section II, one obtains, resepectively:
5-(2-acetoxyethyl)oxy-2-nitrobenzaldehyde;
5-(3-acetoxypropyl)oxy-2-nitrobenzaldehyde;
5-(4-acetoxybutyl)oxy-2-nitrobenzaldehyde;
5-(5-acetoxypentyl)oxy-2-nitrobenzaldehyde;
5-(7-acetoxyheptyl)oxy-2-nitrobenzaldehyde; or
5-(8-acetoxyoctyl)oxy-2-nitrobenzaldehyde;
5-(2-acetoxyethyl)oxy-6-chloro-2-nitrobenzaldehyde;
5-(3-acetoxypropyl)oxy-6-chloro-2-nitrobenzaldehyde;
5-(4-acetoxybutyl)oxy-6-chloro-2-nitrobenzaldehyde;
5-(5-acetoxypentyl)oxy-6-chloro-2-nitrobenzaldehyde;
5-(7-acetoxyheptyl)oxy-6-chloro-2-nitrobenzaldehyde;
5-(8-acetoxyoctyl)oxy-6-chloro-2-nitrobenzaldehyde;
5-(2-acetoxyethyl)oxy-6-methoxy-2-nitrobenzaldehyde;
5-(3-acetoxypropyl)oxy-6-methoxy-2-nitrobenzaldehyde;
5-(4-acetoxybutyl)oxy-6-methoxy-2-nitrobenzaldehyde;
5-(5-acetoxypentyl)oxy-6-methoxy-2-nitrobenzaldehyde;
5-(7-acetoxyheptyl)oxy-6-methoxy-2-nitrobenzaldehyde; or
5-(8-acetoxyoctyl)oxy-6-methoxy-2-nitrobenzaldehyde.

EXAMPLE 3

Preparation of 7-(X-Acetoxyalkyl)Oxy-$R_3$-1,2,3,5-Tetrahydroimidazo[2,1-b]Quinazolin-2-ones This example illustrates preparation of various 7-(X-acetoxyalkyl)oxy-$R_3$-1,2,3,5-tetrahydroimidazo[2,1-b]quinazolin-2-ones wherein alkyl has 2-8 carbon atoms chain and $R_3$ is as indicated in Summary.

I. Preparation of 7-(6-Acetoxyhexyl)Oxy-1,2,3,5-Tetrahydroimidazo[2,1-b]quinazolin-2-one This section illustrates the preparation of the title compound wherein $R_3$ is hydrogen.

65.6 g (800 mmol) of sodium acetate was added to warm solution of 139 g (1 mole) glycine ethyl ester hydrochloride in 500 ml of absolute ethanol. Upon cooling, the resulting precipitate of sodium chloride was removed, and to the supernatant was added 30.9 g (100 mmol) of 5-(6-acetoxyhexyl)oxy-2-nitrobenzaldehyde (Example 2.I) and 50 g of molecular sieves. After 30 min., 3.8 g (60 mmol) of sodium cyanoborohydride was added, and the mixture was allowed to stir at room temperature for 3-4 h. The reaction solution was then filtered to remove precipitated solids and molecular sieves, and the methanol was removed by evaporation. The residue was dissolved in 300 ml of ethyl acetate and washed twice with 100 ml of saturated sodium bicarbonate and twice with 100 ml of brine. The organic extract was dried, filtered and evaporated to give a thick syrup. Owing to the instability of the oil, the crude product was used directly in the next reaction.

The thick syrupy residue from above was dissolved in 200 ml of absolute ethanol and hydrogenated over 5 g of 10% Pd-C until uptake of hydrogen ceased for approximately 4 h. The catalyst was removed by filtration through a pad of Celite, and pad was washed clean with 50 ml of absolute ethanol.

The combined filtrates from the previous paragraph were treated with 11.7 (110 mmol) of cyanogen bromide, and the resulting solution was stirred at room temperature for 16 h, then treated with 50 ml of ammonium hydroxide and stirred for 2h. at room temperature. The product precipitated from this mixture as an off-white to tan powder. The powder was further purified by filtration and a water wash and dried, yielding the title compound 7-(6-acetoxyhexyl)oxy-1,2,3,5-tetrahydroimidazo[2,1-b]quinazolin-2-one (15.8 g, 45.7 mmol, 48%), m.p. 192°–193° C.

II. a. Preparation of Other 7-(6-Acetoxyhexyl)oxy-R$_3$ 1,2,3,5-Tetrahydroimidazo[2,1-b]Quinazolin-2-one This section illustrates the preparation of compounds wherein R$_3$ is amino acid side chain. Thus, in this preparation, glycine ethyl ester hydrochloride is substituted with other α-amino acid alkyl ester hydrochloride, and such substitution determines R$_3$ of the final product. The non-exclusive examples of such α-amino acids substituting glycine are alanine, serine, phenylalanine, asparagine, aspartic acid, aminobutyric acid, and valine but others may also be used.

Also, the use of optically active α-amino acid will result in optically active R$_3$ amino acid residue in the final product and thus will ultimately determine the optical activity of the final compound.

By substituting glycine ethyl ester hydrochloride with alanine, serine, phenylalanine, phenylglycine, asparagine, aspartic acid, aminobutyric acid, valine and other amino acid ethyl ester hydrochlorides, one obtains respectively:

7-(6-acetoxyhexyl)oxy-3-methyl-1,2,3,5-tetrahydroimidazo[2,1-b]quinazolin-2-one;
7-(6-acetoxyhexyl)oxy-3-hydroxymethyl-1,2,3,5-tetrahydroimidazo[2,1-b]quinazolin-2-one;
7-(6-acetoxyhexyl)oxy-3-benzyl-1,2,3,5-tetrahydroimidazo[2,1-b]quinazolin-2-one;
7-(6-acetoxyhexyl)oxy-3-phenyl-1,2,3,5-tetrahydroimidazo[2,1-b]quinazolin-2-one;
7-(6-acetoxyhexyl)oxy-3-carbamoylmethyl-1,2,3,5-tetrahydroimidazo[2,1-b]quinazolin-2-one;
7-(6-acetoxyhexyl)oxy-3-carboxylmethyl-1,2,3,5-tetrahydroimidazo[2,1-b]quinazolin-2-one;
7-(6-acetoxyhexyl)oxy-3-ethyl-1,2,3,5-tetrahydroimidazo[2,1-b]quinazolin-2-one;
7-(6-acetoxyhexyl)oxy-3-isopropyl-1,2,3,5-tetrahydroimidazo[2,1-b]quinazolin-2-one;
7-(6-acetoxyhexyl)oxy-6-chloro-3-methyl-1,2,3,5-tetrahydroimidazo[2,1-b]quinazolin-2-one;
7-(6-acetoxyhexyl)oxy-6-chloro-3-hydroxymethyl-1,2,3,5-tetrahydroimidazo[2,1-b]quinazolin-2-one;
7-(6-acetoxyhexyl)oxy-6-chloro-3-benzyl-1,2,3,5-tetrahydroimidazo[2,1-b]quinazolin-2-one;
7-(6-acetoxyhexyl)oxy-6-chloro-3-phenyl-1,2,3,5-tetrahydroimidazo[2,1-b]quinazolin-2one;
7-(6-acetoxyhexyl)oxy-6-chloro-3-carbamoylmethyl-1,2,3,5-tetrahydroimidazo[2,1-b]quinazolin-2-one;
7-(6-acetoxyhexyl)oxy-6-chloro-3-carboxylmethyl-1,2,3,5-tetrahydroimidazo[2,1-b]quinazolin-2-one;
7-(6-acetoxyhexyl)oxy-6-chloro-3-ethyl-1,2,3,5-tetrahydroimidazo[2,1-b]quinazolin-2-one;
7-(6-acetoxyhexyl)oxy-6-chloro-3-isopropyl-1,2,3,5-tetrahydroimidazo[2,1-b]quinazolin-2-one;
7-(6-acetoxyhexyl)oxy-6-methoxy-3-methyl-1,2,3,5-tetrahydroimidazo[2,1-b]quinazolin-2-one;
7-(6-acetoxyhexyl)oxy-6-methoxy-3-hydroxymethyl-1,2,3,5-tetrahydroimidazo[2,1-b]quinazolin-2-one;
7-(6-acetoxyhexyl)oxy-6-methoxy-3-benzyl-1,2,3,5-tetrahydroimidazo[2,1-b]quinazolin-2-one;
7-(6-acetoxyhexyl)oxy-6-methoxy-3phenyl-1,2,3,5- tetrahydroimidazo[2,1-b]quinazolin-2-one;
7-(6-acetoxyhexyl)oxy-6-methoxy-3-carbamoylmethyl-1,2,3,5-tetrahydroimidazo[2,1-b]quinazolin-2-one;
7-(6-acetoxyhexyl)oxy-6-methoxy-3-carboxylmethyl-1,2,3,5-tetrahydroimidazo[2,1-b]quinazolin-2-one;
7-(6-acetoxyhexyl)oxy-6-methoxy-3-ethyl-1,2,3,5-tetrahydroimidazo[2,1-b]quinazolin-2-one;
7-(6-acetoxyhexyl)oxy-6-methoxy-3-isopropyl-1,2,3,5-tetrahydroimidazo[2,1-b]quinazolin-2-one;
7-(6-acetoxyhexyl)oxy-3-L-methyl-1,2,3,5-tetrahydroimidazo[2,1-b]quinazolin-2-one;
7-(6-acetoxyhexyl)oxy-3-L-hydroxymethyl-1,2,3,5-tetrahydroimidazo[2,1-b]quinazolin-2-one;
7-(6-acetoxyhexyl)oxy-3-L-benzyl-1,2,3,5-tetrahydroimidazo[2,1 -b]quinazolin-2-one;
7-(6-acetoxyhexyl)oxy-3-L-phenyl-1,2,3,5-tetrahydroimidazo[2,1-b]quinazolin-2-one;
7-(6-acetoxyhexyl)oxy-3-L-carbamoylmethyl-1,2,3,5-tetrahydroimidazo[2,1-b]quinazolin-2-one;
7-(6-acetoxyhexyl)oxy-3-L-carboxylemethyl-1,2,3,5-tetrahydroimidazo[2,1-b]quinazolin-2-one;
7-(6-acetoxyhexyl)oxy-3-L-ethyl1,2,3,5-tetrahydroimidazo[2,1-b]quinazolin-2-one;
7-(6-acetoxyhexyl)oxy-3-L-isopropyl-1,2,3,5-tetrahydroimidazo[2,1-b]quinazolin-2-one; or
7-(6-acetoxyhexyl)oxy-3-D-methyl-1,2,3,5-tetrahydroimidazo[2,1-b]quinazoline-2-one;
7-(6-acetoxyhexyl)oxy-3-D-hydroxymethyl-1,2,3,5-tetrahydroimidazo[2,1-b]quinazolin-2one;
7-(6-acetoxyhexyl)oxy-3-D-benzyl-1,2,3,5-tetrahydroimidazo[2,1-b]quinazolin-2-one;
7-(6-acetoxyhexyl)oxy-3-D-phenyl-1,2,3,5-tetrahydroimidazo[2,1-b]quinazolin-2-one;
7-(6-acetoxyhexyl)oxy-3-D-carbamoylmethyl-1,2,3,5-tetrahydroimidazo[2,1-b]quinazolin-2-one;
7-(6-acetoxyhexyl)oxy-3-D-carboxylmethyl-1,2,3,5-tetrahydroimidazo[2,1-b]quinazolin-2-one;
7-(6-acetoxyhexyl)oxy-3-D-ethyl-1,2,3,5-tetrahydroimidazo[2,1-b]quinazolin-2-one;
7-(6-acetoxyhexyl)oxy-3-D-isopropyl-1,2,3,5-tetrahydroimidazo[2,1-b]quinazolin-2-one;

II. b. Preparation of Other 7-(X-Acetoxyalkyl)oxy-1,2,3,5-tetrahydroimidazo[2,1-b]quinazolin-2-one The other 7-(X-acetoxyalkyl)oxy-1,2,3,5-tetrahydroimidazo[2,1-b]quinazolin-2-ones wherein R$_3$ is hydrogen can be prepared by substituting 5-(6-acetoxyhexyl)oxy-2-nitrobenzaldehyde with compounds of Example 2. II. to give:

7-(2-acetoxyethyl)oxy-1,2,3,5-tetrahydroimidazo[2,1-b]quinazolin-2-one;
7-(3-acetoxypropyl)oxy-1,2,3,5-tetrahydroimidazo[2,1-b]quinazolin-2-one;
7-(4-acetoxybutyl)oxy-1,2,3,5-tetrahydroimidazo[2,1-b]quinazolin-2-one;
7-(5-acetoxypentyl)oxy-1,2,3,5-tetrahydroimidazo[2,1-b]quinazolin-2-one;
7-(7-acetoxyheptyl)oxy-1,2,3,5-tetrahydroimidazo[2,1-b]quinazolin-2-one; and 7-(8-acetoxyoctyl)oxy-1,2,3,5-tetrahydroimidazo[2,1-b]quinazolin-2-one.

II. c. Preparation of Other 7-(6-Acetoxyalkyl)oxy-$R_3$ 1,2,3,5-tetrahydroimidazo[2,1-b]quinazolin-2-ones Similarly to the procedure of Section II.a., by substituting 5-(6-acetoxyhexyl)oxy-2-nitrobenzaldehyde with any compound obtained in Example 2, Section II., one can obtain 7-(X-acetoxyalkyl)oxy-$R_3$-substituted-1,2,3,5-tetrahydroimidazo[2,1-b]-quinazolin-2-ones wherein x is an integer of 2-8 and depends on the length of alkyl chain $R_3$ is as designated in Summary. In this way one can obtain, respectively:

7-(2-acetoxyethyl)oxy-3-methyl-1,2,3,5-tetrahydroimidazo[2,1-b]quinazolin-2-one;
7-(2-acetoxyethyl)oxy-3-hydroxymethyl-1,2,3,5-tetrahydroimidazo[2,1-b]quinazolin-2-one;
7-(2-acetoxyethyl)oxy-3-benzyl-1,2,3,5-tetrahydroimidazo[2,1-b]quinazolin-2-one;
7-(2-acetoxyethyl)oxy-3-phenyl-1,2,3,5-tetrahydroimidazo[2,1-b]quinazolin-2-one;
7-(2-acetoxyethyl)oxy-3-carbamoylmethyl-1,2,3,5-tetrahydroimidazo[2,1-b]quinazolin-2-one;
7-(2-acetoxyethyl)oxy-3-carboxymethyl-1,2,3,5-tetrahydroimidazo[2,1-b]quinazolin-2-one;
7-(2-acetoxyethyl)oxy-3-ethyl-1,2,3,5-tetrahydroimidazo[2,1-b]quinazolin-2-one;
7-(2-acetoxyethyl)oxy-3-isopropyl-1,2,3,5-tetrahydroimidazo[2,1-b]quinazolin-2-one;
7-(3-acetoxypropyl)oxy-3-methyl-1,2,3,5-tetrahydroimidazo[2,1-b]quinazolin-2-one;
7-(3-acetoxypropyl)oxy-3-hydroxymethyl-1,2,3,5-tetrahydroimidazo[2,1-b]quinazolin-2-one;
7-(3-acetoxypropyl)oxy-3-benzyl-1,2,3,5-tetrahydroimidazo[2,1-b]quinazolin-2-one;
7-(3-acetoxypropyl)oxy-3-phenyl-1,2,3,5-tetrahydroimidazo[2,1-b]quinazolin-2-one;
7-(3-acetoxypropyl)oxy-3-carbamoylmethyl-1,2,3,5-tetrahydroimidazo[2,1-b]quinazolin-2-one;
7-(3-acetoxypropyl)oxy-3-carboxymethyl-1,2,3,5-tetrahydroimidazo[2,1-b]quinazolin-2-one;
7-(3-acetoxypropyl)oxy-3-ethyl-1,2,3,5-tetrahydroimidazo[2,1-b]quinazolin-2-one;
7-(3-acetoxypropyl)oxy-3-isopropyl-1,2,3,5-tetrahydroimidazo[2,1-b]quinazolin-2-one;
7-(4-acetoxybutyl)oxy-3-methyl-1,2,3,5-tetrahydroimidazo[2,1-b]quinazolin-2-one;
7-(4-acetoxybutyl)oxy-3-hydroxymethyl-1,2,3,5-tetrahydroimidazo[2,1-b]quinazolin-2-one;
7-(4-acetoxybutyl)oxy-3-benzyl-1,2,3,5-tetrahydroimidazo[2,1-b]quinazolin-2-one;
7-(4-acetoxybutyl)oxy-3-phenyl-1,2,3,5-tetrahydroimidazo[2,1-b]quinazolin-2-one;
7-(4-acetoxybutyl)oxy-3-carbamoylmethyl-1,2,3,5-tetrahydroimidazo[2,1-b]quinazolin-2-one;
7-(4-acetoxybutyl)oxy-3-carboxymethyl-1,2,3,5-tetrahydroimidazo[2,1-b]quinazolin-2-one;
7-(4-acetoxybutyl)oxy-3-ethyl-1,2,3,5-tetrahydroimidazo[2,1-b]quinazolin-2-one;
7-(4-acetoxybutyl)oxy-3-isopropyl-1,2,3,5-tetrahydroimidazo[2,1-b]quinazolin-2-one;
7-(5-acetoxypentyl)oxy-3-methyl-1,2,3,5-tetrahydroimidazo[2,1-b]quinazolin-2-one;
7-(5-acetoxypentyl)oxy-3-hydroxymethyl-1,2,3,5-tetrahydroimidazo[2,1-b]quinazolin-2-one;
7-(5-acetoxypentyl)oxy-3-benzyl-1,2,3,5-tetrahydroimidazo[2,1-b]quinazolin-2-one;
7-(5-acetoxypentyl)oxy-3-phenyl-1,2,3,5-tetrahydroimidazo[2,1-b]quinazolin-2-one;
7-(5-acetoxypentyl)oxy-3-carbamoylmethyl-1,2,3,5-tetrahydroimidazo[2,1-b]quinazolin-2-one;
7-(5-acetoxypentyl)oxy-3-carboxymethyl-1,2,3,5-tetrahydroimidazo[2,1-b]quinazolin-2-one;
7-(5-acetoxypentyl)oxy-3-ethyl-1,2,3,5-tetrahydroimidazo[2,1-b]quinazolin-2-one;
7-(5-acetoxypentyl)oxy-3-isopropyl-1,2,3,5-tetrahydroimidazo[2,1-b]quinazolin-2-one;
7-(7-acetoxyheptyl)oxy-3-methyl-1,2,3,5-tetrahydroimidazo[2,1-b]quinazolin-2-one;
7-(7-acetoxyheptyl)oxy-3-hydroxymethyl-1,2,3,5-tetrahydroimidazo[2,1-b]quinazolin-2-one;
7-(7-acetoxyheptyl)oxy-3-benzyl-1,2,3,5-tetrahydroimidazo[2,1-b]quinazolin-2-one;
7-(7-acetoxyheptyl)oxy-3-phenyl-1,2,3,5-tetrahydroimidazo[2,1-b]quinazolin-2-one;
7-(7-acetoxyheptyl)oxy-3-carbamoylmethyl-1,2,3,5-tetrahydroimidazo[2,1-b]quinazolin-2-one;
7-(7-acetoxyheptyl)oxy-3-carboxymethyl-1,2,3,5-tetrahydroimidazo[2,1-b]quinazolin-2-one;
7-(7-acetoxyheptyl)oxy-3-ethyl-1,2,3,5-tetrahydroimidazo[2,1-b]quinazolin-2-one;
7-(7-acetoxyheptyl)oxy-3-isopropyl-1,2,3,5-tetrahydroimidazo[2,1-b]quinazolin-2-one;
7-(8-acetoxyoctyl)oxy-3-methyl-1,2,3,5-tetrahydroimidazo[2,1-b]quinazolin-2-one;
7-(8-acetoxyoctyl)oxy-3-hydroxymethyl-1,2,3,5-tetrahydroimidazo[2,1-b]quinazolin-2-one;
7-(8-acetoxyoctyl)oxy-3-benzyl-1,2,3,5-tetrahydroimidazo[2,1-b]quinazolin-2-one;
7-(8-acetoxyoctyl)oxy-3-phenyl-1,2,3,5-tetrahydroimidazo[2,1-b]quinazolin-2-one;
7-(8-acetoxyoctyl)oxy-3-carbamoylmethyl-1,2,3,5-tetrahydroimidazo[2,1-b]quinazolin-2-one;
7-(8-acetoxyoctyl)oxy-3-carboxymethyl-1,2,3,5-tetrahydroimidazo[2,1-b]quinazolin-2-one;
7-(8-acetoxyoctyl)oxy-3-ethyl-1,2,3,5-tetrahydroimidazo[2,1-b]quinazolin-2-one;
7-(8-acetoxyoctyl)oxy-3-isopropyl-1,2,3,5-tetrahydroimidazo[2,1-b]quinazolin-2-one;
7-(2-acetoxyethyl)oxy-6-chloro-3-methyl-1,2,3,5-tetrahydroimidazo[2,1-b]quinazolin-2-one;
7-(2-acetoxyethyl)oxy-6-chloro-3-hydroxymethyl-1,2,3,5-tetrahydroimidazo[2,1-b]quinazolin-2-one;
7-(2-acetoxyethyl)oxy-6-chloro-3-benzyl-1,2,3,5-tetrahydroimidazo[2,1-b]quinazolin-2-one;
7-(2-acetoxyethyl)oxy-6-chloro-3-phenyl-1,2,3,5-tetrahydroimidazo[2,1-b]quinazolin-2-one;
7-(2-acetoxyethyl)oxy-6-chloro-3-carbamoylmethyl-1,2,3,5-tetrahydroimidazo[2,1-b]quinazolin-2-one;
7-(2-acetoxyethyl)oxy-6-chloro-3-carboxymethyl-1,2,3,5-tetrahydroimidazo[2,1-b]quinazolin-2-one;
7-(2-acetoxyethyl)oxy-6-chloro-3-ethyl-1,2,3,5-tetrahydroimidazo[2,1-b]quinazolin-2-one;
7-(2-acetoxyethyl)oxy-6-chloro-3-isopropyl-1,2,3,5-tetrahydroimidazo[2,1-b]quinazolin-2-one;
7-(3-acetoxypropyl)oxy-6-chloro-3-methyl-1,2,3,5-tetrahydroimidazo[2,1-b]quinazolin-2-one;
7-(3-acetoxypropyl)oxy-6-chloro-3-hydroxymethyl-1,2,3,5-tetrahydroimidazo[2,1-b]quinazolin-2-one;
7-(3-acetoxypropyl)oxy-6-chloro-3-benzyl-1,2,3,5-tetrahydroimidazo[2,1-b]quinazolin-2-one;
7-(3-acetoxypropyl)oxy-6-chloro-3-phenyl-1,2,3,5-tetrahydroimidazo[2,1-b]quinazolin-2-one;
7-(3-acetoxypropyl)oxy-6-chloro-3-carbamoylmethyl-1,2,3,5-tetrahydroimidazo[2,1-b]quinazolin-2-one;

7-(3-acetoxypropyl)oxy-6-chloro-3-carboxymethyl-1,2,3,5-tetrahydroimidazo[2,1-b]quinazolin-2-one;
7-(3-acetoxypropyl)oxy-6-chloro-3-ethyl-1,2,3,5-tetrahydroimidazo[2,1-b]quinazolin-2-one;
7-(3-acetoxypropyl)oxy-6-chloro-3-isopropyl-1,2,3,5-tetrahydroimidazo[2,1-b]quinazolin-2-one;
7-(4-acetoxybutyl)oxy-6-chloro-3-methyl-1,2,3,5-tetrahydroimidazo[2,1-b]quinazolin-2-one;
7-(4-acetoxybutyl)oxy-6-chloro-3-hydroxymethyl-1,2,3,5-tetrahydroimidazo[2,1-b]quinazolin-2-one;
7-(4-acetoxybutyl)oxy-6-chloro-3-benzyl-1,2,3,5-tetrahydroimidazo[2,1-b]quinazolin-2-one;
7-(4-acetoxybutyl)oxy-6-chloro-3-phenyl-1,2,3,5-tetrahydroimidazo[2,1-b]quinazolin-2-one;
7-(4-acetoxybutyl)oxy-6-chloro-3-carbamoylmethyl-1,2,3,5-tetrahydroimidazo[2,1-b]quinazolin-2-one;
7-(4-acetoxybutyl)oxy-6-chloro-3-carboxymethyl-1,2,3,5-tetrahydroimidazo[2,1-b]quinazolin-2-one;
7-(4-acetoxybutyl)oxy-6-chloro-3-ethyl-1,2,3,5-tetrahydroimidazo[2,1-b]quinazolin-2-one;
7-(4-acetoxybutyl)oxy-6-chloro-3-isopropyl-1,2,3,5-tetrahydroimidazo[2,1-b]quinazolin-2-one;
7-(5-acetoxypentyl)oxy-6-chloro-3-methyl-1,2,3,5-tetrahydroimidazo[2,1-b]quinazolin-2-one;
7-(5-acetoxypentyl)oxy-6-chloro-3-hydroxymethyl-1,2,3,5-tetrahydroimidazo[2,1-]quinazolin-2-one;
7-(5-acetoxypentyl)oxy-6-chloro-3-benzyl-1,2,3,5-tetrahydroimidazo[2,1-b]quinazolin-2-one;
7-(5-acetoxypentyl)oxy-6-chloro-3-phenyl-1,2,3,5-tetrahydroimidazo[2,1-b]quinazolin-2-one;
7-(5-acetoxypentyl)oxy-6-chloro-3-carbamoylmethyl-1,2,3,5-tetrahydroimidazo[2,1-b]quinazolin-2-one;
7-(5-acetoxypentyl)oxy-6-chloro-3-carboxymethyl-1,2,3,5-tetrahydroimidazo[2,1-b]quinazolin-2-one;
7-(5-acetoxypentyl)oxy-6-chloro-3-ethyl-1,2,3,5-tetrahydroimidazo[2,1-b]quinazolin-2-one;
7-(5-acetoxypentyl)oxy-6-chloro-3-isopropyl-1,2,3,5-tetrahydroimidazo[2,1-b]quinazolin-2-one;
7-(7-acetoxyheptyl)oxy-6-chloro-3-methyl-1,2,3,5-tetrahydroimidazo[2,1-b]quinazolin-2-one;
7-(7-acetoxyheptyl)oxy-6-chloro-3-hydroxymethyl-1,2,3,5-tetrahydroimidazo[2,1-b]quinazolin-2-one;
7-(7-acetoxyheptyl)oxy-6-chloro-3-benzyl-1,2,3,5-tetrahydroimidazo[2,1-b]quinazolin-2-one;
7-(7-acetoxyheptyl)oxy-6-chloro-3-phenyl-1,2,3,5-tetrahydroimidazo[2,1-b]quinazolin-2-one;
7-(7-acetoxyheptyl)oxy-6-chloro-3-carbamoylmethyl-1,2,3,5-tetrahydroimidazo[2,1-b]quinazolin-2-one;
7-(7-acetoxyheptyl)oxy-6-chloro-3-carboxymethyl-1,2,3,5-tetrahydroimidazo[2,1-b]quinazolin-2-one;
7-(7-acetoxyheptyl)oxy-6-chloro-3-ethyl-1,2,3,5-tetrahydroimidazo[2,1-b]quinazolin-2-one;
7-(7-acetoxyheptyl)oxy-6-chloro-3-isopropyl-1,2,3,5-tetrahydroimidazo[2,1-b]quinazolin-2-one;
7-(8-acetoxyoctyl)oxy-6-chloro-3-methyl-1,2,3,5-tetrahydroimidazo[2,1-b]quinazolin-2-one;
7-(8-acetoxyoctyl)oxy-6-chloro-3-hydroxymethyl-1,2,3,5-tetrahydroimidazo[2,1-b]quinazolin-2-one;
7-(8-acetoxyoctyl)oxy-6-chloro-3-benzyl-1,2,3,5-tetrahydroimidazo[2,1-b]quinazolin-2-one;
7-(8-acetoxyoctyl)oxy-6-chloro-3-phenyl-1,2,3,5-tetrahydroimidazo[2,1-b]quinazolin-2-one;
7-(8-acetoxyoctyl)oxy-6-chloro-3-carbamoylmethyl-1,2,3,5-tetrahydroimidazo[2,1-b]quinazolin-2-one;
7-(8-acetoxyoctyl)oxy-6-chloro-3-carboxymethyl-1,2,3,5-tetrahydroimidazo[2,1-b]quinazolin-2-one;
7-(8-acetoxyoctyl)oxy-6-chloro-3-ethyl-1,2,3,5-tetrahydroimidazo[2,1-b]quinazolin-2-one;
7-(8-acetoxyoctyl)oxy-6-chloro-3-isopropyl-1,2,3,5-tetrahydroimidazo[2,1-b]quinazolin-2-one;
7-(2-acetoxyethyl)oxy-6-methoxy-3-methyl-1,2,3,5-tetrahydroimidazo[2,1-b]quinazolin-2-one;
7-(2-acetoxyethyl)oxy-6-methoxy-3-hydroxymethyl-1,2,3,5-tetrahydroimidazo[2,1-b]quinazolin-2-one;
7-(2-acetoxyethyl)oxy-6-methoxy-3-benzyl-1,2,3,5-tetrahydroimidazo[2,1-b]quinazolin-2-one;
7-(2-acetoxyethyl)oxy-6-methoxy-3-phenyl-1,2,3,5-tetrahydroimidazo[2,1-b]quinazolin-2-one;
7-(2-acetoxyethyl)oxy-6-methoxy-3-carbamoylmethyl-1,2,3,5-tetrahydroimidazo[2,1-b]quinazolin-2-one;
7-(2-acetoxyethyl)oxy-6-methoxy-3-carboxymethyl-1,2,3,5-tetrahydroimidazo[2,1-b]quinazolin-2-one;
7-(2-acetoxyethyl)oxy-6-methoxy-3-ethyl-1,2,3,5-tetrahydroimidazo[2,1-b]quinazolin-2-one;
7-(2-acetoxyethyl)oxy-6-methoxy-3-isopropyl-1,2,3,5-tetrahydroimidazo[2,1-b]quinazolin-2-one;
7-(3-acetoxypropyl)oxy-6-methoxy-3-methyl-1,2,3,5-tetrahydroimidazo[2,1-b]quinazolin-2-one;
7-(3-acetoxypropyl)oxy-6-methoxy-3-hydroxymethyl-1,2,3,5-tetrahydroimidazo[2,1-b]quinazolin-2-one;
7-(3-acetoxypropyl)oxy-6-methoxy-3-benzyl-1,2,3,5-tetrahydroimidazo[2,1-b]quinazolin-2-one;
7-(3-acetoxypropyl)oxy-6-methoxy-3-phenyl-1,2,3,5-tetrahydroimidazo[2,1-b]quinazolin-2-one;
7-(3-acetoxypropyl)oxy-6-methoxy-3-carbamoylmethyl-1,2,3,5-tetrahydroimidazo[2,1-b]quinazolin-2-one;
7-(3-acetoxypropyl)oxy-6-methoxy-3-carboxymethyl-1,2,3,5-tetrahydroimidazo[2,1-b]quinazolin-2-one;
7-(3-acetoxypropyl)oxy-6-methoxy-3-ethyl-1,2,3,5-tetrahydroimidazo[2,1-b]quinazolin-2-one;
7-(3-acetoxypropyl)oxy-6-methoxy-3-isopropyl-1,2,3,5-tetrahydroimidazo[2,1-b]quinazolin-2-one;
7-(4-acetoxybutyl)oxy-6-methoxy-3-methyl-1,2,3,5-tetrahydroimidazo[2,1-b]quinazolin-2-one;
7-(4-acetoxybutyl)oxy-6-methoxy-3-hydroxymethyl-1,2,3,5-tetrahydroimidazo[2,1-b]quinazolin-2-one;
7-(4-acetoxybutyl)oxy-6-methoxy-3-benzyl-1,2,3,5-tetrahydroimidazo[2,1-b]quinazolin-2-one;
7-(4-acetoxybutyl)oxy-6-methoxy-3-phenyl-1,2,3,5-tetrahydroimidazo[2,1-b]quinazolin-2-one;
7-(4-acetoxybutyl)oxy-6-methoxy-3-carbamoylmethyl-1,2,3,5-tetrahydroimidazo[2,1-b]quinazolin-2-one;
7-(4-acetoxybutyl)oxy-6-methoxy-3-carboxymethyl-1,2,3,5-tetrahydroimidazo[2,1-b]quinazolin-2-one;
7-(4-acetoxybutyl)oxy-6-methoxy-3-ethyl-1,2,3,5-tetrahydroimidazo[2,1-b]quinazolin-2-one;
7-(4-acetoxybutyl)oxy-6-methoxy-3-isopropyl-1,2,3,5-tetrahydroimidazo[2,1-b]quinazolin-2-one;
7-(5-acetoxypentyl)oxy-6-methoxy-3-methyl-1,2,3,5-tetrahydroimidazo[2,1-b]quinazolin-2-one;
7-(5-acetoxypentyl)oxy-6-methoxy-3-hydroxymethyl-1,2,3,5-tetrahydroimidazo[2,1-b]quinazolin-2-one;
7-(5-acetoxypentyl)oxy-6-methoxy-3-benzyl-1,2,3,5-tetrahydroimidazo[2,1-b]quinazolin-2-one;
7-(5-acetoxypentyl)oxy-6-methoxy-3-phenyl-1,2,3,5-tetrahydroimidazo[2,1-b]quinazolin-2-one;
7-(5-acetoxypentyl)oxy-6-methoxy-3-carbamoylmethyl-1,2,3,5-tetrahydroimidazo[2,1-b]quinazolin-2-one;
7-(5-acetoxypentyl)oxy-6-methoxy-3-carboxymethyl-1,2,3,5-tetrahydroimidazo[2,1-b]quinazolin-2-one;
7-(5-acetoxypentyl)oxy-6-methoxy-3-ethyl-1,2,3,5-tetrahydroimidazo[2,1-b]quinazolin-2-one;
7-(5-acetoxypentyl)oxy-6-methoxy-3-isopropyl-1,2,3,5-tetrahydroimidazo[2,1-b]quinazolin-2-one;
7-(7-acetoxyheptyl)oxy-6-methoxy-3-methyl-1,2,3,5-tetrahydroimidazo[2,1-b]quinazolin-2-one;

7-(7-acetoxyheptyl)oxy-6-methoxy-3-hydroxymethyl-1,2,3,5-tetrahydroimidazo[2,1-b]quinazolin-2-one;
7-(7-acetoxyheptyl)oxy-6-methoxy-3-benzyl-1,2,3,5-tetrahydroimidazo[2,1-b]quinazolin-2-one;
7-(7-acetoxyheptyl)oxy-6-methoxy-3-phenyl-1,2,3,5-tetrahydroimidazo[2,1-b]quinazolin-2-one;
7-(7-acetoxyheptyl)oxy-6-methoxy-3-carbamoylmethyl-1,2,3,5-tetrahydroimidazo[2,1-b]quinazolin-2-one;
7-(7-acetoxyheptyl)oxy-6-methoxy-3-carboxymethyl-1,2,3,5-tetrahydroimidazo[2,1-b]quinazolin-2-one;
7-(7-acetoxyheptyl)oxy-6-methoxy-3-ethyl-1,2,3,5-tetrahydroimidazo[2,1-b]quinazolin-2-one;
7-(7-acetoxyheptyl)oxy-6-methoxy-3-isopropyl-1,2,3,5-tetrahydroimidazo[2,1-b]quinazolin-2-one;
7-(8-acetoxyoctyl)oxy-6-methoxy-3-methyl-1,2,3,5-tetrahydroimidazo[2,1-b]quinazolin-2-one;
7-(8-acetoxyoctyl)oxy-6-methoxy-3-hydroxymethyl-1,2,3,5-tetrahydroimidazo[2,1-b]quinazolin-2-one;
7-(8-acetoxyoctyl)oxy-6-methoxy-3-benzyl-1,2,3,5-tetrahydroimidazo[2,1-b]quinazolin-2-one;
7-(8-acetoxyoctyl)oxy-6-methoxy-3-phenyl-1,2,3,5-tetrahydroimidazo[2,1-b]quinazolin-2-one;
7-(8-acetoxyoctyl)oxy-6-methoxy-3-carbamoylmethyl-1,2,3,5-tetrahydroimidazo[2,1-b]quinazolin-2-one;
7-(8-acetoxyoctyl)oxy-6-methoxy-3-carboxymethyl-1,2,3,5-tetrahydroimidazo[2,1-b]quinazolin-2-one;
7-(8-acetoxyoctyl)oxy-6-methoxy-3-ethyl-1,2,3,5-tetrahydroimidazo[2,1-b]quinazolin-2-one;
7-(8-acetoxyoctyl)oxy-6-methoxy-3-isopropyl-1,2,3,5-tetrahydroimidazo[2,1-b]quinazolin-2-one;
7-(2-acetoxyethyl)oxy-3-L-methyl-1,2,3,5-tetrahydroimidazo[2,1-b]quinazolin-2-one;
7-(2-acetoxyethyl)oxy-3-L-hydroxymethyl-1,2,3,5-tetrahydroimidazo[2,1-b]quinazolin-2-one;
7-(2-acetoxyethyl)oxy-3-L-benzyl-1,2,3,5-tetrahydroimidazo[2,1-b]quinazolin-2-one;
7-(2-acetoxyethyl)oxy-3-L-phenyl-1,2,3,5-tetrahydroimidazo[2,1-b]quinazolin-2-one;
7-(2-acetoxyethyl)oxy-3-L-carbamoylmethyl-1,2,3,5-tetrahydroimidazo[2,1-b]quinazolin-2-one;
7-(2-acetoxyethyl)oxy-3-L-carboxymethyl-1,2,3,5-tetrahydroimidazo[2,1-b]quinazolin-2-one;
7-(2-acetoxyethyl)oxy-3-L-ethyl-1,2,3,5-tetrahydroimidazo[2,1-b]quinazolin-2-one;
7-(2-acetoxyethyl)oxy-3-L-isopropyl-1,2,3,5-tetrahydroimidazo[2,1-b]quinazolin-2-one; or
7-(3-acetoxypropyl)oxy-3-L-methyl-1,2,3,5-tetrahydroimidazo[2,1-b]quinazolin-2-one;
7-(3-acetoxypropyl)oxy-3-L-hydroxymethyl-1,2,3,5-tetrahydroimidazo[2,1-b]quinazolin-2-one;
7-(3-acetoxypropyl)oxy-3-L-benzyl-1,2,3,5-tetrahydroimidazo[2,1-b]quinazolin-2-one;
7-(3-acetoxypropyl)oxy-3-L-phenyl-1,2,3,5-tetrahydroimidazo[2,1-b]quinazolin-2-one;
7-(3-acetoxypropyl)oxy-3-L-carbamoylmethyl-1,2,3,5-tetrahydroimidazo[2,1-b]quinazolin-2-one;
7-(3-acetoxypropyl)oxy-3-L-carboxymethyl-1,2,3,5-tetrahydroimidazo[2,1-b]quinazolin-2-one;
7-(3-acetoxypropyl)oxy-3-L-ethyl-1,2,3,5-tetrahydroimidazo[2,1-b]quinazolin-2-one;
7-(3-acetoxypropyl)oxy-3-L-isopropyl-1,2,3,5-tetrahydroimidazo[2,1-b]quinazolin-2-one; or
7-(4-acetoxybutyl)oxy-3-L-methyl-1,2,3,5-tetrahydroimidazo[2,1-b]quinazolin-2-one;
7-(4-acetoxybutyl)oxy-3-L-hydroxymethyl-1,2,3,5-tetrahydroimidazo[2,1-b]quinazolin-2-one;
7-(4-acetoxybutyl)oxy-3-L-benzyl-1,2,3,5-tetrahydroimidazo[2,1-b]quinazolin-2-one;
7-(4-acetoxybutyl)oxy-3-L-phenyl-1,2,3,5-tetrahydroimidazo[2,1-b]quinazolin-2-one;
7-(4-acetoxybutyl)oxy-3-L-carbamoylmethyl-1,2,3,5-tetrahydroimidazo[2,1-b]quinazolin-2-one;
7-(4-acetoxybutyl)oxy-3-L-carboxymethyl-1,2,3,5-tetrahydroimidazo[2,1-b]quinazolin-2-one;
7-(4-acetoxybutyl)oxy-3-L-ethyl-1,2,3,5-tetrahydroimidazo[2,1-b]quinazolin-2-one;
7-(4-acetoxybutyl)oxy-3-L-isopropyl-1,2,3,5-tetrahydroimidazo[2,1-b]quinazolin-2-one; or
7-(5-acetoxypentyl)oxy-3-L-methyl-1,2,3,5-tetrahydroimidazo[2,1-b]quinazolin-2-one;
7-(5-acetoxypentyl)oxy-3-L-hydroxymethyl-1,2,3,5-tetrahydroimidazo[2,1-b]quinazolin-2-one;
7-(5-acetoxypentyl)oxy-3-L-benzyl-1,2,3,5-tetrahydroimidazo[2,1-b]quinazolin-2-one;
7-(5-acetoxypentyl)oxy-3-L-phenyl-1,2,3,5-tetrahydroimidazo[2,1-b]quinazolin-2-one;
7-(5-acetoxypentyl)oxy-3-L-carbamoylmethyl-1,2,3,5-tetrahydroimidazo[2,1-b]quinazolin-2-one;
7-(5-acetoxypentyl)oxy-3-L-carboxymethyl-1,2,3,5-tetrahydroimidazo[2,1-b]quinazolin-2-one;
7-(5-acetoxypentyl)oxy-3-L-ethyl-1,2,3,5-tetrahydroimidazo[2,1-b]quinazolin-2-one;
7-(5-acetoxypentyl)oxy-3-L-isopropyl-1,2,3,5-tetrahydroimidazo[2,1-b]quinazolin-2-one; or
7-(7-acetoxyheptyl)oxy-3-L-methyl-1,2,3,5-tetrahydroimidazo[2,1-b]quinazolin-2-one;
7-(7-acetoxyheptyl)oxy-3-L-hydroxymethyl-1,2,3,5-tetrahydroimidazo[2,1-b]quinazolin-2-one;
7-(7-acetoxyheptyl)oxy-3-L-benzyl-1,2,3,5-tetrahydroimidazo[2,1-b]quinazolin-2-one;
7-(7-acetoxyheptyl)oxy-3-L-phenyl-1,2,3,5-tetrahydroimidazo[2,1-b]quinazolin-2-one;
7-(7-acetoxyheptyl)oxy-3-L-carbamoylmethyl-1,2,3,5-tetrahydroimidazo[2,1-b]quinazolin-2-one;
7-(7-acetoxyheptyl)oxy-3-L-carboxymethyl-1,2,3,5-tetrahydroimidazo[2,1-b]quinazolin-2-one;
7-(7-acetoxyheptyl)oxy-3-L-ethyl-1,2,3,5-tetrahydroimidazo[2,1-b]quinazolin-2-one;
7-(7-acetoxyheptyl)oxy-3-L-isopropyl-1,2,3,5-tetrahydroimidazo[2,1-b]quinazolin-2-one; or
7-(8-acetoxyoctyl)oxy-3-L-methyl-1,2,3,5-tetrahydroimidazo[2,1-b]quinazolin-2-one;
7-(8-acetoxyoctyl)oxy-3-L-hydroxymethyl-1,2,3,5-tetrahydroimidazo[2,1-b]quinazolin-2-one;
7-(8-acetoxyoctyl)oxy-3-L-benzyl-1,2,3,5-tetrahydroimidazo[2,1-b]quinazolin-2-one;
7-(8-acetoxyoctyl)oxy-3-L-phenyl-1,2,3,5-tetrahydroimidazo[2,1-b]quinazolin-2-one;
7-(8-acetoxyoctyl)oxy-3-L-carbamoylmethyl-1,2,3,5-tetrahydroimidazo[2,1-b]quinazolin-2-one;
7-(8-acetoxyoctyl)oxy-3-L-carboxymethyl-1,2,3,5-tetrahydroimidazo[2,1-b]quinazolin-2-one;
7-(8-acetoxyoctyl)oxy-3-L-ethyl-1,2,3,5-tetrahydroimidazo[2,1-b]quinazolin-2-one;
7-(8-acetoxyoctyl)oxy-3-L-isopropyl-1,2,3,5-tetrahydroimidazo[2,1-b]quinazolin-2-one; or
7-(2-acetoxyethyl)oxy-3-D-methyl-1,2,3,5-tetrahydroimidazo[2,1-b]quinazolin-2-one;
7-(2-acetoxyethyl)oxy-3-D-hydroxymethyl-1,2,3,5-tetrahydroimidazo[2,1-b]quinazolin-2-one;
7-(2-acetoxyethyl)oxy-3-D-benzyl-1,2,3,5-tetrahydroimidazo[2,1-b]quinazolin-2-one;
7-(2-acetoxyethyl)oxy-3-D-phenyl-1,2,3,5-tetrahydroimidazo[2,1-b]quinazolin-2-one;
7-(2-acetoxyethyl)oxy-3-D-carbamoylmethyl-1,2,3,5-tetrahydroimidazo[2,1-b]quinazolin-2-one;

7-(2-acetoxyethyl)oxy-3-D-carboxymethyl-1,2,3,5-tetrahydroimidazo[2,1-b]quinazolin-2-one;
7-(2-acetoxyethyl)oxy-3-D-ethyl-1,2,3,5-tetrahydroimidazo[2,1-b]quinazolin-2-one;
7-(2-acetoxyethyl)oxy-3-D-isopropyl-1,2,3,5-tetrahydroimidazo[2,1-b]quinazolin-2-one; or
7-(3-acetoxypropyl)oxy-3-D-methyl-1,2,3,5-tetrahydroimidazo[2,1-b]quinazolin-2-one;
7-(3-acetoxypropyl)oxy-3-D-hydroxymethyl-1,2,3,5-tetrahydroimidazo[2,1-b]quinazolin-2-one;
7-(3-acetoxypropyl)oxy-3-D-benzyl-1,2,3,5-tetrahydroimidazo[2,1-b]quinazolin-2-one;
7-(3-acetoxypropyl)oxy-3-D-phenyl-1,2,3,5-tetrahydroimidazo[2,1-b]quinazolin-2-one;
7-(3-acetoxypropyl)oxy-3-D-carbamoylmethyl-1,2,3,5-tetrahydroimidazo[2,1-b]quinazolin-2-one;
7-(3-acetoxypropyl)oxy-3-D-carboxymethyl-1,2,3,5-tetrahydroimidazo[2,1-b]quinazolin-2-one;
7-(3-acetoxypropyl)oxy-3-D-ethyl-1,2,3,5-tetrahydroimidazo[2,1-b]quinazolin-2-one;
7-(3-acetoxypropyl)oxy-3-D-isopropyl-1,2,3,5-tetrahydroimidazo[2,1-b]quinazolin-2-one; or
7-(4-acetoxybutyl)oxy-3-D-methyl-1,2,3,5-tetrahydroimidazo[2,1-b]quinazolin-2-one;
7-(4-acetoxybutyl)oxy-3-D-hydroxymethyl-1,2,3,5-tetrahydroimidazo[2,1-b]quinazolin-2-one;
7-(4-acetoxybutyl)oxy-3-D-benzyl-1,2,3,5-tetrahydroimidazo[2,1-b]quinazolin-2-one;
7-(4-acetoxybutyl)oxy-3-D-phenyl-1,2,3,5-tetrahydroimidazo[2,1-b]quinazolin-2-one;
7-(4-acetoxybutyl)oxy-3-D-carbamoylmethyl-1,2,3,5-tetrahydroimidazo[2,1-b]quinazolin-2-one;
7-(4-acetoxybutyl)oxy-3-D-carboxymethyl-1,2,3,5-tetrahydroimidazo[2,1-b]quinazolin-2-one;
7-(4-acetoxybutyl)oxy-3-D-ethyl-1,2,3,5-tetrahydroimidazo[2,1-b]quinazolin-2-one;
7-(4-acetoxybutyl)oxy-3-D-isopropyl-1,2,3,5-tetrahydroimidazo[2,1-b]quinazolin-2-one; or
7-(5-acetoxypentyl)oxy-3-D-methyl-1,2,3,5-tetrahydroimidazo[2,1-b]quinazolin-2-one;
7-(5-acetoxypentyl)oxy-3-D-hydroxymethyl-1,2,3,5-tetrahydroimidazo[2,1-b]quinazolin-2-one;
7-(5-acetoxypentyl)oxy-3-D-benzyl-1,2,3,5-tetrahydroimidazo[2,1-b]quinazolin-2-one;
7-(5-acetoxypentyl)oxy-3-D-phenyl-1,2,3,5-tetrahydroimidazo[2,1-b]quinazolin-2-one;
7-(5-acetoxypentyl)oxy-3-D-carbamoylmethyl-1,2,3,5-tetrahydroimidazo[2,1-b]quinazolin-2-one;
7-(5-acetoxypentyl)oxy-3-D-carboxymethyl-1,2,3,5-tetrahydroimidazo[2,1-b]quinazolin-2-one;
7-(5-acetoxypentyl)oxy-3-D-ethyl-1,2,3,5-tetrahydroimidazo[2,1-b]quinazolin-2-one;
7-(5-acetoxypentyl)oxy-3-D-isopropyl-1,2,3,5-tetrahydroimidazo[2,1-b]quinazolin-2-one; or
7-(7-acetoxyheptyl)oxy-3-D-methyl-1,2,3,5-tetrahydroimidazo[2,1-b]quinazolin-2-one;
7-(7-acetoxyheptyl)oxy-3-D-hydroxymethyl-1,2,3,5-tetrahydroimidazo[2,1-b]quinazolin-2-one;
7-(7-acetoxyheptyl)oxy-3-D-benzyl-1,2,3,5-tetrahydroimidazo[2,1-b]quinazolin-2-one;
7-(7-acetoxyheptyl)oxy-3-D-phenyl-1,2,3,5-tetrahydroimidazo[2,1-b]quinazolin-2-one;
7-(7-acetoxyheptyl)oxy-3-D-carbamoylmethyl-1,2,3,5-tetrahydroimidazo[2,1-b]quinazolin-2-one;
7-(7-acetoxyheptyl)oxy-3-D-carboxymethyl-1,2,3,5-tetrahydroimidazo[2,1-b]quinazolin-2-one;
7-(7-acetoxyheptyl)oxy-3-D-ethyl-1,2,3,5-tetrahydroimidazo[2,1-b]quinazolin-2-one;
7-(7-acetoxyheptyl)oxy-3-D-isopropyl-1,2,3,5-tetrahydroimidazo[2,1-b]quinazolin-2-one; or
7-(8-acetoxyoctyl)oxy-3-D-methyl-1,2,3,5-tetrahydroimidazo[2,1-b]quinazolin-2-one;
7-(8-acetoxyoctyl)oxy-3-D-hydroxymethyl-1,2,3,5-tetrahydroimidazo[2,1-b]quinazolin-2-one;
7-(8-acetoxyoctyl)oxy-3-D-benzyl-1,2,3,5-tetrahydroimidazo[2,1-b]quinazolin-2-one;
7-(8-acetoxyoctyl)oxy-3-D-phenyl-1,2,3,5-tetrahydroimidazo[2,1-b]quinazolin-2-one;
7-(8-acetoxyoctyl)oxy-3-D-carbamoylmethyl-1,2,3,5-tetrahydroimidazo[2,1-b]quinazolin-2-one;
7-(8-acetoxyoctyl)oxy-3-D-carboxymethyl-1,2,3,5-tetrahydroimidazo[2,1-b]quinazolin-2-one;
7-(8-acetoxyoctyl)oxy-3-D-ethyl-1,2,3,5-tetrahydroimidazo[2,1-b]quinazolin-2-one;
7-(8-acetoxyoctyl)oxy-3-D-isopropyl-1,2,3,5-tetrahydroimidazo[2,1-b]quinazolin-2-one; and
other compounds depending on the $R_3$ substitution.

EXAMPLE 4

Preparation of 7-(X-Hydroxyalkyl)oxy-$R_3$ 1,2,3,5-Tetrahydroimidazo[2,1-b]quinazolin-2-ones This example illustrates the preparation of 7-(X-hydroxyalkyl)oxy-$R_3$-1,2,3,5-tetrahydroimidazo[2,1-b]quinazolin-2-ones wherein x is an integer of 2–8 and depends on the length of the alkyl chain which has 2–8 carbons.

I. Preparation of 7-(6-Hydroxyhexyl)oxy-1,2,3,5-Tetrahydroimidazo[2,1-b]quinazolin-2-one A suspension of 13.9 g (40 mmol) acetate from Example 3.I. in 100 ml of methanol was treated with 2 g (50 mmol) of sodium hydroxide dissolved in 20 ml of water. The mixture became clear momentarily, followed by formation of a copious precipitate, which was collected and dried over $P_2O_5$ to yield 7-(6-hydroxyhexyl)oxy-1,2,3,5-tetrahydroimidazo[2,1-b]quinazolin-2-one (11.5 g, 37.9 mmol, 95%) m.p. 236°–237° C.

II. a. Preparation of Other 7-(x-Hydroxyalkyl)oxy-1,2,3,5-tetrahydroimidazo[2,1-b]quinazolin-2-one Similarly to the above, substituting the acetate from Example 3.I. with acetates obtained in Example 3.II.a.b. and c., one obtains compounds wherein x is an integer of 2–8 depending on the alkyl chain length:
7-(2-hydroxyethyl)oxy-$R_3$-1,2,3,5-tetrahydroimidazo[2,1-b]quinazolin-2-one;
7-(3-hydroxypropyl)oxy-$R_3$-1,2,3,5-tetrahydroimidazo[2,1-b]quinazolin-2-one;
7-(4-hydroxybutyl)oxy-$R_3$-1,2,3,5-tetrahydroimidazo[2,1-b]quinazolin-2-one;
7-(5-hydroxypentyl)oxy-$R_3$-1,2,3,5-tetrahydroimidazo[2,1-b]quinazolin-2-one;
7-(7-hydroxyheptyl)oxy-$R_3$-1,2,3,5-tetrahydroimidazo[2,1-b]quinazolin-2-one;
7-(8-hydroxyoctyl)oxy-$R_3$-1,2,3,5-tetrahydroimidazo[2,1-b]quinazolin-2-one; wherein
$R_3$ can be either hydrogen, the residue of the amino acid as illustated in Example 3. Section II.a. and c. or other substituent as designated in the Summary.
Thus, one can obtain:
7-(2-hydroxyethyl)oxy-1,2,3,5-tetrahydroimidazo[2,1-b]quinazolin-2-one;

7-(3-hydroxypropyl)oxy-1,2,3,5-tetrahydroimidazo[2,1-b]quinazolin-2-one;
7-(4-hydroxybutyl)oxy-1,2,3,5-tetrahydroimidazo[2,1-b]quinazolin-2-one;
7-(5-hydroxypentyl)oxy-1,2,3,5-tetrahydroimidazo[2,1-b]quinazolin-2-one;
7-(7-hydroxyheptyl)oxy-1,2,3,5-tetrahydroimidazo[2,1-b]quinazolin-2-one;
7-(8-hydroxyoctyl)oxy-1,2,3,5-tetrahydroimidazo[2,1-b]quinazolin-2-one; or
7-(2-hydroxyethyl)oxy-3-methyl-1,2,3,5-tetrahydroimidazo[2,1-b]quinazolin-2-one;
7-(3-hydroxypropyl)oxy-3-methyl-1,2,3,5-tetrahydroimidazo[2,1-b]quinazolin-2-one;
7-(4-hydroxybutyl)oxy-3-methyl-1,2,3,5-tetrahydroimidazo[2,1-b]quinazolin-2-one;
7-(5-hydroxypentyl)oxy-3-methyl-1,2,3,5-tetrahydroimidazo[2,1-b]quinazolin-2-one;
7-(7-hydroxyheptyl)oxy-3-methyl-1,2,3,5-tetrahydroimidazo[2,1-b]quinazolin-2-one;
7-(8-hydroxyoctyl)oxy-3-methyl-1,2,3,5-tetrahydroimidazo[2,1-b]quinazolin-2-one;
7-(2-hydroxyethyl)oxy-3-hydroxymethyl-1,2,3,5-tetrahydroimidazo[2,1-b]quinazolin-2-one;
7-(3-hydroxypropyl)oxy-3-hydroxymethyl-1,2,3,5-tetrahydroimidazo[2,1-b]quinazolin-2-one;
7-(4-hydroxybutyl)oxy-3-hydroxymethyl-1,2,3,5-tetrahydroimidazo[2,1-b]quinazolin-2-one;
7-(5-hydroxypentyl)oxy-3-hydroxymethyl-1,2,3,5-tetrahydroimidazo[2,1-b]quinazolin-2-one;
7-(7-hydroxyheptyl)oxy-3-hydroxymethyl-1,2,3,5-tetrahydroimidazo[2,1-b]quinazolin-2-one;
7-(8-hydroxyoctyl)oxy-3-hydroxymethyl-1,2,3,5-tetrahydroimidazo[2,1-b]quinazolin-2-one;
7-(2-hydroxyethyl)oxy-3-benzyl-1,2,3,5-tetrahydroimidazo[2,1-b]quinazolin-2-one;
7-(3-hydroxypropyl)oxy-3-benzyl-1,2,3,5-tetrahydroimidazo[2,1-b]quinazolin-2-one;
7-(4-hydroxybutyl)oxy-3-benzyl-1,2,3,5-tetrahydroimidazo[2,1-b]quinazolin-2-one;
7-(5-hydroxypentyl)oxy-3-benzyl-1,2,3,5-tetrahydroimidazo[2,1-b]quinazolin-2-one;
7-(7-hydroxyheptyl)oxy-3-benzyl-1,2,3,5-tetrahydroimidazo[2,1-b]quinazolin-2-one;
7-(8-hydroxyoctyl)oxy-3-benzyl-1,2,3,5-tetrahydroimidazo[2,1-b]quinazolin-2-one;
7-(2-hydroxyethyl)oxy-3-phenyl-1,2,3,5-tetrahydroimidazo[2,1-b]quinazolin-2-one;
7-(3-hydroxypropyl)oxy-3-phenyl-1,2,3,5-tetrahydroimidazo[2,1-b]quinazolin-2-one;
7-(4-hydroxybutyl)oxy-3-phenyl-1,2,3,5-tetrahydroimidazo[2,1-b]quinazolin-2-one;
7-(5-hydroxypentyl)oxy-3-phenyl-1,2,3,5-tetrahydroimidazo[2,1-b]quinazolin-2-one;
7-(7-hydroxyheptyl)oxy-3-phenyl-1,2,3,5-tetrahydroimidazo[2,1-b]quinazolin-2-one;
7-(8-hydroxyoctyl)oxy-3-phenyl-1,2,3,5-tetrahydroimidazo[2,1-b]quinazolin-2-one;
7-(2-hydroxyethyl)oxy-3-carbamoylmethyl-1,2,3,5-tetrahydroimidazo[2,1-b]quinazolin-2-one;
7-(3-hydroxypropyl)oxy-3-carbamoylmethyl-1,2,3,5-tetrahydroimidazo[2,1-b]quinazolin-2-one;
7-(4-hydroxybutyl)oxy-3-carbamoylmethyl-1,2,3,5-tetrahydroimidazo[2,1-b]quinazolin-2-one;
7-(5-hydroxypentyl)oxy-3-carbamoylmethyl-1,2,3,5-tetrahydroimidazo[2,1-b]quinazolin-2-one;
7-(7-hydroxyheptyl)oxy-3-carbamoylmethyl-1,2,3,5-tetrahydroimidazo[2,1-b]quinazolin-2-one;
7-(8-hydroxyoctyl)oxy-3-carbamoylmethyl-1,2,3,5-tetrahydroimidazo[2,1-b]quinazolin-2-one;
7-(2-hydroxyethyl)oxy-3-carboxymethyl-1,2,3,5-tetrahydroimidazo[2,1-b]quinazolin-2-one;
7-(3-hydroxypropyl)oxy-3-carboxymethyl-1,2,3,5-tetrahydroimidazo[2,1-b]quinazolin-2-one;
7-(4-hydroxybutyl)oxy-3-carboxymethyl-1,2,3,5-tetrahydroimidazo[2,1-b]quinazolin-2-one;
7-(5-hydroxypentyl)oxy-3-carboxymethyl-1,2,3,5-tetrahydroimidazo[2,1-b]quinazolin-2-one;
7-(7-hydroxyheptyl)oxy-3-carboxymethyl-1,2,3,5-tetrahydroimidazo[2,1-b]quinazolin-2-one;
7-(8-hydroxyoctyl)oxy-3-carboxymethyl-1,2,3,5-tetrahydroimidazo[2,1-b]quinazolin-2-one;
7-(2-hydroxyethyl)oxy-3-ethyl-1,2,3,5-tetrahydroimidazo[2,1-b]quinazolin-2-one;
7-(3-hydroxypropyl)oxy-3-ethyl-1,2,3,5-tetrahydroimidazo[2,1-b]quinazolin-2-one;
7-(4-hydroxybutyl)oxy-3-ethyl-1,2,3,5-tetrahydroimidazo[2,1-b]quinazolin-2-one;
7-(5-hydroxypentyl)oxy-3-ethyl-1,2,3,5-tetrahydroimidazo[2,1-b]quinazolin-2-one;
7-(7-hydroxyheptyl)oxy-3-ethyl-1,2,3,5-tetrahydroimidazo[2,1-b]quinazolin-2-one;
7-(8-hydroxyoctyl)oxy-3-ethyl-1,2,3,5-tetrahydroimidazo[2,1-b]quinazolin-2-one;
7-(2-hydroxyethyl)oxy-3-isopropyl-1,2,3,5-tetrahydroimidazo[2,1-b]quinazolin-2-one;
7-(3-hydroxypropyl)oxy-3-isopropyl-1,2,3,5-tetrahydroimidazo[2,1-b]quinazolin-2-one;
7-(4-hydroxybutyl)oxy-3-isopropyl-1,2,3,5-tetrahydroimidazo[2,1-b]quinazolin-2-one;
7-(5-hydroxypentyl)oxy-3-isopropyl-1,2,3,5-tetrahydroimidazo[2,1-b]quinazolin-2-one;
7-(7-hydroxyheptyl)oxy-3-isopropyl-1,2,3,5-tetrahydroimidazo[2,1-b]quinazolin-2-one;
7-(8-hydroxyoctyl)oxy-3-isopropyl-1,2,3,5-tetrahydroimidazo[2,1-b]quinazolin-2-one;
7-(2-hydroxyethyl)oxy-6-chloro-3-methyl-1,2,3,5-tetrahydroimidazo[2,1-b]quinazolin-2-one;
7-(3-hydroxypropyl)oxy-6-chloro-3-methyl-1,2,3,5-tetrahydroimidazo[2,1-b]quinazolin-2-one;
7-(4-hydroxybutyl)oxy-6-chloro-3-methyl-1,2,3,5-tetrahydroimidazo[2,1-b]quinazolin-2-one;
7-(5-hydroxypentyl)oxy-6-chloro-3-methyl-1,2,3,5-tetrahydroimidazo[2,1-b]quinazolin-2-one;
7-(7-hydroxyheptyl)oxy-6-chloro-3-methyl-1,2,3,5-tetrahydroimidazo[2,1-b]quinazolin-2-one;
7-(8-hydroxyoctyl)oxy-6-chloro-3-methyl-1,2,3,5-tetrahydroimidazo[2,1-b]quinazolin-2-one;
7-(2-hydroxyethyl)oxy-6-chloro-3-hydroxymethyl-1,2,3,5-tetrahydroimidazo[2,1-b]quinazolin-2-one;
7-(3-hydroxypropyl)oxy-6-chloro-3-hydroxymethyl-1,2,3,5-tetrahydroimidazo[2,1-b]quinazolin-2-one;
7-(4-hydroxybutyl)oxy-6-chloro-3-hydroxymethyl-1,2,3,5-tetrahydroimidazo[2,1-b]quinazolin-2-one;
7-(5-hydroxypentyl)oxy-6-chloro-3-hydroxymethyl-1,2,3,5-tetrahydroimidazo[2,1-b]quinazolin-2-one;
7-(7-hydroxyheptyl)oxy-6-chloro-3-hydroxymethyl-1,2,3,5-tetrahydroimidazo[2,1-b]quinazolin-2-one;
7-(8-hydroxyoctyl)oxy-6-chloro-3-hydroxymethyl-1,2,3,5-tetrahydroimidazo[2,1-b]quinazolin-2-one;
7-(2-hydroxyethyl)oxy-6-chloro-3-benzyl-1,2,3,5-tetrahydroimidazo[2,1-b]quinazolin-2-one;
7-(3-hydroxypropyl)oxy-6-chloro-3-benzyl-1,2,3,5-tetrahydroimidazo[2,1-b]quinazolin-2-one;
7-(4-hydroxybutyl)oxy-6chloro-3-benzyl-1,2,3,5-tetrahydroimidazo[2,1-b]quinazolin-2-one;

7-(5-hydroxypentyl)oxy-6-chloro-3-benzyl-1,2,3,5-tetrahydroimidazo[2,1-b]quinazolin-2-one;
7-(7-hydroxyheptyl)oxy-6-chloro-3-benzyl-1,2,3,5-tetrahydroimidazo[2,1-b]quinazolin-2-one;
7-(8-hydroxyoctyl)oxy-6-chloro-3-benzyl-1,2,3,5-tetrahydroimidazo[2,1-b]quinazolin-2-one;
7-(2-hydroxyethyl)oxy-6-chloro-3-phenyl-1,2,3,5-tetrahydroimidazo[2,1-b]quinazolin-2-one;
7-(3-hydroxypropyl)oxy-6-chloro-3-phenyl-1,2,3,5-tetrahydroimidazo[2,1-b]quinazolin-2-one;
7-(4-hydroxybutyl)oxy-6-chloro-3-phenyl-1,2,3,5-tetrahydroimidazo[2,1-b]quinazolin-2-one;
7-(5-hydroxypentyl)oxy-6-chloro-3-phenyl-1,2,3,5-tetrahydroimidazo[2,1-b]quinazolin-2-one;
7-(7-hydroxyheptyl)oxy-6-chloro-3-phenyl-1,2,3,5-tetrahydroimidazo[2,1-b]quinazolin-2-one;
7-(8-hydroxyoctyl)oxy-6-chloro-3-phenyl-1,2,3,5-tetrahydroimidazo[2,1-b]quinazolin-2-one;
7-(2-hydroxyethyl)oxy-6-chloro-3-carbamoylmethyl-1,2,3,5-tetrahydroimidazo[2,1-b]quinazolin-2-one;
7-(3-hydroxypropyl)oxy-6-chloro-3-carbamoylmethyl-1,2,3,5-tetrahydroimidazo[2,1-b]quinazolin-2-one;
7-(4-hydroxybutyl)oxy-6-chloro-3-carbamoylmethyl-1,2,3,5-tetrahydroimidazo[2,1-b]quinazolin-2-one;
7-(5-hydroxypentyl)oxy-6-chloro-3-carbamoylmethyl-1,2,3,5-tetrahydroimidazo[2,1-b]quinazolin-2-one;
7-(7-hydroxyheptyl)oxy-6-chloro-3-carbamoylmethyl-1,2,3,5-tetrahydroimidazo[2,1-b]quinazolin-2-one;
7-(8-hydroxyoctyl)oxy-6-chloro-3-carbamoylmethyl-1,2,3,5-tetrahydroimidazo[2,1-b]quinazolin-2-one;
7-(2-hydroxyethyl)oxy-6-chloro-3-carboxymethyl-1,2,3,5-tetrahydroimidazo[2,1-b]quinazolin-2-one;
7-(3-hydroxypropyl)oxy-6-chloro-3-carboxymethyl-1,2,3,5-tetrahydroimidazo[2,1-b]quinazolin-2-one;
7-(4-hydroxybutyl)oxy-6-chloro-3-carboxymethyl-1,2,3,5-tetrahydroimidazo[2,1-b]quinazolin-2-one;
7-(5-hydroxypentyl)oxy-6-chloro-3-carboxymethyl-1,2,3,5-tetrahydroimidazo[2,1-b]quinazolin-2-one;
7-(7-hydroxyheptyl)oxy-6-chloro-3-carboxymethyl-1,2,3,5-tetrahydroimidazo[2,1-b]quinazolin-2-one;
7-(8-hydroxyoctyl)oxy-6-chloro-3-carboxymethyl-1,2,3,5-tetrahydroimidazo[2,1-b]quinazolin-2-one;
7-(2-hydroxyethyl)oxy-6-chloro-3-ethyl-1,2,3,5-tetrahydroimidazo[2,1-b]quinazolin-2-one;
7-(3-hydroxypropyl)oxy-6-chloro-3-ethyl-1,2,3,5-tetrahydroimidazo[2,1-b]quinazolin-2-one;
7-(4-hydroxybutyl)oxy-6-chloro-3-ethyl-1,2,3,5-tetrahydroimidazo[2,1-b]quinazolin-2-one;
7-(5-hydroxypentyl)oxy-6-chloro-3-ethyl-1,2,3,5-tetrahydroimidazo[2,1-b]quinazolin-2-one;
7-(7-hydroxyheptyl)oxy-6-chloro-3-ethyl-1,2,3,5-tetrahydroimidazo[2,1-b]quinazolin-2-one;
7-(8-hydroxyoctyl)oxy-6-chloro-3-ethyl-1,2,3,5-tetrahydroimidazo[2,1-b]quinazolin-2-one;
7-(2-hydroxyethyl)oxy-6-chloro-3-isopropyl-1,2,3,5-tetrahydroimidazo[2,1-b]quinazolin-2-one;
7-(3-hydroxypropyl)oxy-6-chloro-3-isopropyl-1,2,3,5-tetrahydroimidazo[2,1-b]quinazolin-2-one;
7-(4-hydroxybutyl)oxy-6-chloro-3-isopropyl-1,2,3,5-tetrahydroimidazo[2,1-b]quinazolin-2-one;
7-(5-hydroxypentyl)oxy-6-chloro-3-isopropyl-1,2,3,5-tetrahydroimidazo[2,1-b]quinazolin-2-one;
7-(7-hydroxyheptyl)oxy-6-chloro-3-isopropyl-1,2,3,5-tetrahydroimidazo[2,1-b]quinazolin-2-one;
7-(8-hydroxyoctyl)oxy-6-chloro-3-isopropyl-1,2,3,5-tetrahydroimidazo[2,1-b]quinazolin-2-one;
7-(2-hydroxyethyl)oxy-6-methoxy-3-methyl-1,2,3,5-tetrahydroimidazo[2,1-b]quinazolin-2-one;
7-(3-hydroxypropyl)oxy-6-methoxy-3-methyl-1,2,3,5-tetrahydroimidazo[2,1-b]quinazolin-2-one;
7-(4-hydroxybutyl)oxy-6-methoxy-3-methyl-1,2,3,5-tetrahydroimidazo[2,1-b]quinazolin-2-one;
7-(5-hydroxypentyl)oxy-6-methoxy-3-methyl-1,2,3,5-tetrahydroimidazo[2,1-b]quinazolin-2-one;
7-(7-hydroxyheptyl)oxy-6L-methoxy-3-methyl-1,2,3,5-tetrahydroimidazo[2,1-b]quinazolin-2-one;
7-(8-hydroxyoctyl)oxy-6-methoxy-3-methyl-1,2,3,5-tetrahydroimidazo[2,1-b]quinazolin-2-one;
7-(2-hydroxyethyl)oxy-6-methoxy-3-hydroxymethyl-1,2,3,5-tetrahydroimidazo[2,1-b]quinazolin-2-one;
7-(3-hydroxypropyl)oxy-6-methoxy-3-hydroxymethyl-1,2,3,5-tetrahydroimidazo[2,1-b]quinazolin-2-one;
7-(4-hydroxybutyl)oxy-6-methoxy-3-hydroxymethyl-1,2,3,5-tetrahydroimidazo[2,1-b]quinazolin-2-one;
7-(5-hydroxypentyl)oxy-6-methoxy-3-hydroxymethyl-1,2,3,5-tetrahydroimidazo[2,1-b]quinazolin-2-one;
7-(7-hydroxyheptyl)oxy-6-methoxy-3-hydroxymethyl-1,2,3,5-tetrahydroimidazo[2,1-b]quinazolin-2-one;
7-(8-hydroxyoctyl)oxy-6-methoxy-3-hydroxymethyl-1,2,3,5-tetrahydroimidazo[2,1-b]quinazolin-2-one;
7-(2-hydroxyethyl)oxy-6-methoxy-3-benzyl-1,2,3,5-tetrahydroimidazo[2,1-b]quinazolin-2-one;
7-(3-hydroxypropyl)oxy-6-methoxy-3-benzyl-1,2,3,5-tetrahydroimidazo[2,1-b]quinazolin-2-one;
7-(4-hydroxybutyl)oxy-6-methoxy-3-benzyl-1,2,3,5-tetrahydroimidazo[2,1-b]quinazolin-2-one;
7-(5-hydroxypentyl)oxy-6-methoxy-3-benzyl-1,2,3,5-tetrahydroimidazo[2,1-b]quinazolin-2-one;
7-(7-hydroxyheptyl)oxy-6-methoxy-3-benzyl-1,2,3,5-tetrahydroimidazo[2,1-b]quinazolin-2-one;
7-(8-hydroxyoctyl)oxy-6-methoxy-3-benzyl-1,2,3,5-tetrahydroimidazo[2,1-b]quinazolin-2-one;
7-(2-hydroxyethyl)oxy-6-methoxy-3-phenyl-1,2,3,5-tetrahydroimidazo[2,1-b]quinazolin-2-one;
7-(3-hydroxypropyl)oxy-6-methoxy-3-phenyl-1,2,3,5-tetrahydroimidazo[2,1-b]quinazolin-2-one;
7-(4-hydroxybutyl)oxy-6-methoxy-3-phenyl-1,2,3,5-tetrahydroimidazo[2,1-b]quinazolin-2-one;
7-(5-hydroxypentyl)oxy-6-methoxy-3-phenyl-1,2,3,5-tetrahydroimidazo[2,1-b]quinazolin-2-one;
7-(7-hydroxyheptyl)oxy-6-methoxy-3-phenyl-1,2,3,5-tetrahydroimidazo[2,1-b]quinazolin-2-one;
7-(8-hydroxyoctyl)oxy-6-methoxy-3-phenyl-1,2,3,5-tetrahydroimidazo[2,1-b]quinazolin-2-one;
7-(2-hydroxyethyl)oxy-6-methoxy-3-carbamoylmethyl-1,2,3,5-tetrahydroimidazo[2,1-b]quinazolin-2-one;
7-(3-hydroxypropyl)oxy-6-methoxy-3-carbamoylmethyl-1,2,3,5-tetrahydroimidazo[2,1-b]quinazolin-2-one;
7-(4-hydroxybutyl)oxy-6-methoxy-3-carbamoylmethyl-1,2,3,5-tetrahydroimidazo[2,1-b]quinazolin-2-one;
7-(5-hydroxypentyl)oxy-6-methoxy-3-carbamoylmethyl-1,2,3,5-tetrahydroimidazo[2,1-b]quinazolin-2-one;
7-(7-hydroxyheptyl)oxy-6-methoxy-3-carbamoylmethyl-1,2,3,5-tetrahydroimidazo[2,1-b]quinazolin-2-one;
7(8-hydroxyoctyl)oxy-6-methoxy-3-carbamoylmethyl-1,2,3,5-tetrahydroimidazo[2,1-b]quinazolin-2-one;
7-(2-hydroxyethyl)oxy-6-methoxy-3-carboxymethyl-1,2,3,5-tetrahydroimidazo[2,1-b]quinazolin-2-one;
7-(3-hydroxypropyl)oxy-6-methoxy-3-carboxymethyl-1,2,3,5-tetrahydroimidazo[2,1-b]quinazolin-2-one;
7-(4-hydroxybutyl)oxy-6-methoxy-3-carboxymethyl-1,2,3,5-tetrahydroimidazo[2,1-b]quinazolin-2-one;
7-(5-hydroxypentyl)oxy-6-methoxy-3-carboxymethyl-1,2,3,5-tetrahydroimidazo[2,1-b]quinazolin-2-one;
7-(7-hydroxyheptyl)oxy-6-methoxy-3-carboxymethyl-1,2,3,5-tetrahydroimidazo[2,1-b]quinazolin-2-one;

7-(8-hydroxyoctyl)oxy-6-methoxy-3-carboxymethyl-1,2,3,5-tetrahydroimidazo[2,1-b]quinazolin-2-one;
7-(2-hydroxyethyl)oxy-6-methoxy-3-ethyl-1,2,3,5-tetrahydroimidazo[2,1-b]quinazolin-2-one;
7-(3-hydroxypropyl)oxy-6-methoxy-3-ethyl-1,2,3,5-tetrahydroimidazo[2,1-b]quinazolin-2-one;
7-(4-hydroxybutyl)oxy-6-methoxy-3-ethyl-1,2,3,5-tetrahydroimidazo[2,1-b]quinazolin-2-one;
7-(5-hydroxypentyl)oxy-6-methoxy-3-ethyl-1,2,3,5-tetrahydroimidazo[2,1-b]quinazolin-2-one;
7-(7-hydroxyheptyl)oxy-6-methoxy-3-ethyl-1,2,3,5-tetrahydroimidazo[2,1-b]quinazolin-2-one;
7-(8-hydroxyoctyl)oxy-6-methoxy-3-ethyl-1,2,3,5-tetrahydroimidazo[2,1-b]quinazolin-2-one;
7-(2-hydroxyethyl)oxy-6-methoxy-3-isopropyl-1,2,3,5-tetrahydroimidazo[2,1-b]quinazolin-2-one;
7-(3-hydroxypropyl)oxy-6-methoxy-3-isopropyl-1,2,3,5-tetrahydroimidazo[2,1-b]quinazolin-2-one;
7-(4-hydroxybutyl)oxy-6-methoxy-3-isopropyl-1,2,3,5-tetrahydroimidazo[2,1-b]quinazolin-2-one;
7-(5-hydroxypentyl)oxy-6-methoxy-3-isopropyl-1,2,3,5-tetrahydroimidazo[2,1-b]quinazolin-2-one;
7-(7-hydroxyheptyl)oxy-6-methoxy-3-isopropyl-1,2,3,5-tetrahydroimidazo[2,1-b]quinazolin-2-one;
7-(8-hydroxyoctyl)oxy-6-methoxy-3-isopropyl-1,2,3,5-tetrahydroimidazo[2,1-b]quinazolin-2-one;
7-(2-hydroxyethyl)oxy-3-L-methyl-1,2,3,5-tetrahydroimidazo[2,1-b]quinazolin-2-one;
7-(3-hydroxypropyl)oxy-3-L-methyl-1,2,3,5-tetrahydroimidazo[2,1-b]quinazolin-2-one;
7-(4-hydroxybutyl)oxy-3-L-methyl-1,2,3,5-tetrahydroimidazo[2,1-b]quinazolin-2one;
7-(5-hydroxypentyl)oxy-3-L-methyl-1,2,3,5-tetrahydroimidazo[2,1-b]quinazolin-2-one;
7-(7-hydroxyheptyl)oxy-3-L-methyl-1,2,3,5-tetrahydroimidazo[2,1-b]quinazolin-2-one;
7-(8-hydroxyoctyl)oxy-3-L-methyl-1,2,3,5-tetrahydroimidazo[2,1-b]quinazolin-2-one;
7-(2-hydroxyethyl)oxy-3-L-hydroxymethyl-1,2,3,5-tetrahydroimidazo[2,1-b]quinazolin-2-one;
7-(3-hydroxypropyl)oxy-3-L-hydroxymethyl-1,2,3,5-tetrahydroimidazo[2,1-b]quinazolin-2-one;
7-(4-hydroxybutyl)oxy-3-L-hydroxymethyl-1,2,3,5-tetrahydroimidazo[2,1-b]quinazolin-2-one;
7-(5-hydroxypentyl)oxy-3-L-hydroxymethyl-1,2,3,5-tetrahydroimidazo[2,1-b]quinazolin-2-one;
7-(7-hydroxyheptyl)oxy-3-L-hydroxymethyl-1,2,3,5-tetrahydroimidazo[2,1-b]quinazolin-2-one;
7-(8-hydroxyoctyl)oxy-3-L-hydroxymethyl-1,2,3,5-tetrahydroimidazo[2,1-b]quinazolin-2-one;
7-(2-hydroxyethyl)oxy-3-L-benzyl-1,2,3,5-tetrahydroimidazo[2,1-b]quinazolin-2-one;
7-(3-hydroxypropyl)oxy-3-L-benzyl-1,2,3,5-tetrahydroimidazo[2,1-b]quinazolin-2-one;
7-(4-hydroxybutyl)oxy-3-L-benzyl-1,2,3,5-tetrahydroimidazo[2,1-b]quinazolin-2-one;
7-(5-hydroxypentyl)oxy-3-L-benzyl-1,2,3,5-tetrahydroimidazo[2,1-b]quinazolin-2-one;
7-(7-hydroxyheptyl)oxy-3-L-benzyl-1,2,3,5-tetrahydroimidazo[2,1-b]quinazolin-2-one;
7-(8-hydroxyoctyl)oxy-3-L-benzyl-1,2,3,5-tetrahydroimidazo[2,1-b]quinazolin-2-one;
7-(2-hydroxyethyl)oxy-3-L-phenyl-1,2,3,5-tetrahydroimidazo[2,1-b]quinazolin-2-one;
7-(3-hydroxypropyl)oxy-3-L-phenyl-1,2,3,5-tetrahydroimidazo[2,1-b]quinazolin-2-one;
7-(4-hydroxybutyl)oxy-3-L-phenyl-1,2,3,5-tetrahydroimidazo[2,1-b]quinazolin-2-one;
7-(5-hydroxypentyl)oxy-3-L-phenyl-1,2,3,5-tetrahydroimidazo[2,1-b]quinazolin-2-one;
7-(7-hydroxyheptyl)oxy-3-L-phenyl-1,2,3,5-tetrahydroimidazo[2,1-b]quinazolin-2-one;
7-(8-hydroxyoctyl)oxy-3-L-phenyl-1,2,3,5-tetrahydroimidazo[2,1-b]quinazolin-2-one;
7-(2-hydroxyethyl)oxy-3-L-carbamoylmethyl-1,2,3,5-tetrahydroimidazo[2,1-b]quinazolin-2-one;
7-(3-hydroxypropyl)oxy-3-L-carbamoylmethyl-1,2,3,5-tetrahydroimidazo[2,1-b]quinazolin-2-one;
7-(4-hydroxybutyl)oxy-2-L-carbamoylmethyl-1,2,3,5-tetrahydroimidazo[2,1-b]quinazolin-2-one;
7-(5-hydroxypentyl)oxy-3-L-carbamoylmethyl-1,2,3,5-tetrahydroimidazo[2,1-b]quinazolin-2-one;
7-(7-hydroxyheptyl)oxy-3-L-carbamoylmethyl-1,2,3,5-tetrahydroimidazo[2,1-b]quinazolin-2-one;
7-(8-hydroxyoctyl)oxy-3-L-carbamoylmethyl-1,2,3,5-tetrahydroimidazo[2,1-b]quinazolin-2-one;
7-(2-hydroxyethyl)oxy-3-L-carboxymethyl-1,2,3,5-tetrahydroimidazo[2,1-b]quinazolin-2-one;
7-(3-hydroxypropyl)oxy-3-L-carboxymethyl-1,2,3,5-tetrahydroimidazo[2,1-b]quinazolin-2-one;
7-(4-hydroxybutyl)oxy-3-L-carboxymethyl-1,2,3,5-tetrahydroimidazo[2,1-b]quinazolin-2-one;
7-(5-hydroxypentyl)oxy-3-L-carboxymethyl-1,2,3,5-tetrahydroimidazo[2,1-b]quinazolin-2-one;
7-(7-hydroxyheptyl)oxy-3-L-carboxymethyl-1,2,3,5-tetrahydroimidazo[2,1-b]quinazolin-2-one;
7-(8-hydroxyoctyl)oxy-3-L-carboxymethyl-1,2,3,5-tetrahydroimidazo[2,1-b]quinazolin-2-one;
7-(2-hydroxyethyl)oxy-3-L-ethyl-1,2,3,5-tetrahydroimidazo[2,1-b]quinazolin-2-one;
7-(3-hydroxypropyl)oxy-3-L-ethyl-1,2,3,5-tetrahydroimidazo[2,1-b]quinazolin-2-one;
7-(4-hydroxybutyl)oxy-3-L-ethyl-1,2,3,5-tetrahydroimidazo[2,1-b]quinazolin-2-one;
7-(5-hydroxypentyl)oxy-3-L-ethyl-1,2,3,5-tetrahydroimidazo[2,1-b]quinazolin-2-one;
7-(7-hydroxyheptyl)oxy-3-L-ethyl-1,2,3,5-tetrahydroimidazo[2,1-b]quinazolin-2-one;
7-(8-hydroxyoctyl)oxy-3-L-ethyl-1,2,3,5-tetrahydroimidazo[2,1-b]quinazolin-2-one;
7-(2-hydroxyethyl)oxy-3-L-isopropyl-1,2,3,5-tetrahydroimidazo[2,1-b]quinazolin-2-one;
7-(3-hydroxypropyl)oxy-3-L-isopropyl-1,2,3,5-tetrahydroimidazo[2,1-b]quinazolin-2-one;
7-(4-hydroxybutyl)oxy-3-L-isopropyl-1,2,3,5-tetrahydroimidazo[2,1-b]quinazolin-2-one;
7-(5-hydroxypentyl)oxy-3-L-isopropyl-1,2,3,5-tetrahydroimidazo[2,1-b]quinazolin-2-one;
7-(7-hydroxyheptyl)oxy-3-L-isopropyl-1,2,3,5-tetrahydroimidazo[2,1-b]quinazolin-2-one;
7-(8-hydroxyoctyl)oxy-3-L-isopropyl-1,2,3,5-tetrahydroimidazo[2,1-b]quinazolin-2-one; or
7-(2-hydroxyethyl)oxy-3-D-methyl-1,2,3,5-tetrahydroimidazo[2,1-b]quinazolin-2-one;
7-(3-hydroxypropyl)oxy-3-D-methyl-1,2,3,5-tetrahydroimidazo[2,1-b]quinazolin-2-one;
7-(4-hydroxybutyl)oxy-3-D-methyl-1,2,3,5-tetrahydroimidazo[2,1-b]quinazolin-2-one;
7-(5-hydroxypentyl)oxy-3-D-methyl-1,2,3,5-tetrahydroimidazo[2,1-b]quinazolin-2-one;
7-(7-hydroxyheptyl)oxy-3-D-methyl-1,2,3,5-tetrahydroimidazo[2,1-b]quinazolin-2-one;
7-(8-hydroxyoctyl)oxy-3-D-methyl-1,2,3,5-tetrahydroimidazo[2,1-b]quinazolin-2-one;
7-(2-hydroxyethyl)oxy-3-D-hydroxymethyl-1,2,3,5-tetrahydroimidazo[2,1-b]quinazolin-2-one;

7-(3-hydroxypropyl)oxy-3-D-hydroxymethyl-1,2,3,5-tetrahydroimidazo[2,1-b]quinazolin-2-one;
7-(4-hydroxybutyl)oxy-3-D-hydroxymethyl-1,2,3,5-tetrahydroimidazo[2,1-b]quinazolin-2-one;
7-(5-hydroxypentyl)oxy-3-D-hydroxymethyl-1,2,3,5-tetrahydroimidazo[2,1-b]quinazolin-2-one;
7-(7-hydroxyheptyl)oxy-3-D-hydroxymethyl-1,2,3,5-tetrahydroimidazo[2,1-b]quinazolin-2-one;
7-(8-hydroxyoctyl)oxy-3-D-hydroxymethyl-1,2,3,5-tetrahydroimidazo[2,1-b]quinazolin-2-one;
7-(2-hydroxyethyl)oxy-3-D-benzyl-1,2,3,5-tetrahydroimidazo[2,1-b]quinazolin-2-one;
7-(3-hydroxypropyl)oxy-3-D-benzyl-1,2,3,5-tetrahydroimidazo[2,1-b]quinazolin-2-one;
7-(4-hydroxybutyl)oxy-3-D-benzyl-1,2,3,5-tetrahydroimidazo[2,1-b]quinazoline-2-one;
7-(5-hydroxypentyl)oxy-3-D-benzyl-1,2,3,5-tetrahydroimidazo[2,1-b]quinazolin-2-one;
7-(7-hydroxyheptyl)oxy-3-D-benzyl-1,2,3,5-tetrahydroimidazo[2,1-b]quinazolin-2-one;
7-(8-hydroxyoctyl)oxy-3-D-benzyl-1,2,3,5-tetrahydroimidazo[2,1-b]quinazolin-2-one;
7-(2-hydroxyethyl)oxy-3-D-phenyl-1,2,3,5-tetrahydroimidazo[2,1-b]quinazolin-2-one;
7-(3-hydroxypropyl)oxy-3-D-phenyl-1,2,3,5-tetrahydroimidazo[2,1-b]quinazolin-2-one;
7-(4-hydroxybutyl)oxy-3-D-phenyl-1,2,3,5-tetrahydroimidazo[2,1-b]quinazolin-2-one;
7-(5-hydroxypentyl)oxy-3-D-phenyl-1,2,3,5-tetrahydroimidazo[2,1-b]quinazolin-2-one;
7(7-hydroxyheptyl)oxy-3-D-phenyl-1,2,3,5-tetrahydroimidazo[2,1-b]quinazolin-2-one;
7-(8-hydroxyoctyl)oxy-3-D-phenyl-1,2,3,5-tetrahydroimidazo[2,1-b]quinazolin-2-one;
7-(2-hydroxyethyl)oxy-3-D-carbamoylmethyl-1,2,3,5-tetrahydroimidazo[2,1-b]quinazolin-2-one;
7-(3-hydroxypropyl)oxy-3-D-carbamoylmethyl-1,2,3,5-tetrahydroimidazo[2,1-b]quinazolin-2-one;
7-(4-hydroxybutyl)oxy-3-D-carbamoylmethyl-1,2,3,5-tetrahydroimidazo[2,1-b]quinazolin-2-one;
7-(5-hydroxypentyl)oxy-3-D-carbamoylmethyl-1,2,3,5-tetrahydroimidazo[2,1-b]quinazolin-2-one;
7-(7-hydroxyheptyl)oxy-3-D-carbamoylmethyl-1,2,3,5-tetrahydroimidazo[2,1-b]quinazolin-2-one;
7-(7-hydroxyheptyl)oxy-3-D-carboxymethyl-1,2,3,5-tetrahydroimidazo[2,1-b]quinazolin-2-one;
7-(8-hydroxyoctyl)oxy-3-D-carbamoylmethyl-1,2,3,5-tetrahydroimidazo[2,1-b]quinazolin-2-one;
7-(2-hydroxyethyl)oxy-3-D-carboxymethyl-1,2,3,5-tetrahydroimidazo[2,1-b]quinazolin-2-one;
7-(3-hydroxypropyl)oxy-3-D-carboxymethyl-1,2,3,5-tetrahydroimidazo[2,1-b]quinazolin-2-one;
7-(4-hydroxybutyl)oxy-3-D-carboxymethyl-1,2,3,5-tetrahydroimidazo[2,1-b]quinazolin-2-one;
7-(5-hydroxypentyl)oxy-3-D-carboxymethyl-1,2,3,5-tetrahydroimidazo[2,1-b]quinazolin-2-one;
7-(7-hydroxyheptyl)oxy-3-D-carboxymethyl-1,2,3,5-tetrahydroimidazo[2,1-b]quinazolin-2-one;
7-(8-hydroxyoctyl)oxy-3-D-carboxymethyl-1,2,3,5-tetrahydroimidazo[2,1-b]quinazolin-2-one;
7-(2-hydroxyethyl)oxy-3-D-ethyl-1,2,3,5-tetrahydroimidazo[2,1-b]quinazolin-2-one;
7-(3-hydroxypropyl)oxy-3-D-ethyl-1,2,3,5-tetrahydroimidazo[2,1-b]quinazolin-2-one;
7-(4-hydroxybutyl)oxy-3-D-ethyl-1,2,3,5-tetrahydroimidazo[2,1-b]quinazolin-2-one;
7-(5-hydroxypentyl)oxy-3-D-ethyl-1,2,3,5-tetrahydroimidazo[2,1-b]quinazolin-2-one;
7-(7-hydroxyheptyl)oxy-3-D-ethyl-1,2,3,5-tetrahydroimidazo[2,1-b]quinazolin-2-one;
7-(8-hydroxyoctyl)oxy-3-D-ethyl-1,2,3,5-tetrahydroimidazo[2,1-b]quinazolin-2-one;
7-(2-hydroxyethyl)oxy-3-D-isopropyl-1,2,3,5-tetrahydroimidazo[2,1-b]quinazolin-2-one;
7-(3-hydroxypropyl)oxy-3-D-isopropyl-1,2,3,5-tetrahydroimidazo[2,1-b]quinazolin-2-one;
7-(4-hydroxybutyl)oxy-3-D-isopropyl-1,2,3,5-tetrahydroimidazo[2,1-b]quinazolin-2-one;
7-(5-hydroxypentyl)oxy-3-D-isopropyl-1,2,3,5-tetrahydroimidazo[2,1-b]quinazolin-2-one;
7-(7-hydroxyheptyl)oxy-3-D-isopropyl-1,2,3,5-tetrahydroimidazo[2,1-b]quinazolin-2-one;
7-(8-hydroxyoctyl)oxy-3-D-isopropyl-1,2,3,5-tetrahydroimidazo[2,1-b]quinazolin-2-one; and
others.

EXAMPLE 5

Preparation of 7-(X-(N-Imidazolyl)alkyl)oxy-1,2,3,5-Tetrahydroimidazo[2,1-b]quinazolin-2-ones This example illustrates the preparation of 7-(X-(N-imidazolyl)alkyl)oxy-1,2,3,5-tetrahydroimidazo[2,1-b]quinazolin-2-one wherein x is an integer of 2–8 and depends on the length of the alkyl carbon atom chain.

I. Preparation of 7-(6-(N-Imidazolyl)hexyl)oxy-1,2,3,5-tetrahydroimidazo[2,1-b]quinazolin-2-one A solution of 6.10 g (20 mmol) of alcohol from Example 4.I. and 9.05 g (40 mmol) of methyltriphenoxyphosphonium iodide in DMF was heated to 100° C. for 30 min. Evaporation of the mixture gave crude iodide, used directly below.

The crude iodide from the preceding paragraph was added to 25 g of molten imidazole at 125° C. Upon cooling, the solid was dissolved in 100 ml of chloroform, and was washed repeatedly with 10% ammonium hydroxide, followed by brine. Upon evaporation and chromatography, 7-(6-(N-imidazolyl)hexyl)oxy-1,2,3,5-tetrahydroimidazo[2,1-b]quinazolin-2-one was obtained, m.p. 188°–189° C.

II. Preparation of Various 7-(6-(N-Imidazolyl)alkyl)oxy-1,2,3,5-tetrahydroimidazo[2,1-b]quinazolin-2-one Similarly, other 7-(6-(N-imidazolyl)alkyl)oxy-1,2,3,5-tetrahydroimidazo[2,1-b]quinazolin-2-one can be prepared by substituting the alcohol obtained in Example 4.I. by alcohols described in Example 4.II. In this way, one obtains:
7-(2-(N-imidazolyl)ethyl)oxy-$R_3$-1,2,3,5-tetrahydroimidazo[2,1-b]quinazolin-2-one;
7-(3-(N-imidazolyl)propyl)oxy-$R_3$-1,2,3,5-tetrahydroimidazo[2,1-b]quinazolin-2-one;
7-(4-(N-imidazolyl)butyl)oxy-$R_3$-1,2,3,5-tetrahydroimidazo[2,1-b]quinazolin-2-one;
7-(5-(N-imidazolyl)pentyl)oxy-$R_3$-1,2,3,5-tetrahydroimidazo[2,1-b]quinazolin-2-one;
7-(7-(N-imidazolyl)heptyl)oxy-$R_3$-1,2,3,5-tetrahydroimidazo[2,1-b]quinazolin-2-one;
7-(8-(N-imidazolyl)octyl)oxy-$R_3$-1,2,3,5-tetrahydroimidazo[2,1-b]quinazolin-2-one;
wherein $R_3$ can be either hydrogen, the residue of the amino acid as illustrated in Example 3. Section II.a. and c. or other substituent as designated in Summary.

Thus, one can obtain:
7-(2-(N-imidazolyl)ethyl)oxy-1,2,3,5-tetrahydroimidazo-[2,1-b]quinazolin-2-one;
7-(3-(N-imidazolyl)propyl)oxy-1,2,3,5-tetrahydroimidazo-[2,1-b]quinazolin-2-one;
7-(4-(N-imidazolyl)butyl)oxy-1,2,3,5-tetrahydroimidazo-[2,1-b]quinazolin-2-one;
7-(5-(N-imidazolyl)pentyl)oxy-1,2,3,5-tetrahydroimidazo-[2,1-b]quinazolin-2-one;
7-(7-(N-imidazolyl)heptyl)oxy-1,2,3,5-tetrahydroimidazo-[2,1-b]quinazolin-2-one;
7-(8-(N-imidazolyl)octyl)oxy-1,2,3,5-tetrahydroimidazo-[2,1-b]quinazolin-2-one; or
7-(2-(N-imidazolyl)ethyl)oxy-3-methyl-1,2,3,5-tetrahydroimidazo[2,1-b]quinazolin-2-one;
7-(3-(N-imidazolyl)propyl)oxy-3-methyl-1,2,3,5-tetrahydroimidazo[2,1-b]quinazolin-2-one;
7-(4-(N-imidazolyl)butyl)oxy-3-methyl-1,2,3,5-tetrahydroimidazo[2,1-b]quinazolin-2-one;
7-(5-(N-imidazolyl)pentyl)oxy-3-methyl-1,2,3,5-tetrahydroimidazo[2,1-b]quinazolin-2-one;
7-(7-(N-imidazolyl)heptyl)oxy-3-methyl-1,2,3,5-tetrahydroimidazo[2,1-b]quinazolin-2-one;
7-(8-(N-imidazolyl)octyl)oxy-3-methyl-1,2,3,5-tetrahydroimidazo[2,1-b]quinazolin-2-one;
7-(2-(N-imidazolyl)ethyl)oxy-3-hydroxymethyl-1,2,3,5-tetrahydroimidazo[2,1-b]quinazolin-2-one;
7-(3-(N-imidazolyl)propyl)oxy-3-hydroxymethyl-1,2,3,5-tetrahydroimidazo[2,1-b]quinazolin-2-one;
7-(4-(N-imidazolyl)butyl)oxy-3-hydroxymethyl-1,2,3,5-tetrahydroimidazo[2,1-b]quinazolin-2-one;
7-(5-(N-imidazolyl)pentyl)oxy-3-hydroxymethyl-1,2,3,5-tetrahydroimidazo[2,1-b]quinazolin-2-one;
7-(7-(N-imidazolyl)heptyl)oxy-3-hydroxymethyl-1,2,3,5-tetrahydroimidazo[2,1-b]quinazolin-2-one;
7-(8-(N-imidazolyl)octyl)oxy-3-hydroxymethyl-1,2,3,5-tetrahydroimidazo[2,1-b]quinazolin-2-one;
7-(2-(N-imidazolyl)ethyl)oxy-3-benzyl-1,2,3,5-tetrahydroimidazo[2,1-b]quinazolin-2-one;
7-(3-(N-imidazolyl)propyl)oxy-3-benzyl-1,2,3,5-tetrahydroimidazo[2,1-b]quinazolin-2-one;
7-(4-(N-imidazolyl)butyl)oxy-3-benzyl-1,2,3,5-tetrahydroimidazo[2,1-b]quinazolin-2-one;
7-(5-(N-imidazolyl)pentyl)oxy-3-benzyl-1,2,3,5-tetrahydroimidazo[2,1-b]quinazolin-2-one;
7-(7-(N-imidazolyl)heptyl)oxy-3-benzyl-1,2,3,5-tetrahydroimidazo[2,1-b]quinazolin-2-one;
7-(8-(N-imidazolyl)octyl)oxy-3-benzyl-1,2,3,5-tetrahydroimidazo[2,1-b]quinazolin-2-one;
7-(2-(N-imidazolyl)ethyl)oxy-3-phenyl-1,2,3,5-tetrahydroimidazo[2,1-b]quinazolin-2-one;
7-(3-(N-imidazolyl)propyl)oxy-3-phenyl-1,2,3,5-tetrahydroimidazo[2,1-b]quinazolin-2-one;
7-(4-(N-imidazolyl)butyl)oxy-3-phenyl-1,2,3,5-tetrahydroimidazo[2,1-b]quinazolin-2-one;
7-(5-(N-imidazolyl)pentyl)oxy-3-phenyl-1,2,3,5-tetrahydroimidazo[2,1-b]quinazolin-2-one;
7-(7-(N-imidazolyl)heptyl)oxy-3-phenyl-1,2,3,5-tetrahydroimidazo[2,1-b]quinazolin-2-one;
7-(8-(N-imidazolyl)octyl)oxy-3-phenyl-1,2,3,5-tetrahydroimidazo[2,1-b]quinazolin-2-one;
7-(2-(N-imidazolyl)ethyl)oxy-3-carbamoylmethyl-1,2,3,5-tetrahydroimidazo[2,1-b]quinazolin-2-one;
7-(3-(N-imidazolyl)propyl)oxy-3-carbamoylmethyl-1,2,3,5-tetrahydroimidazo[2,1-b]quinazolin-2-one;
7-(4-(N-imidazolyl)butyl)oxy-3-carbamoylmethyl-1,2,3,5-tetrahydroimidazo[2,1-b]quinazolin-2-one;
7-(5-(N-imidazolyl)pentyl)oxy-3-carbamoylmethyl-1,2,3,5-tetrahydroimidazo[2,1-b]quinazolin-2-one;
7-(7-(N-imidazolyl)heptyl)oxy-3-carbamoylmethyl-1,2,3,5-tetrahydroimidazo[2,1-b]quinazolin-2-one;
7-(8-(N-imidazolyl)octyl)oxy-3-carbamoylmethyl-1,2,3,5-tetrahydroimidazo[2,1-b]quinazolin-2-one;
7-(2-(N-imidazolyl)ethyl)oxy-3-carboxymethyl-1,2,3,5-tetrahydroimidazo[2,1-b]quinazolin-2-one;
7-(3-(N-imidazolyl)propyl)oxy-3-carboxymethyl-1,2,3,5-tetrahydroimidazo[2,1-b]quinazolin-2-one;
7-(4-(N-imidazolyl)butyl)oxy-3-carboxymethyl-1,2,3,5-tetrahydroimidazo[2,1-b]quinazolin-2-one;
7-(5-(N-imidazolyl)pentyl)oxy-3-carboxymethyl-1,2,3,5-tetrahydroimidazo[2,1-b]quinazolin-2-one;
7-(7-(N-imidazolyl)heptyl)oxy-3-carboxymethyl-1,2,3,5-tetrahydroimidazo[2,1-b]quinazolin-2-one;
7-(8-(N-imidazolyl)octyl)oxy-3-carboxymethyl-1,2,3,5-tetrahydroimidazo[2,1-b]quinazolin-2-one;
7-(2-(N-imidazolyl)ethyl)oxy-3-ethyl-1,2,3,5-tetrahydroimidazo[2,1-b]quinazolin-2-one;
7-(3-(N-imidazolyl)propyl)oxy-3-ethyl-1,2,3,5-tetrahydroimidazo[2,1-b]quinazolin-2-one;
7-(4-(N-imidazolyl)butyl)oxy-3-ethyl-1,2,3,5-tetrahydroimidazo[2,1-b]quinazolin-2-one;
7-(5-(N-imidazolyl)pentyl)oxy-3-ethyl-1,2,3,5-tetrahydroimidazo[2,1-b]quinazolin-2-one;
7-(7-(N-imidazolyl)heptyl)oxy-3-ethyl-1,2,3,5-tetrahydroimidazo[2,1-b]quinazolin-2-one;
7-(8-(N-imidazolyl)octyl)oxy-3-ethyl-1,2,3,5-tetrahydroimidazo[2,1-b]quinazolin-2-one;
7-(2-(N-imidazolyl)ethyl)oxy-3-isopropyl-1,2,3,5-tetrahydroimidazo[2,1-b]quinazolin-2-one;
7-(3-(N-imidazolyl)propyl)oxy-3-isopropyl-1,2,3,5-tetrahydroimidazo[2,1-b]quinazolin-2-one;
7-(4-(N-imidazolyl)butyl)oxy-3-isopropyl-1,2,3,5-tetrahydroimidazo[2,1-b]quinazolin-2-one;
7-(5-(N-imidazolyl)pentyl)oxy-3-isopropyl-1,2,3,5-tetrahydroimidazo[2,1-b]quinazolin-2-one;
7-(7-(N-imidazolyl)heptyl)oxy-3-isopropyl-1,2,3,5-tetrahydroimidazo[2,1-b]quinazolin-2-one;
7-(8-(N-imidazolyl)octyl)oxy-3-isopropyl-1,2,3,5-tetrahydroimidazo[2,1-b]quinazolin-2-one;
7-(2-(N-imidazolyl)ethyl)oxy-6-chloro-3-methyl-1,2,3,5-tetrahydroimidazo[2,1-b]quinzolin-2-one;
7-(3-(N-imidazolyl)propyl)oxy-6-chloro-3-methyl-1,2,3,5-tetrahydroimidazo[2,1-b]quinazolin-2-one;
7-(4-(N-imidazolyl)butyl)oxy-6-chloro-3-methyl-1,2,3,5-tetrahydroimidazo[2,1-b]quinazolin-2-one;
7-(5-(N-imidazolyl)pentyl)oxy-6-chloro-3-methyl-1,2,3,5-tetrahydroimidazo[2,1-b]quinazolin-2-one;
7-(7-(N-imidazolyl)heptyl)oxy-6-chloro-3-methyl-1,2,3,5-tetrahydroimidazo[2,1-b]quinazolin-2-one;
7-(8-(N-imidazolyl)octyl)oxy-6-chloro-3-methyl-1,2,3,5-tetrahydroimidazo[2,1-b]quinazolin-2-one;
7-(2-(N-imidazolyl)ethyl)oxy-6-chloro-3-hydroxymethyl-1,2,3,5-tetrahydroimidazo[2,1-b]quinazolin-2-one;
7-(3-(N-imidazolyl)propyl)oxy-6-chloro-3-hydroxymethyl-1,2,3,5-tetrahydroimidazo[2,1-b]quinazolin-2-one;
7-(4-(N-imidazolyl)butyl)oxy-6-chloro-3-hydroxymethyl-1,2,3,5-tetrahydroimidazo[2,1-b]quinazolin-2-one;
7-(5-(N-imidazolyl)pentyl)oxy-6-chloro-3-hydroxymethyl-1,2,3,5-tetrahydroimidazo[2,1-b]quinazolin-2-one;
7-(7-(N-imidazolyl)heptyl)oxy-6-chloro-3-hydroxymethyl-1,2,3,5-tetrahydroimidazo[2,1-b]quinazolin-2-one;

7-(8-(N-imidazolyl)octyl)oxy-6-chloro-3-hydroxymethyl-1,2,3,5-tetrahydroimidazo[2,1-b]quinazolin-2-one;
7-(2-(N-imidazolyl)ethyl)oxy-6-chloro-3-benzyl-1,2,3,5-tetrahydroimidazo[2,1-b]quinazolin-2-one;
7-(3-(N-imidazolyl)propyl)oxy-6-chloro-3-benzyl-1,2,3,5-tetrahydroimidazo[2,1-b]quinazolin-2-one;
7-(4-(N-imidazolyl)butyl)oxy-6-chloro-3-benzyl-1,2,3,5-tetrahydroimidazo[2,1-b]quinazolin-2-one;
7-(5-(N-imidazolyl)pentyl)oxy-6-chloro-3-benzyl-1,2,3,5-tetrahydroimidazo[2,1-b]quinazolin-2-one;
7-(7-(N-imidazolyl)heptyl)oxy-6-chloro-3-benzyl-1,2,3,5-tetrahydroimidazo[2,1-b]quinazolin-2-one;
7-(8-(N-imidazolyl)octyl)oxy-6-chloro-3-benzyl-1,2,3,5-tetrahydroimidazo[2,1-b]quinazolin-2-one;
7-(2-(N-imidazolyl)ethyl)oxy-6-chloro-3-phenyl-1,2,3,5-tetrahydroimidazo[2,1-b]quinazolin-2-one;
7-(3-(N-imidazolyl)propyl)oxy-6-chloro-3-phenyl-1,2,3,5-tetrahydroimidazo[2,1-b]quinazolin-2-one;
7-(4-(N-imidazolyl)butyl)oxy-6-chloro-3-phenyl-1,2,3,5-tetrahydroimidazo[2,1-b]quinazolin-2-one;
7-(5-(N-imidazolyl)pentyl)oxy-6-chloro-3-phenyl-1,2,3,5-tetrahydroimidazo[2,1-b]quinazolin-2-one;
7-(7-(N-imidazolyl)heptyl)oxy-6-chloro-3-phenyl-1,2,3,5-tetrahydroimidazo[2,1-b]quinazolin-2-one;
7-(8-(N-imidazolyl)octyl)oxy-6-chloro-3-phenyl-1,2,3,5-tetrahydroimidazo[2,1-b]quinazolin-2-one;
7-(2-(N-imidazolyl)ethyl)oxy-6-chloro-3-carbamoylmethyl-1,2,3,5-tetrahydroimidazo[2,1-b]quinazolin-2-one;
7-(3-(N-imidazolyl)propyl)oxy-6-chloro-3-carbamoylmethyl-1,2,3,5-tetrahydroimidazo[2,1-b]quinazolin-2-one;
7-(4-(N-imidazolyl)butyl)oxy-6-chloro-3-carbamoylmethyl-1,2,3,5-tetrahydroimidazo[2,1-b]quinazolin-2-one;
7-(5-(N-imidazolyl)pentyl)oxy-6-chloro-3-carbamoylmethyl-1,2,3,5-tetrahydroimidazo[2,1-b]quinazolin-2-one;
7-(7-(N-imidazolyl)heptyl)oxy-6-chloro-3-carbamoylmethyl-1,2,3,5-tetrahydroimidazo[2,1-b]quinazolin-2-one;
7-(8-(N-imidazolyl)octyl)oxy-6-chloro-3-carbamoylmethyl-1,2,3,5-tetrahydroimidazo[2,1-b]quinazolin-2-one;
7-(2-(N-imidazolyl)ethyl)oxy-6-chloro-3-carboxymethyl-1,2,3,5-tetrahydroimidazo[2,1-b]quinazolin-2-one;
7-(3-(N-imidazolyl)propyl)oxy-6-chloro-3-carboxymethyl-1,2,3,5-tetrahydroimidazo[2,1-b]quinazolin-2-one;
7-(4-(N-imidazolyl)butyl)oxy-6-chloro-3-carboxymethyl-1,2,3,5-tetrahydroimidazo[2,1-b]quinazolin-2-one;
7-(5-(N-imidazolyl)pentyl)oxy-6-chloro-3-carboxymethyl-1,2,3,5-tetrahydroimidazo[2,1-b]quinazolin-2-one;
7-(7-(N-imidazolyl)heptyl)oxy-6-chloro-3-carboxymethyl-1,2,3,5-tetrahydroimidazo[2,1-b]quinazolin-2-one;
7-(8-(N-imidazolyl)octyl)oxy-6-chloro-3-carboxymethyl-1,2,3,5-tetrahydroimidazo[2,1-b]quinazolin-2-one;
7-(2-(N-imidazolyl)ethyl)oxy-6-chloro-3-ethyl-1,2,3,5-tetrahydroimidazo[2,1-b]quinazolin-2-one;
7-(3-(N-imidazolyl)propyl)oxy-6-chloro-3-ethyl-1,2,3,5-tetrahydroimidazo[2,1-b]quinazolin-2-one;
7-(4-(N-imidazolyl)butyl)oxy-6-chloro-3-ethyl-1,2,3,5-tetrahydroimidazo[2,1-b]quinazolin-2-one;
7-(5-(N-imidazolyl)pentyl)oxy-6-chloro-3-ethyl-1,2,3,5-tetrahydroimidazo[2,1-b]quinazolin-2-one;
7-(7-(N-imidazolyl)heptyl)oxy-6-chloro-3-ethyl-1,2,3,5-tetrahydroimidazo[2,1-b]quinazolin-2-one;
7-(8-(N-imidazolyl)octyl)oxy-6-chloro-3-ethyl-1,2,3,5-tetrahydroimidazo[2,1-b]quinazolin-2-one;
7-(2-(N-imidazolyl)ethyl)oxy-6-chloro-3-isopropyl-1,2,3,5-tetrahydroimidazo[2,1-b]quinazolin-2-one;
7-(3-(N-imidazolyl)propyl)oxy-6-chloro-3-isopropyl-1,2,3,5-tetrahydroimidazo[2,1-b]quinazolin-2-one;
7-(4-(N-imidazolyl)butyl)oxy-6-chloro-3-isopropyl-1,2,3,5-tetrahydroimidazo[2,1-b]quinazolin-2-one;
7-(5-(N-imidazolyl)pentyl)oxy-6-chloro-3-isopropyl-1,2,3,5-tetrahydroimidazo[2,1-b]quinazolin-2-one;
7-(7-(N-imidazolyl)heptyl)oxy-6-chloro-3-isopropyl-1,2,3,5-tetrahydroimidazo[2,1-b]quinazolin-2-one;
7-(8-(N-imidazolyl)octyl)oxy-6-chloro-3-isopropyl-1,2,3,5-tetrahydroimidazo[2,1-b]quinazolin-2-one;
7-(2-(N-imidazolyl)ethyl)oxy-6-methoxy-3-methyl-1,2,3,5-tetrahydroimidazo[2,1-b]quinazolin-2-one;
7-(3-(N-imidazolyl)propyl)oxy-6-methoxy-3-methyl-1,2,3,5-tetrahydroimidazo[2,1-b]quinazolin-2-one;
7-(4-(N-imidazolyl)butyl)oxy-6-methoxy-3-methyl-1,2,3,5-tetrahydroimidazo[2,1-b]quinazolin-2-one;
7-(5-(N-imidazolyl)pentyl)oxy-6-methoxy-3-methyl-1,2,3,5-tetrahydroimidazo[2,1-b]quinazolin-2-one;
7-(7-(N-imidazolyl)heptyl)oxy-6-methoxy-3-methyl-1,2,3,5-tetrahydroimidazo[2,1-b]quinazolin-2-one;
7-(8-(N-imidazolyl)octyl)oxy-6-methoxy-3-methyl-1,2,3,5-tetrahydroimidazo[2,1-b]quinazolin-2-one;
7-(2-(N-imidazolyl)ethyl)oxy-6-methoxy-3-hydroxymethyl-1,2,3,5-tetrahydroimidazo[2,1-b]quinazolin-2-one;
7-(3-(N-imidazolyl)propyl)oxy-6-methoxy-3-hydroxymethyl-1,2,3,5-tetrahydroimidazo[2,1-b]quinazolin-2-one;
7-(4-(N-imidazolyl)butyl)oxy-6-methoxy-3-hydroxymethyl-1,2,3,5-tetrahydroimidazo[2,1-b]quinazolin-2-one;
7-(5-(N-imidazolyl)pentyl)oxy-6-methoxy-3-hydroxymethyl-1,2,3,5-tetrahydroimidazo[2,1-b]quinazolin-2-one;
7-(7-(N-imidazolyl)heptyl)oxy-6-methoxy-3-hydroxymethyl-1,2,3,5-tetrahydroimidazo[2,1-b]quinazolin-2-one;
7-(8-(N-imidazolyl)octyl)oxy-6-methoxy-3-hydroxymethyl-1,2,3,5-tetrahydroimidazo[2,1-b]quinazolin-2-one;
7-(2-(N-imidazolyl)ethyl)oxy-6-methoxy-3-benzyl-1,2,3,5-tetrahydroimidazo[2,1-b]quinazolin-2-one;
7-(3-(N-imidazolyl)propyl)oxy-6-methoxy-3-benzyl-1,2,3,5-tetrahydroimidazo[2,1-b]quinazolin-2-one;
7-(4-(N-imidazolyl)butyl)oxy-6-methoxy-3-benzyl-1,2,3,5-tetrahydroimidazo[2,1-b]quinazolin-2-one;
7-(5-(N-imidazolyl)pentyl)oxy-6-methoxy-3-benzyl-1,2,3,5-tetrahydroimidazo[2,1-b]quinazolin-2-one;
7-(7-(N-imidazolyl)heptyl)oxy-6-methoxy-3-benzyl-1,2,3,5-tetrahydroimidazo[2,1-b]quinazolin-2-one;
7-(8-(N-imidazolyl)octyl)oxy-6-methoxy-3-benzyl-1,2,3,5-tetrahydroimidazo[2,1-b]quinazolin-2-one;
7-(2-(N-imidazolyl)ethyl)oxy-6-methoxy-3-phenyl-1,2,3,5-tetrahydroimidazo[2,1-b]quinazolin-2-one;
7-(3-(N-imidazolyl)propyl)oxy-6-methoxy-3-phenyl-1,2,3,5-tetrahydroimidazo[2,1-b]quinazolin-2-one;
7-(4-(N-imidazolyl)butyl)oxy-6-methoxy-3-phenyl-1,2,3,5-tetrahydroimidazo[2,1-b]quinazolin-2-one;
7-(5-(N-imidazolyl)pentyl)oxy-6-methoxy-3-phenyl-1,2,3,5-tetrahydroimidazo[2,1-b]quinazolin-2-one;
7-(7-(N-imidazolyl)heptyl)oxy-6-methoxy-3-phenyl-1,2,3,5-tetrahydroimidazo[2,1-b]quinazolin-2-one;

7-(8-(N-imidazolyl)octyl)oxy-6-methoxy-3-phenyl-1,2,3,5-tetrahydroimidazo[2,1-b]quinazolin-2-one;
7-(2-(N-imidazolyl)ethyl)oxy-6-methoxy-3-carbamoylmethyl-1,2,3,5-tetrahydroimidazo[2,1-b]quinazolin-2-one;
7-(3-(N-imidazolyl)propyl)oxy-6-methoxy-3-carbamoylmethyl-1,2,3,5-tetrahydroimidazo[2,1-b]quinazolin-2-one;
7-(4-(N-imidazolyl)butyl)oxy-6-methoxy-3-carbamoylmethyl-1,2,3,5-tetrahydroimidazo[2,1-b]quinazolin-2-one;
7-(5-(N-imidazolyl)pentyl)oxy-6-methoxy-3-carbamoylmethyl-1,2,3,5-tetrahydroimidazo[2,1-b]quinazolin-2-one;
7-(7-(N-imidazolyl)heptyl)oxy-6-methoxy-3-carbamoylmethyl-1,2,3,5-tetrahydroimidazo[2,1-b]quinazolin-2-one;
7-(8-(N-imidazolyl)octyl)oxy-6-methoxy-3-carbamoylmethyl-1,2,3,5-tetrahydroimidazo[2,1-b]quinazolin-2-one;
7-(2-(N-imidazolyl)ethyl)oxy-6-methoxy-3-carboxymethyl-1,2,3,5-tetrahydroimidazo[2,1-b]quinazolin-2-one;
7-(3-(N-imidazolyl)propyl)oxy-6-methoxy-3-carboxymethyl-1,2,3,5-tetrahydroimidazo[2,1-b]quinazolin-2-one;
7-(4-(N-imidazolyl)butyl)oxy-6-methoxy-3-carboxymethyl-1,2,3,5-tetrahydroimidazo[2,1-b]quinazolin-2-one;
7-(5-(N-imidazolyl)pentyl)oxy-6-methoxy-3-carboxymethyl-1,2,3,5-tetrahydroimidazo[2,1-b]quinazolin-2-one;
7-(7-(N-imidazolyl)heptyl)oxy-6-methoxy-3-carboxymethyl-1,2,3,5-tetrahydroimidazo[2,1-b]quinazolin-2-one;
7-(8-(N-imidazolyl)octyl)oxy-6-methoxy-3-carboxymethyl-1,2,3,5-tetrahydroimidazo[2,1-b]quinazolin-2-one;
7-(2-(N-imidazolyl)ethyl)oxy-6-methoxy-3-ethyl-1,2,3,5-tetrahydroimidazo[2,1-b]quinazolin-2-one;
7-(3-(N-imidazolyl)propyl)oxy-6-methoxy-3-ethyl-1,2,3,5-tetrahydroimidazo[2,1-b]quinazolin-2-one;
7-(4-(N-imidazolyl)butyl)oxy-6-methoxy-3-ethyl-1,2,3,5-tetrahydroimidazo[2,1-b]quinazolin-2-one;
7-(5-(N-imidazolyl)pentyl)oxy-6-methoxy-3-ethyl-1,2,3,5-tetrahydroimidazo[2,1-b]quinazolin-2-one;
7-(7-(N-imidazolyl)heptyl)oxy-6-methoxy-3-ethyl-1,2,3,5-tetrahydroimidazo[2,1-b]quinazolin-2-one;
7-(8-(N-imidazolyl)octyl)oxy-6-methoxy-3-ethyl-1,2,3,5-tetrahydroimidazo[2,1-b]quinazolin-2-one;
7-(2-(N-imidazolyl)ethyl)oxy-6-methoxy-3-isopropyl-1,2,3,5-tetrahydroimidazo[2,1-b]quinazolin-2-one;
7-(3-(N-imidazolyl)propyl)oxy-6-methoxy-3-isopropyl-1,2,3,5-tetrahydroimidazo[2,1-b]quinazolin-2-one;
7-(4-N-imidazolyl)butyl)oxy-6-methoxy-3-isopropyl-1,2,3,5-tetrahydroimidazo[2,1-b]quinazolin-2-one;
7-(5-(N-imidazolyl)pentyl)oxy-6-methoxy-3-isopropyl-1,2,3,5-tetrahydroimidazo[2,1-b]quinazolin-2-one;
7-(7-(N-imidazolyl)heptyl)oxy-6-methoxy-3-isopropyl-1,2,3,5-tetrahydroimidazo[2,1-b]quinazolin-2-one;
7-(8-(N-imidazolyl)octyl)oxy-6-methoxy-3-isopropyl-1,2,3,5-tetrahydroimidazo[2,1-b]quinazolin-2-one;
7-(2-(N-imidazolyl)ethyl)oxy-3-L-methyl-1,2,3,5-tetrahydroimidazo[2,1-b]quinazolin-2-one;
7-(3-(N-imidazolyl)propyl)oxy-3-L-methyl-1,2,3,5-tetrahydroimidazo[2,1-b]quinazolin-2-one;
7-(4-(N-imidazolyl)butyl)oxy-3-L-methyl-1,2,3,5-tetrahydroimidazo[2,1-b]quinazolin-2-one;
7-(5-(N-imidazolyl)pentyl)oxy-3-L-methyl-1,2,3,5-tetrahydroimidazo[2,1-b]quinazolin-2-one;
7-(7-(N-imidazolyl)heptyl)oxy-3-L-methyl-1,2,3,5-tetrahydroimidazo[2,1-b]quinazolin-2-one;
7-(8-(N-imidazolyl)octyl)oxy-3-L-methyl-1,2,3,5-tetrahydroimidazo[2,1-b]quinazolin-2-one;
7-(2-(N-imidazolyl)ethyl)oxy-3-L-hydroxymethyl-1,2,3,5-tetrahydroimidazo[2,1-b]quinazolin-2-one;
7-(3-(N-imidazolyl)propyl)oxy-3-L-hydroxymethyl-1,2,3,5-tetrahydroimidazo[2,1-b]quinazolin-2-one;
7-(4-(N-imidazolyl)butyl)oxy-3-L-hydroxymethyl-1,2,3,5-tetrahydroimidazo[2,1-b]quinazolin-2-one;
7-(5-(N-imidazolyl)pentyl)oxy-3-L-hydroxymethyl-1,2,3,5-tetrahydroimidazo[2,1-b]quinazolin-2-one;
7-(7-(N-imidazolyl)heptyl)oxy-3-L-hydroxymethyl-1,2,3,5-tetrahydroimidazo[2,1-b]quinazolin-2-one;
7-(8-(N-imidazolyl)octyl)oxy-3-L-hydroxymethyl-1,2,3,5-tetrahydroimidazo[2,1-b]quinazolin-2-one;
7-(2-(N-imidazolyl)ethyl)oxy-3-L-benzyl-1,2,3,5-tetrahydroimidazo[2,1-b]quinazolin-2-one;
7-(3-(N-imidazolyl)propyl)oxy-3-L-benzyl-1,2,3,5-tetrahydroimidazo[2,1-b]quinazolin-2-one;
7-(4-(N-imidazolyl)butyl)oxy-3-L-benzyl-1,2,3,5-tetrahydroimidazo[2,1-b]quinazolin-2-one;
7-(5-(N-imidazolyl)pentyl)oxy-3-L-benzyl-1,2,3,5-tetrahydroimidazo[2,1-b]quinazolin-2-one;
7-(7-(N-imidazolyl)heptyl)oxy-3-L-benzyl-1,2,3,5-tetrahydroimidazo[2,1-b]quinoazolin-2-one;
7-(8-(N-imidazolyl)octyl)oxy-3-L-benzyl-1,2,3,5-tetrahydroimidazo[2,1-b]quinazolin-2-one;
7-(2-(N-imidazolyl)ethyl)oxy-3-L-phenyl-1,2,3,5-tetrahydroimidazo[2,1-b]quinazolin-2-one;
7-(3-(N-imidazolyl)propyl)oxy-3-L-phenyl-1,2,3,5-tetrahydroimidazo[2,1-b]quinazolin-2-one;
7-(4-(N-imidazolyl)butyl)oxy-3-L-phenyl-1,2,3,5-tetrahydroimidazo[2,1-b]quinazolin-2-one;
7-(5-(N-imidazolyl)pentyl)oxy-3-L-phenyl-1,2,3,5-tetrahydroimidazo[2,1-b]quinazolin-2-one;
7-(7-(N-imidazolyl)heptyl)oxy-3-L-phenyl-1,2,3,5-tetrahydroimidazo[2,1-b]quinazolin-2-one;
7-(8-(N-imidazolyl)octyl)oxy-3-L-phenyl-1,2,3,5-tetrahydroimidazo[2,1-b]quinazolin-2-one;
7-(2-(N-imidazolyl)ethyl)oxy-3-L-carbamoylmethyl-1,2,3,5-tetrahydroimidazo[2,1-b]quinazolin-2-one;
7-(3-(N-imidazolyl)propyl)oxy-3-L-carbamoylmethyl-1,2,3,5-tetrahydroimidazo[2,1-b]quinazolin-2-one;
7-(4-(N-imidazolyl)butyl)oxy-3-L-carbamoylmethyl-1,2,3,5-tetrahydroimidazo[2,1-b]quinazolin-2-one;
7-(5-(N-imidazolyl)pentyl)oxy-3-L-carbamoylmethyl-1,2,3,5-tetrahydroimidazo[2,1-b]quinazolin-2-one;
7-(7-(N-imidazolyl)heptyl)oxy-3-L-carbamoylmethyl-1,2,3,5-tetrahydroimidazo[2,1-b]quinazolin-2-one;
7-(8-(N-imidazolyl)octyl)oxy-3-L-carbamoylmethyl-1,2,3,5-tetrahydroimidazo[2,1-b]quinazolin-2-one;
7-(2-(N-imidazolyl)ethyl)oxy-3-L-carboxymethyl-1,2,3,5-tetrahydroimidazo[2,1-b]quinazolin-2-one;
7-(3-(N-imidazolyl)propyl)oxy-3-L-carboxymethyl-1,2,3,5-tetrahydroimidazo[2,1-b]quinazolin-2-one;
7-(4-(N-imidazolyl)butyl)oxy-3-L-carboxymethyl-1,2,3,5-tetrahydroimidazo[2,1-b]quinazolin-2-one;
7-(5-(N-imidazolyl)pentyl)oxy-3-L-carboxymethyl-1,2,3,5-tetrahydroimidazo[2,1-b]quinazolin-2-one;
7-(7-(N-imidazolyl)heptyl)oxy-3-L-carboxymethyl-1,2,3,5-tetrahydroimidazo[2,1-b]quinazolin-2-one;
7-(8-(N-imidazolyl)octyl)oxy-3-L-carboxymethyl-1,2,3,5-tetrahydroimidazo[2,1-b]quinazolin-2-one;
7-(2-(N-imidazolyl)ethyl)oxy-3L-ethyl-1,2,3,5-tetrahydroimidazo[2,1-b]quinazoline-2-one;

7-(3-(N-imidazolyl)propyl)oxy-3-L-ethyl-1,2,3,5-tetrahydroimidazo[2,1-b]quinazolin-2-one;
7-(4-(N-imidazolyl)butyl)oxy-3-L-ethyl-1,2,3,5-tetrahydroimidazo[2,1-b]quinazolin-2-one;
7-(5-(N-imidazolyl)pentyl)oxy-3-L-ethyl-1,2,3,5-tetrahydroimidazo[2,1-b]quinazolin-2-one;
7-(7-(N-imidazolyl)heptyl)oxy-3-L-ethyl-1,2,3,5-tetrahydroimidazo[2,1-b]quinazolin-2-one;
7-(8-(N-imidazolyl)octyl)oxy-3-L-ethyl-1,2,3,5-tetrahydroimidazo[2,1-b]quinazolin-2-one;
7-(2-(N-imidazolyl)ethyl)oxy-3-L-isopropyl-1,2,3,5-tetrahydroimidazo[2,1-b]quinazolin-2-one;
7-(3-(N-imidazolyl)propyl)oxy-3-L-isopropyl-1,2,3,5-tetrahydroimidazo[2,1-b]quinazolin-2-one;
7-(4-(N-imidazolyl)butyl)oxy-3-L-isopropyl-1,2,3,5-tetrahydroimidazo[2,1-b]quinazolin-2-one;
7-(5-(N-imidazolyl)pentyl)oxy-3-L-isopropyl-1,2,3,5-tetrahydroimidazo[2,1-b]quinazolin-2-one;
7-(7-(N-imidazolyl)heptyl)oxy-3-l-isopropyl-1,2,3,5-tetrahydroimidazo[2,1-b]quinazolin-2-one;
7-(8-(N-imidazolyl)octyl)oxy-3-L-isopropyl-1,2,3,5-tetrahydroimidazo[2,1-b]quinazolin-2-one; or
7-(2-(N-imidazolyl)ethyl)oxy-3-D-methyl-1,2,3,5-tetrahydroimidazo[2,1-b]quinazolin-2-one;
7-(3-(N-imidazolyl)propyl)oxy-3-D-methyl-1,2,3,5-tetrahydroimidazo[2,1-b]quinazolin-2-one;
7-(4-(N-imidazolyl)butyl)oxy-3-D-methyl-1,2,3,5-tetrahydroimidazo[2,1-b]quinazolin-2-one;
7-(5-(N-imidazolyl)pentyl)oxy-3-D-methyl-1,2,3,5-tetrahydroimidazo[2,1-b]quinazolin-2-one;
7-(7-(N-imidazolyl)heptyl)oxy-3-D-methyl-1,2,3,5-tetrahydroimidazo[2,1-b]quinazolin-2-one;
7-(8-(N-imidazolyl)octyl)oxy-3-D-methyl-1,2,3,5-tetrahydroimidazo[2,1-b]quinazolin-2-one;
7-(2-(N-imidazolyl)ethyl)oxy-3-D-hydroxymethyl-1,2,3,5-etrahydroimidazo[2,1-b]quinazolin-2-one;
7-(3-(N-imidazolyl)propyl)oxy-3-D-hydroxymethyl-1,2,3,5-tetrahydroimidazo[2,1-b]quinazolin-2-one;
7-(4-(N-imidazolyl)butyl)oxy-3-D-hydroxymethyl-1,2,3,5-tetrahydroimidazo[2,1-b]quinazolin-2-one;
7-(5-(N-imidazolyl)pentyl)oxy-3-D-hydroxymethyl-1,2,3,5-tetrahydroimidazo[2,1-b]quinazolin-2-one;
7-(7-(N-imidazolyl)heptyl)oxy-3-D-hydroxymethyl-1,2,3,5-tetrahydroimidazo[2,1-b]quinazolin-2-one;
7-(8-(N-imidazolyl)octyl)oxy-3-D-hydroxymethyl-1,2,3,5-tetrahydroimidazo[2,1-b]quinazolin-2-one;
7-(2-(N-imidazolyl)ethyl)oxy-3-D-benzyl-1,2,3,5-tetrahydroimidazo[2,1-b]quinazolin-2-one;
7-(3-(N-imidazolyl)propyl)oxy-3-D-benzyl-1,2,3,5-tetrahydroimidazo[2,1-b]quinazolin-2-one;
7-(4-(N-imidazolyl)butyl)oxy-3-D-benzyl-1,2,3,5-tetrahydroimidazo[2,1-b]quinazolin-2-one;
7-(5-(N-imidazolyl)pentyl)oxy-3-D-benzyl-1,2,3,5-tetrahydroimidazo[2,1-b]quinazolin-2-one;
7-(7-(N-imidazolyl)heptyl)oxy-3-D-benzyl-1,2,3,5-tetrahydroimidazo[2,1-b]quinazolin-2-one;
7-(8-(N-imidazolyl)octyl)oxy-3-D-benzyl-1,2,3,5-tetrahydroimidazo[2,1-b]quinazolin-2-one;
7-(2-(N-imidazolyl)ethyl)oxy-3-D-phenyl-1,2,3,5-tetrahydroimidazo[2,1-b]quinazolin-2-one;
7-(3-(N-imidazolyl)propyl)oxy-3-D-phenyl-1,2,3,5-tetrahydroimidazo[2,1-b]quinazolin-2-one;
7-(4-(N-imidazolyl)butyl)oxy-3-D-pheny-1,2,3,5-tetrahydroimidazo[2,1-b]quinazolin-2-one;
7-(5-(N-imidazolyl)pentyl)oxy-3-D-phenyl-1,2,3,5-tetrahydroimidazo[2,1-b]quinazolin-2-one;
7-(7-(N-imidazolyl)heptyl)oxy-3-D-phenyl-1,2,3,5-tetrahydroimidazo[2,1-b]quinazolin-2-one;
7-(8-(N-imidazolyl)octyl)oxy-3-D-phenyl-1,2,3,5-tetrahydroimidazo[2,1-b]quinazolin-2-one;
7-(2-(N-imidazolyl)ethyl)oxy-3-D-carbamoylmethyl-1,2,3,5-tetrahydroimidazo[2,1-b]quinazolin-2-one;
7-(3-(N-imidazolyl)propyl)oxy-3-D-carbamoylmethyl-1,2,3,5-tetrahydroimidazo[2,1-b]quinazolin-2-one;
7-(4-(N-imidazolyl)butyl)oxy-3-D-carbamoylmethyl-1,2,3,5-tetrahydroimidazo[2,1-b]quinazolin-2-one;
7-(5-(N-imidazolyl)pentyl)oxy-3-D-carbamoylmethyl-1,2,3,5-tetrahydroimidazo[2,1-b]quinazolin-2-one;
7-(7-(N-imidazolyl)heptyl)oxy-3-D-carbamoylmethyl-1,2,3,5-tetrahydroimidazo[2,1-b]quinazolin-2-one;
7-(8-(N-imidazolyl)octyl)oxy-3-D-carbamoylmethyl-1,2,3,5-tetrahydroimidazo[2,1-b]quinazolin-2-one;
7-(2-(N-imidazolyl)ethyl)oxy-3-D-carboxymethyl-1,2,3,5-tetrahydroimidazo[2,1-b]quinazolin-2-one;
7-(3-(N-imidazolyl)propyl)oxy-3-D-carboxymethyl-1,2,3,5-tetrahydroimidazo[2,1-b]quinazolin-2-one;
7-(4-(N-imidazolyl)butyl)oxy-3-D-carboxymethyl-1,2,3,5-tetrahydroimidazo[2,1-b]quinazolin-2-one;
7-(5-(N-imidazolyl)pentyl)oxy-3-D-carboxymethyl-1,2,3,5-tetrahydroimidazo[2,1-b]quinazolin-2-one;
7-(7-(N-imidazolyl)heptyl)oxy-3-D-carboxymethyl-1,2,3,5-tetrahydroimidazo[2,1-b]quinazolin-2-one;
7-(8-(N-imidazolyl)octyl)oxy-3-D-carboxymethyl-1,2,3,5-tetrahydroimidazo[2,1-b]quinazolin-2-one;
7-(2-(N-imidazolyl)ethyl)oxy-3-D-ethyl-1,2,3,5-tetrahydroimidazo[2,1-b]quinazolin-2-one;
7-(3-(N-imidazolyl)propyl)oxy-3-D-ethyl-1,2,3,5-tetrahydroimidazo[2,1-b]quinazolin-2-one;
7-(4-(N-imidazolyl)butyl)oxy-3-D-ethyl-1,2,3,5-tetrahydroimidazo[2,1-b]quinazolin-2-one;
7-(5-(N-imidazolyl)pentyl)oxy-3-D-ethyl-1,2,3,5-tetrahydroimidazo[2,1-b]quinazolin-2-one;
7-(7-(N-imidazolyl)heptyl)oxy-3-D-ethyl-1,2,3,5-tetrahydroimidazo[2,1-b]quinazolin-2-one;
7-(8-(N-imidazolyl)octyl)oxy-3-D-ethyl-1,2,3,5-tetrahydroimidazo[2,1-b]quinazolin-2-one;
7-(2-(N-imidazolyl)ethyl)oxy-3-D-isopropyl-1,2,3,5-tetrahydroimidazo[2,1-b]quinazolin-2-one;
7-(3-(N-imidazolyl)propyl)oxy-3-D-isopropyl-1,2,3,5-tetrahydroimidazo[2,1-b]quinazolin-2-one;
7-(4-(N-imidazolyl)butyl)oxy-3-D-isopropyl-1,2,3,5-tetrahydroimidazo[2,1-b]quinazolin-2-one;
7-(5-(N-imidazolyl)pentyl)oxy-3-D-isopropyl-1,2,3,5-tetrahydroimidazo[2,1-b]quinazolin-2-one;
7-(7-(N-imidazolyl)heptyl)oxy-3-D-isopropyl-1,2,3,5-tetrahydroimidazo[2,1-b]quinazolin-2-one;
7-(8-(N-imidazolyl)octyl)oxy-3-D-iospropyl-1,2,3,5-tetrahydroimidazo[2,1-b]quinazolin-2-one; and
others.

Examples 6-10 illustrate the alternate pathway of preparation of compound I.

EXAMPLE 6

Preparation of Chloroalkyl-p-Toluenesulfonate

This example illustrates the preparation of various chloroalkyl-p-toluenesulfonates according to the method of Gensler, et al., *J. Org. Chem.*, 44, 3643 (1979)

I. Preparation of 6-Chlorohexyl-p-Toluenesulfonate

A solution of 6-chloro-1-hexanol (100 g) in dry pyridine (500 ml) was treated with p-toluenesulfonyl chloride (227 g) at 5°-10° C. After stirring 2 h at 10° C., the mixture was poured into ice water (2 L), followed by extraction with ethyl ether. The organic extract was washed with ice water and brine, dried, filtered and evaporated to give a syrup, which was further dried at high vacuum. The crude product was overlayered with pentane and cooled in dry ice/acetone to give a solid (210 g, 99%), mp 36°–37° C.

II. Preparation of Other Chloroalkyl-p-Toluenesulfonates

Similarly, using the procedure of Example 6.I., but substituting 6-chloro-1-hexanol with:
2-chloro-1-ethanol;
3-chloro-1-propanol;
4-chloro-1-butanol;
5-chloro-1-pentanol;
7-chloro-1-heptanol;
8-chloro-1-octanol; one obtains, respectively:
2-chloroethyl-p-toluenesulfonate;
3-chloropropyl-p-toluenesulfonate;
4-chlorobutyl-p-toluenesulfonate;
5-chloropentyl-p-toluenesulfonate;
7-chloroheptyl-p-toluenesulfonate;
8-chlorooctyl-p-toluenesulfonate.

EXAMPLE 7

Preparation of 5-(X-Chloroalkyl)oxy-2-Nitrobenzaldehydes

This example illustrates the preparation of various 5-(X-chloroalkyl)oxy-2-nitrobenzaldehydes wherein x is an integer of 2–8 and depends on the length of the alkyl chain.

I. Preparation of 5-(6-Chlorohexyl)oxy-2-Nitrobenzaldehyde a. A mixture of 16.7 g (100 mmol) of 5-hydroxy-2-nitrobenzaldehyde, 32 g (110 mmol) of 6-chlorohexyl-p-toluenesulfonate and 17 g of potassium carbonate in dry 250 ml of DMF was heated to 100° C. under dry nitrogen for 3 h. The reaction was cooled, filtered and evaporated to a dark oil. The crude product was dissolved in 500 ml of ethyl acetate, and the organic layer was washed twice with 300 ml of saturated sodium carbonate, and twice with 300 ml of brine, dried, filtered and evaporated. Filtration through silica gel gave 25.5 g (89.2 mmol, 89%) of 5-(6-chlorohexyl)oxy-2-nitrobenzaldehyde as a green syrup unstable to distillation.

For compounds wherein n is 1, commercially available chloroiodomethane is substituted for the required tosylate.

b. Compounds which are attached to the ring in another than 7 position, can be prepared by substituting 5-hydroxy-2-nitrobenzaldehyde with 6-hydroxy-2-nitrobenzaldehyde for compounds attached at position 6, with 4-hydroxy-2-nitrobenzaldehyde for compounds attached at position 8, with 3-hydroxy-2-nitrobenzaldehyde for compounds attached at position 9.

II. Preparation of Various Other 5-(6-Chlorohexyl)oxy-2-Nitrobenzaldehydes

Similarly, by using the procedure of Example 7.I. but substituting 6-chlorohexyl-p-toluenesulfonate with compounds obtained in Example 6.II., one obtains, respectively:
5-(1-chloromethyl)oxy-2-nitrobenzaldehyde;
5-(2-chloroethyl)oxy-2-nitrobenzaldehyde;
5-(3-chloropropyl)oxy-2-nitrobenzaldehyde;
5-(4-chlorbutyl)oxy-2-nitrobenzaldehyde;
5-(5-chloropentyl)oxy-2-nitrobenzaldehyde;
5-(7-chloroheptyl)oxy-2-nitrobenzaldehyde;
5-(8-chlorooctyl)oxy-2-nitrobenzaldehyde;

EXAMPLE 8

I. Protection of Aldehyde Moiety

A solution of 25.7 g (90 mmol) of aldehyde from Example 7, 17.2 ml (180 mmol) of 2-methoxy-1,3-dioxolane and 2.10 g (9 mmol) of camphor-10-sulfonic acid in 100 ml of toluene was heated at 80° C. overnight. After cooling, the mixture was washed twice with 50 ml of saturated sodium bicarbonate, twice with 50 ml of brine, dried, filtered and evaporated at high vacuum to give 28.0 g (85 mmol, 89%) of chloroacetal compound with protected aldehyde moiety as an undistillable syrup.

II. All other compounds obtained in Example 7.II. can be similarly protected to give their respective chloroacetals.

EXAMPLE 9

Preparation of 5-(X-(N-Imidazolyl)Alkyl)oxy-2-Nitrobenzaldehydes

This example illustrates the preparation of various 5-(X-(N-imidazolyl)alkyl)oxy-2-nitrobenzaldehydes. X is an integer of 1–8 and depends on the length of the alkyl chain which can have 1–8 carbon atoms.

I. Preparation of 5-(6-(N-Imidazolyl)Hexyl)oxy-2-Nitrobenzaldehyde

A solution of 16.5 g (90 mmol) of chloroacetal from Example 8.I. in dry 50 ml of DMF was added dropwise to a chilled clear solution produced from 3.74 g (55 mmol) of imidazole and 1.32 g (55 mmol) of washed sodium hydride in dry 200 ml of DMF. The mixture was stirred at room temperature for 1 h, then the DMF was evaporated. The residue was dissolved in 100 ml of wet acetone and to it was added 1.26 g (5 mmol) of pyridinium p-toluenesulfonate. The mixture was heated at reflux overnight. After cooling and evaporation of the solvent, the residue was dissolved in 200 ml of ethyl acetate, and was washed twice with 100 ml of saturated aqueous sodium bicarbonate, twice with 100 ml of brine, dried, filtered and evaporated to give 16.2 g (45 mmol, 90%) of 5-(6-N-imidazolyl)hexyl)oxy-2-nitrobenzaldehyde as a syrup after filtration through sillica gel.

II. Preparation of Various Other 5-(6-(N-Imidazolyl)Hexyl)oxy-2-Nitrobenzaldehyde Similarly, by using the procedure of Example 9.I., but substituting the chloroacetal obtained in Example 8.I. with chloroacetal obtained in Example 8.II., one can obtain, respectively:
5-(1-(N-imidazolyl)methyl)oxy-2-nitrobenzaldehyde;
5-(2-(N-imidazolyl)ethyl)oxy-2-nitrobenzaldehyde;
5-(3-(N-imidazolyl)propyl)oxy-2-nitrobenzaldehyde;
5-(4-(N-imidazolyl)butyl)oxy-2-nitrobenzaldehyde;
5-(5-(N-imidazolyl)pentyl)oxy-2-nitrobenzaldehyde;
5-(7-(N-imidazolyl)heptyl)oxy-2-nitrobenzaldehyde;
5-(8-(N-imidazolyl)octyl)oxy-2-nitrobenzaldehyde.

EXAMPLE 10

Preparation of 7-(X-(N-Imidazolyl)Alkyl)oxy-1,2,3,5-Tetrahydroimidazo[2,1-b]quinazolin-2-one This example illustrates the preparation of various 7-(x-(N-imidazolyl)alkyl)oxy-1,2,3,5-tetrahydroimidazo[2,1-b]quinazolin-2-ones wherein x is an integer of 1-8 and depends on the carbon chain length of alkyl.

I. Preparation of 7-(6-(N-Imidazolyl)Hexyl)oxy-1,2,3,5-Tetrahydroimidazo[2,1-b]quinazolin-2-one 65.6 g (800 mmol) of sodium acetate was added to a warm solution of 139 g (1 mole) of glycine ethyl ester hydrochloride in 500 ml of absolute ethanol. Upon cooling, the resulting precipitate of sodium chloride was removed, and to the supernatant was added 36.1 g (100 mmol) of 5-(6-(N-imidazolyl)hexyl)oxy-2-nitrobenzaldehyde and 50 g of molecular sieves. After 30 min, 3.8 g (50 mmol) of sodium cyanoborohydride was added, and the mixture was allowed to stir at room temperature for 3–4 h. The reaction solution was then filtered to remove precipitated solids and molecular sieves, and the methanol was removed by evaporation. The residue was dissolved in 300 ml of ethyl acetate and was washed twice with 100 ml of saturated sodium bicarbonate and twice with 100 ml of brine. The organic extract was dried, filtered and evaporated to give a thick syrup. Owing to the instability of the oil, the crude product was used directly.

The thick syrupy residue from above was dissolved in absolute ethanol (200 ml) and hydrogenated over 10% Pd-C (5.0 g) until uptake of the hydrogen ceased, approximately 4 h. The catalyst was removed by filtration through a pad of Celite, and pad was washed clean with absolute ethanol (50 ml).

The combined filtrates from the previous paragraph were treated with cyanogen bromide (11./7 g, 110 mmol), and the resulting solution was stirred at room temperature for 16 h, and was then treated with ammonium hydroxide (50 ml) and stirred for 2 h at room temperature. The product precipitated from this mixture as an off-white to tan powder. The powder was further purified by filtration and a water wash and dried, yielding the title compound (11.3 g, 32 mmol, 32%), mp 188°–189° C.

II.a. Preparation of Other 7-(X-(N-Imidazolyl)Alkyl)oxy-$R_3$-1,2,3,5-Tetrahydroimidazo[2,1-b]quinazolin-2-ones This section illustrates the preparation of compounds wherein $R_3$ is amino acid side chain. Thus, in this preparation, glycine ethyl ester hydrochloride is substituted with other α-amino acid alkyl ester hydrochloride, and such substitution determines $R_3$ of the final product. The non-exclusive examples of such α-amino acids substituting glycine are alanine, serine, phenylalanine, phenylglycine, asparagine, aspartic acid, aminobutyric acid, and valine but others may also be used.

Also, the use of optically active α-amino acid will result in optically active $R_3$ amino acid residue in the final product and thus will ultimately determine the optical activity of the final compound.

By substituting glycine ethyl ester hydrochloride with alanine, serine, phenylalanine, phenylglycine, asparagine, aspartic acid, aminobutyric acid, valine and other amino acid ethyl ester hydrochlorides, one obtains respectively:

7-(6-(N-imidazolyl)hexyl)oxy-3-methyl-1,2,3,5-tetrahydroimidazo[2,1-b]quinazolin-2-one;

7-(6-(N-imidazolyl)hexyl)oxy-3-hydroxymethyl-1,2,3,5-tetrahydroimidazo[2,1-b]quinazolin-2-one;

7-(6-(N-imidazolyl)hexyl)oxy-3-benzyl-1,2,3,5-tetrahydroimidazo[2,1-b]quinazolin-2-one;

7-(6-(N-imidazolyl)hexyl)oxy-3-phenyl-1,2,3,5-tetrahydroimidazo[2,1-b]quinazolin-2-one;

7-(6-(N-imidazolyl)hexyl)oxy-3-carbamoylmethyl-1,2,3,5-tetrahydroimidazo[2,1-b]quinazolin-2-one;

7-(6-(N-imidazolyl)hexyl)oxy-3-carboxymethyl-1,2,3,5-tetrahydroimidazo[2,1-b]quinazolin-2-one;

7-(6-(N-imidazolyl)hexyl)oxy-3-ethyl-1,2,3,5-tetrahydroimidazo[2,1-b]quinazolin-2-one;

7-(6-(N-imidazolyl)hexyl)oxy-3-isopropyl-1,2,3,5-tetrahydroimidazo[2,1-b]quinazolin-2-one;

7-(6-(N-imidazolyl)hexyl)oxy-6-chloro-3-methyl-1,2,3,5-tetrahydroimidazo[2,1-b]quinazolin-2-one;

7-(6-(N-imidazolyl)hexyl)oxy-6-chloro-3-hydroxymethyl-1,2,3,5-tetrahydroimidazo[2,1-b]quinazolin-2-one;

7-(6-(N-imidazolyl)hexyl)oxy-6-chloro-3-benzyl-1,2,3,5-tetrahydroimidazo[2,1-b]quinazolin-2-one;

7-(6-(N-imidazolyl)hexyl)oxy-6-chloro-3-phenyl-1,2,3,5-tetrahydroimidazo[2,1-b]quinazolin-2-one;

7-(6-(N-imidazolyl)hexyl)oxy-6-chloro-3-carbamoylmethyl-1,2,3,5-tetrahydroimidazo[2,1-b]quinazolin-2-one;

7-(6-(N-imidazolyl)hexyl)oxy-6-chloro-3-carboxymethyl-1,2,3,5-tetrahydroimidazo[2,1-b]quinazolin-2-one;

7-(6-(N-imidazolyl)hexyl)oxy-6-chloro-3-ethyl-1,2,3,5-tetrahydroimidazo[2,1-b]quinazolin-2-one;

7-(6-(N-imidazolyl)hexyl)oxy-6-chloro-3-isopropyl-1,2,3,5-tetrahydroimidazo[2,1-b]quinazolin-2-one;

7-(6-(N-imidazolyl)hexyl)oxy-6-methoxy-3-methyl-1,2,3,5-tetrahydroimidazo[2,1-b]quinazolin-2-one;

7-(6-(N-imidazolyl)hexyl)oxy-6-methoxy-3-hydroxymethyl-1,2,3,5-tetrahydroimidazo[2,1-b]quinazolin-2-one;

7-(6-(N-imidazolyl)hexyl)oxy-6-methoxy-3-benzyl-1,2,3,5-tetrahydroimidazo[2,1-b]quinazolin-2-one;

7-(6-(N-imidazolyl)hexyl)oxy-6-methoxy-3-phenyl-1,2,3,5-tetrahydroimidazo[2,1-b]quinazolin-2-one;

7-(6-(N-imidazolyl)hexyl)oxy-6-methoxy-3-carbamoylmethyl-1,2,3,5-tetrahydroimidazo[2,1-b]quinazolin-2-one;

7-(6-(N-imidazolyl)hexyl)oxy-6-methoxy-3-carboxymethyl-1,2,3,5-tetrahydroimidazo[2,1-b]quinazolin-2-one;

7-(6-(N-imidazolyl)hexyl)oxy-6-methoxy-3-ethyl-1,2,3,5-tetrahydroimidazo[2,1-b]quinazolin-2-one;

7-(6-(N-imidazolyl)hexyl)oxy-6-methoxy-3-isopropyl-1,2,3,5-tetrahydroimidazo[2,1-b]quinazolin-2-one;

7-(6-(N-imidazolyl)hexyl)oxy-3-L-methyl-1,2,3,5-tetrahydroimidazo[2,1-b]quinazolin-2-one;

7-(6-(N-imidazolyl)hexyl)oxy-3-L-hydroxymethyl-1,2,3,5-tetrahydroimidazo[2,1-b]quinazolin-2-one;

7-(6-(N-imidazolyl)hexyl)oxy-3-L-benzyl-1,2,3,5-tetrahydroimidazo[2,1-b]quinazolin-2-one;

7-(6-(N-imidazolyl)hexyl)oxy-3-L-phenyl-1,2,3,5-tetrahydroimidazo[2,1-b]quinazolin-2-one;

7-(6-(N-imidazolyl)hexyl)oxy-3-L-carbamoylmethyl-1,2,3,5-tetrahydroimidazo[2,1-b]quinazolin-2-one;

7-(6-(N-imidazolyl)hexyl)oxy-3-L-carboxymethyl-1,2,3,5-tetrahydroimidazo[2,1-b]quinazolin-2-one;

7-(6-(N-imidazolyl)hexyl)oxy-3-L-ethyl-1,2,3,5-tetrahydroimidazo[2,1-b]quinazolin-2-one;

7-(6-(N-imidazolyl)hexyl)oxy-3-L-isopropyl-1,2,3,5-tetrahydroimidazo[2,1-b]quinazolin-2-one; or 7-(6-(N-imidazolyl)hexyl)oxy-3-D-methyl-1,2,3,5-tetrahydroimidazo[2,1-b]quinazolin-2-one;

7-(6-(N-imidazolyl)hexyl)oxy-3-D-hydroxymethyl-1,2,3,5-tetrahydroimidazo[2,1-b]quinazolin-2-one;

7-(6-(N-imidazolyl)hexyl)oxy-3-D-benzyl-1,2,3,5-tetrahydroimidazo[2,1-b]quinazolin-2-one;

7-(6-(N-imidazolyl)hexyl)oxy-3-D-phenyl-1,2,3,5-tetrahydroimidazo[2,1-b]quinazolin-2-one;
7-(6-(N-imidazolyl)hexyl)oxy-3-D-carbamoylmethyl-1,2,3,5-tetrahydroimidazo[2,1-b]quinazolin-2-one;
7-(6-(N-imidazolyl)hexyl)oxy-3-D-carboxymethyl-1,2,3,5-tetrahydroimidazo[2,1-b]quinazolin-2-one;
7-(6-(N-imidazolyl)hexyl)oxy-3-D-ethyl-1,2,3,5-tetrahydroimidazo[2,1-b]quinazolin-2-one;
7-(6-(N-imidazolyl)hexyl)oxy-3-D-isopropyl-1,2,3,5-tetrahydroimidazo[2,1-b]quinazolin-2-one;
and others.

II. b. Preparation of Other 7-(X-(N-Imidazolyl)alkyl)oxy-1,2,3,5-tetrahydroimidazo[2,1-b]quinazolin-2-one The other 7-(x-(N-imidazolyl)alkyl)oxy-1,2,3,5-tetrahydroimidazo[2,1-b]quinazolin-2-ones wherein $R_3$ is hydrogen can be prepared by substituting 5-(6-(N-imidazolyl)hexyl)oxy-2-nitrobenzalhyde with compounds of Example 2. II. to give:

7-(2-(N-imidazolyl)ethyl)oxy-1,2,3,5-tetrahydroimidazo[2,1-b]quinazolin-2-one;
7-(3-(N-imidazolyl)propyl)oxy-1,2,3,5-tetrahydroimidazo[2,1-b]quinazolin-2-one;
7-(4-(N-imidazolyl)butyl)oxy-1,2,3,5-tetrahydroimidazo-[2,1-b]quinazolin-2-one;
7-(5-(N-imidazolyl)pentyl)oxy-1,2,3,5-tetrahydroimidazo[2,1-b]quinazolin-2-one;
7-(7-(N-imidazolyl)heptyl)oxy-1,2,3,5-tetrahydroimidazo[2,1-b]quinazolin-2-one; and
7-(8-(N-imidazolyl)octyl)oxy-1,2,3,5-tetrahydroimidazo[2,1-b]quinazolin-2-one.

II. c. Preparation of Other 7-(6-Acetoxyalkyl)oxy-$R_3$-1,2,3,5-tetrahydroimidazo[2,1-b]quinazolin-2-ones Similarly, using the procedure of Section II.a. of This Example 10 but substituting 5-(6-(N-imidazolyl)hexyl)oxy-2-nitrobenzaldehyde with any compound obtained in Section II.a and alkyl obtained in Section II.b., one can obtain 7-(x-(N-imidazolyl)alkyl)oxy-$R_3$-substituted-1,2,3,5-tetrahydroimidazo[2,1-b]-quinazolin-2-ones wherein x is an integer of 2–8 and depends on the length of alkyl chain. $R_3$ is as designated in Summary. In this way one can obtain, respectively:

7-(2-(N-imidazolyl)ethyl)oxy-3-methyl-1,2,3,5-tetrahydroimidazo[2,1-b]quinazolin-2-one;
7-(2-(N-imidazolyl)ethyl)oxy-3-hydroxymethyl-1,2,3,5-tetrahydroimidazo[2,1-b]quinazolin-2-one;
7-(2-(N-imidazolyl)ethyl)oxy-3-benzyl-1,2,3,5-tetrahydroimidazo[2,1-b]quinazolin-2-one;
7-(2-(N-imidazolyl)ethyl)oxy-3-phenyl-1,2,3,5-tetrahydroimidazo[2,1-b]quinazolin-2-one;
7-(2-(N-imidazolyl)ethyl)oxy-3-carbamoylmethyl-1,2,3,5-tetrahydroimidazo[2,1-b]quinazolin-2-one;
7-(2-(N-imidazolyl)ethyl)oxy-3-carboxymethyl-1,2,3,5-tetrahydroimidazo[2,1-b]quinazolin-2-one;
7-(2-(N-imidazolyl)ethyl)oxy-3-ethyl-1,2,3,5-tetrahydroimidazo[2,1-b]quinazolin-2-one;
7-(2-(N-imidazolyl)ethyl)oxy-3-isopropyl-1,2,3,5-tetrahydroimidazo[2,1-b]quinazolin-2-one;
7-(3-(N-imidazolyl)propyl)oxy-3-methyl-1,2,3,5-tetrahydroimidazo[2,1-b]quinazolin-2-one;
7-(3-(N-imidazolyl)propyl)oxy-3-hydroxymethyl-1,2,3,5-tetrahydroimidazo[2,1-b]quinazolin-2-one;
7-(3-(N-imidazolyl)propyl)oxy-3-benzyl-1,2,3,5-tetrahydroimidazo[2,1-b]quinazolin-2-one;
7-(3-(N-imidazolyl)propyl)oxy-3-phenyl-1,2,3,5-tetrahydroimidazo[2,1-b]quinazolin-2-one;
7-(3-(N-imidazolyl)propyl)oxy-3-carbamoylmethyl-1,2,3,5-tetrahydroimidazo[2,1-b]quinazolin-2-one;
7-(3-(N-imidazolyl)propyl)oxy-3-ethyl-1,2,3,5-tetrahydroimidazo[2,1-b]quinazolin-2-one;
7-(3-(N-imidazolyl)propyl)oxy-3-isopropyl-1,2,3,5-tetrahydroimidazo[2,1-b]quinazolin-2-one;
7-(4-(N-imidazolyl)butyl)oxy-3-methyl-1,2,3,5-tetrahydroimidazo[2,1-b]quinazolin-2-one;
7-(4-(N-imidazolyl)butyl)oxy-3-hydroxymethyl-1,2,3,5-tetrahydroimidazo[2,1-b]quinazolin-2-one;
7-(4-(N-imidazolyl)butyl)oxy-3-benzyl-1,2,3,5-tetrahydroimidazo[2,1-b]quinazolin-2-one;
7-(4-(N-imidazolyl)butyl)oxy-3-phenyl-1,2,3,5-tetrahydroimidazo[2,1-b]quinazolin-2-one;
7-(4-(N-imidazolyl)butyl)oxy-3-carbamoylmethyl-1,2,3,5-tetrahydroimidazo[2,1-b]quinazolin-2-one;
7-(4-(N-imidazolyl)butyl)oxy-3-carboxymethyl-1,2,3,5-tetrahydroimidazo[2,1-b]quinazolin-2-one;
7-(4-(N-imidazolyl)butyl)oxy-3-ethyl-1,2,3,5-tetrahydroimidazo[2,1-b]quinazolin-2-one;
7-(4-(N-imidazolyl)butyl)oxy-3-isopropyl-1,2,3,5-tetrahydroimidazo[2,1-b]quinazolin-2-one;
7-(5-(N-imidazolyl)pentyl)oxy-3-methyl-1,2,3,5-tetrahydroimidazo[2,1-b]quinazolin-2-one;
7-(5-(N-imidazolyl)pentyl)oxy-3-hydroxymethyl-1,2,3,5-tetrahydroimidazo[2,1-b]quinazolin-2-one;
7-(5-(N-imidazolyl)pentyl)oxy-3-benzyl-1,2,3,5-tetrahydroimidazo[2,1-b]quinazolin-2-one;
7-(5-(N-imidazolyl)pentyl)oxy-3-phenyl-1,2,3,5-tetrahydroimidazo[2,1-b]quinazolin-2-one;
7-(5-(N-imidazolyl)pentyl)oxy-3-carbamoylmethyl-1,2,3,5-tetrahydroimidazo[2,1-b]quinazolin-2-one;
7-(5-(N-imidazolyl)pentyl)oxy-3-carboxymethyl-1,2,3,5-tetrahydroimidazo[2,1-b]quinazolin-2-one;
7-(5-(N-imidazolyl)pentyl)oxy-3-ethyl-1,2,3,5-tetrahydroimidazo[2,1-b]quinazolin-2-one;
7-(5-(N-imidazolyl)pentyl)oxy-3-isopropyl-1,2,3,5-tetrahydroimidazo[2,1-b]quinazolin-2-one;
7-(7-(N-imidazolyl)heptyl)oxy-3-methyl-1,2,3,5-tetrahydroimidazo[2,1-b]quinazolin-2-one;
7-(7-(N-imidazolyl)heptyl)oxy-3-hydroxymethyl-1,2,3,5-tetrahydroimidazo[2,1-b]quinazolin-2-one;
7-(7-(N-imidazolyl)heptyl)oxy-3-benzyl-1,2,3,5-tetrahydroimidazo[2,1-b]quinazolin-2-one;
7-(7-(N-imidazolyl)heptyl)oxy-3-phenyl-1,2,3,5-tetrahydroimidazo[2,1-b]quinazolin-2-one;
7-(7-(N-imidazolyl)heptyl)oxy-3-carbamoylmethyl-1,2,3,5-tetrahydroimidazo[2,1-b]quinazolin-2-one;
7-(7-(N-imidazolyl)heptyl)oxy-3-carboxymethyl-1,2,3,5-tetrahydroimidazo[2,1-b]quinazolin-2-one;
7-(7-(N-imidazolyl)heptyl)oxy-3-ethyl-1,2,3,5-tetrahydroimidazo[2,1-b]quinazolin-2-one;
7-(7-(N-imidazolyl)heptyl)oxy-3-isopropyl-1,2,3,5-tetrahydroimidazo[2,1-b]quinazolin-2-one;
7-(8-(N-imidazolyl)octyl)oxy-3-methyl-1,2,3,5-tetrahydroimidazo[2,1-b]quinazolin-2-one;
7-(8-(N-imidazolyl)octyl)oxy-3-hydroxymethyl-1,2,3,5-tetrahydroimidazo[2,1-b]quinazolin-2-one;
7-(8-(N-imidazolyl)octyl)oxy-3-benzyl-1,2,3,5-tetrahydroimidazo[2,1-b]quinazolin-2-one;
7-(8-(N-imidazolyl)octyl)oxy-3-phenyl-1,2,3,5-tetrahydroimidazo[2,1-b]quinazolin-2-one;
7-(8-(N-imidazolyl)octyl)oxy-3-carbamoylmethyl-1,2,3,5-tetrahydroimidazo[2,1-b]quinazolin-2-one;
7-(8-(N-imidazolyl)octyl)oxy-3-carboxymethyl-1,2,3,5-tetrahydroimidazo[2,1-b]quinazolin-2-one;

7-(8-(N-imidazolyl)octyl)oxy-3-ethyl-1,2,3,5-tetrahydroimidazo[2,1-b]quinazolin-2-one;

7-(8-(N-imidazolyl)octyl)oxy-3-isopropyl-1,2,3,5-tetrahydroimidazo[2,1-b]quinazolin-2-one;

7-(2-(N-imidazolyl)ethyl)oxy-6-chloro-3-methyl-1,2,3,5-tetrahydroimidazo[2,1-b]quinazolin-2-one;

7-(2-(N-imidazolyl)ethyl)oxy-6-chloro-3-hydroxymethyl-1,2,3,5-tetrahydroimidazo[2,1-b]quinazolin-2-one;

7-(2-(N-imidazolyl)ethyl)oxy-6-chloro-3-benzyl-1,2,3,5-tetrahydroimidazo[2,1-b]quinazolin-2-one;

7-(2-(N-imidazolyl)ethyl)oxy-6-chloro-3-phenyl-1,2,3,5-tetrahydroimidazo[2,1-b]quinazolin-2-one;

7-(2-(N-imidazolyl)ethyl)oxy-6-chloro-3-carbamoylmethyl-1,2,3,5-tetrahydroimidazo[2,1-b]quinazolin-2-one;

7-(2-(N-imidazolyl)ethyl)oxy-6-chloro-3-carboxymethyl-1,2,3,5-tetrahydroimidazo[2,1-b]quinazolin-2-one;

7-(2-(N-imidazolyl)ethyl)oxy-6-chloro-3-ethyl-1,2,3,5-tetrahydroimidazo[2,1-b]quinazolin-2-one;

7-(2-(N-imidazolyl)ethyl)oxy-6-chloro-3-isopropyl-1,2,3,5-tetrahydroimidazo[2,1-b]quinazolin-2-one;

7-(3-(N-imidazolyl)propyl)oxy-6-chloro-3-methyl-1,2,3,5-tetrahydroimidazo[2,1-b]quinazolin-2-one;

7-(3-(N-imidazolyl)propyl)oxy-6-chloro-3-hydroxymethyl-1,2,3,5-tetrahydroimidazo[2,1-b]quinazolin-2-one;

7-(3-(N-imidazolyl)propyl)oxy-6-chloro-3-benzyl-1,2,3,5-tetrahydroimidazo[2,1-b]quinazolin-2-one;

7-(3-(N-imidazolyl)propyl)oxy-6-chloro-3-phenyl-1,2,3,5-tetrahydroimidazo[2,1-b]quinazolin-2-one;

7-(3-(N-imidazolyl)propyl)oxy-6-chloro-3-carbamoylmethyl-1,2,3,5-tetrahydroimidazo[2,1-b]quinazolin-2-one;

7-(3-(N-imidazolyl)propyl)oxy-6-chloro-3-ethyl-1,2,3,5-tetrahydroimidazo[2,1-b]quinazolin-2-one;

7-(3-(N-imidazolyl)propyl)oxy-6-chloro-3-isopropyl-1,2,3,5-tetrahydroimidazo[2,1-b]quinazolin-2-one;

7-(4-(N-imidazolyl)butyl)oxy-6-chloro-3-methyl-1,2,3,5-tetrahydroimidazo[2,1-b]quinazolin-2-one;

7-(4-(N-imidazolyl)butyl)oxy-6-chloro-3-hydroxymethyl-1,2,3,5-tetrahydroimidazo[2,1-b]quinazolin-2-one;

7-(4-(N-imidazolyl)butyl)oxy-6-chloro-3-benzyl-1,2,3,5-tetrahydroimidazo[2,1-b]quinazolin-2-one;

7-(4-(N-imidazolyl)butyl)oxy-6-chloro-3-phenyl-1,2,3,5-tetrahydroimidazo[2,1-b]quinazolin-2-one;

7-(4-(N-imidazolyl)butyl)oxy-6-chloro-3-carbamoylmethyl-1,2,3,5-tetrahydroimidazo[2,1-b]quinazolin-2-one;

7-(4-(N-imidazolyl)butyl)oxy-6-chloro-3-carboxymethyl-1,2,3,5-tetrahydroimidazo[2,1-b]quinazolin-2-one;

7-(4-(N-imidazolyl)butyl)oxy-6-chloro-3-ethyl-1,2,3,5-tetrahydroimidazo[2,1-b]quinazolin-2-one;

7-(4-(N-imidazolyl)butyl)oxy-6-chloro-3-isopropyl-1,2,3,5-tetrahydroimidazo[2,1-b]quinazolin-2-one;

7-(5-(N-imidazolyl)pentyl)oxy-6-chloro-3-methyl-1,2,3,5-tetrahydroimidazo[2,1-b]quinazolin-2-one;

7-(5-(N-imidazolyl)pentyl)oxy-6-chloro-3-hydroxymethyl-1,2,3,5-tetrahydroimidazo[2,1-b]quinazolin-2-one;

7-(5-(N-imidazolyl)pentyl)oxy-6-chloro-3-benzyl-1,2,3,5-tetrahydroimidazo[2,1-b]quinazolin-2-one;

7-(5-(N-imidazolyl)pentyl)oxy-6-chloro-3-phenyl-1,2,3,5-tetrahydroimidazo[2,1-b]quinazolin-2-one;

7-(5-(N-imidazolyl)pentyl)oxy-6-chloro-3-carbamoylmethyl-1,2,3,5-tetrahydroimidazo[2,1-b]quinazolin-2-one;

7-(5-(N-imidazolyl)pentyl)oxy-6-chloro-3-carboxymethyl-1,2,3,5-tetrahydroimidazo[2,1-b]quinazolin-2-one;

7-(5-(N-imidazolyl)pentyl)oxy-6-chloro-3-ethyl-1,2,3,5-tetrahydroimidazo[2,1-b]quinazolin-2-one;

7-(5-(N-imidazolyl)pentyl)oxy-6-chloro-3-isopropyl-1,2,3,5-tetrahydroimidazo[2,1-b]quinazolin-2-one;

7-(7-(N-imidazolyl)heptyl)oxy-6-chloro-3-methyl-1,2,3,5-tetrahydroimidazo[2,1-b]quinazolin-2-one;

7-(7-(N-imidazolyl)heptyl)oxy-6-chloro-3-hydroxymethyl-1,2,3,5-tetrahydroimidazo[2,1-b]quinazolin-2-one;

7-(7-(N-imidazolyl)heptyl)oxy-6-chloro-3-benzyl-1,2,3,5-tetrahydroimidazo[2,1-b]quinazolin-2-one;

7-(7-(N-imidazolyl)heptyl)oxy-6-chloro-3-phenyl-1,2,3,5-tetrahydroimidazo[2,1-b]quinazolin-2-one;

7-(7-(N-imidazolyl)heptyl)oxy-6-chloro-3-carbamoylmethyl-1,2,3,5-tetrahydroimidazo[2,1-b]quinazolin-2-one;

7-(7-(N-imidazolyl)heptyl)oxy-6-chloro-3-carboxymethyl-1,2,3,5-tetrahydroimidazo[2,1-b]quinazolin-2-one;

7-(7-(N-imidazolyl)heptyl)oxy-6-chloro-3-ethyl-1,2,3,5-tetrahydroimidazo[2,1-b]quinazolin-2-one;

7-(7-(N-imidazolyl)heptyl)oxy-6-chloro-3-isopropyl-1,2,3,5-tetrahydroimidazo[2,1-b]quinazolin-2-one;

7-(8-(N-imidazolyl)octyl)oxy-6-chloro-3-methyl-1,2,3,5-tetrahydroimidazo[2,1-b]quinazolin-2-one;

7-(8-(N-imidazolyl)octyl)oxy-6-chloro-3-hydroxymethyl-1,2,3,5-tetrahydroimidazo[2,1-b]quinazolin-2-one;

7-(8-(N-imidazolyl)octyl)oxy-6-chloro-3-benzyl-1,2,3,5-tetrahydroimidazo[2,1-b]quinazolin-2-one;

7-(8-(N-imidazolyl)octyl)oxy-6-chloro-3-phenyl-1,2,3,5-tetrahydroimidazo[2,1-b]quinazolin-2-one;

7-(8-(N-imidazolyl)octyl)oxy-6-chloro-3-carbamoylmethyl-1,2,3,5-tetrahydroimidazo[2,1-b]quinazolin-2-one;

7-(8-(N-imidazolyl)octyl)oxy-6-chloro-3-carboxymethyl-1,2,3,5-tetrahydroimidazo[2,1-b]quinazolin-2-one;

7-(8-(N-imidazolyl)octyl)oxy-6-chloro-3-ethyl-1,2,3,5-tetrahydroimidazo[2,1-b]quinazolin-2-one;

7-(8-(N-imidazolyl)octyl)oxy-6-chloro-3-isopropyl-1,2,3,5-tetrahydroimidazo[2,1-b]quinazolin-2-one;

7-(2-(N-imidazolyl)ethyl)oxy-6-methoxy-3-methyl-1,2,3,5-tetrahydroimidazo[2,1-b]quinazolin-2-one;

7-(2-(N-imidazolyl)ethyl)oxy-6-methoxy-3-hydroxymethyl-1,2,3,5-tetrahydroimidazo[2,1-b]quinazolin-2-one;

7-(2-(N-imidazolyl)ethyl)oxy-6-methoxy-3-benzyl-1,2,3,5-tetrahydroimidazo[2,1-b]quinazolin-2-one;

7-(2-(N-imidazolyl)ethyl)oxy-6-methoxy-3-phenyl-1,2,3,5-tetrahydroimidazo[2,1-b]quinazolin-2-one;

7-(2-(N-imidazolyl)ethyl)oxy-6-methoxy-3-carbamoylmethyl-1,2,3,5-tetrahydroimidazo[2,1-b]quinazolin-2-one;

7-(2-(N-imidazolyl)ethyl)oxy-6-methoxy-3-carboxymethyl-1,2,3,5-tetrahydroimidazo[2,1-b]quinazolin-2-one;

7-(2-(N-imidazolyl)ethyl)oxy-6-methoxy-3-ethyl-1,2,3,5-tetrahydroimidazo[2,1-b]quinazolin-2-one;

7-(2-(N-imidazolyl)ethyl)oxy-6-methoxy-3-isopropyl-1,2,3,5-tetrahydroimidazo[2,1-b]quinazolin-2-one;

7-(3-(N-imidazolyl)propyl)oxy-6-methoxy-3-methyl-1,2,3,5-tetrahydroimidazo[2,1-b]quinazolin-2-one;

7-(3-(N-imidazolyl)propyl)oxy-6-methoxy-3-hydroxymethyl-1,2,3,5-tetrahydroimidazo[2,1-b]quinazolin-2-one;

7-(3-(N-imidazolyl)propyl)oxy-6-methoxy-3-benzyl-1,2,3,5-tetrahydroimidazo[2,1-b]quinazolin-2-one;
7-(3-(N-imidazolyl)propyl)oxy-6-methoxy-3-phenyl-1,2,3,5-tetrahydroimidazo[2,1-b]quinazolin-2-one;
7-(3-(N-imidazolyl)propyl)oxy-6-methoxy-3-carbamoylmethyl-1,2,3,5-tetrahydroimidazo[2,1-b]quinazolin-2-one;
7-(3-(N-imidazolyl)propyl)oxy-6-methoxy-3-ethyl-1,2,3,5-tetrahydroimidazo[2,1-b]quinazolin-2-one;
7-(3-(N-imidazolyl)propyl)oxy-6-methoxy-3-isopropyl-1,2,3,5-tetrahydroimidazo[2,1-b]quinazolin-2-one;
7-(4-(N-imidazolyl)butyl)oxy-6-methoxy-3-methyl-1,2,3,5-tetrahydroimidazo[2,1-b]quinazolin-2-one;
7-(4-(N-imidazolyl)butyl)oxy-6-methoxy-3-hydroxymethyl-1,2,3,5-tetrahydroimidazo[2,1-b]quinazolin-2-one;
7-(4-(N-imidazolyl)butyl)oxy-6-methoxy-3-benzyl-1,2,3,5-tetrahydroimidazo[2,1-b]quinazolin-2-one;
7-(4-(N-imidazolyl)butyl)oxy-6-methoxy-3-phenyl-1,2,3,5-tetrahydroimidazo[2,1-b]quinazolin-2-one;
7-(4-(N-imidazolyl)butyl)oxy-6-methoxy-3-carbamoylmethyl-1,2,3,5-tetrahydroimidazo[2,1-b]quinazolin-2-one;
7-(4-(N-imidazolyl)butyl)oxy-6-methoxy-3-carboxymethyl-1,2,3,5-tetrahydroimidazo[2,1-b]quinazolin-2-one;
7-(4-(N-imidazolyl)butyl)oxy-6-methoxy-3-ethyl-1,2,3,5-tetrahydroimidazo[2,1-b]quinazolin-2-one;
7-(4-(N-imidazolyl)butyl)oxy-6-methoxy-3-isopropyl-1,2,3,5-tetrahydroimidazo[2,1-b]quinazolin-2-one;
7-(5-(N-imidazolyl)pentyl)oxy-6-methoxy-3-methyl-1,2,3,5-tetrahydroimidazo[2,1-b]quinazolin-2-one;
7-(5-(N-imidazolyl)pentyl)oxy-6-methoxy-3-hydroxymethyl-1,2,3,5-tetrahydroimidazo[2,1-b]quinazolin-2-one;
7-(5-(N-imidazolyl)pentyl)oxy-6-methoxy-3-benzyl-1,2,3,5-tetrahydroimidazo[2,1-b]quinazolin-2-one;
7-(5-(N-imidazolyl)pentyl)oxy-6-methoxy-3-phenyl-1,2,3,5-tetrahydroimidazo[2,1-b]quinazolin-2-one;
7-(5-(N-imidazolyl)pentyl)oxy-6-methoxy-3-carbamoylmethyl-1,2,3,5-tetrahydroimidazo[2,1-b]quinazolin-2-one;
7-(5-(N-imidazolyl)pentyl)oxy-6-methoxy-3-carboxymethyl-1,2,3,5-tetrahydroimidazo[2,1-b]quinazolin-2-one;
7-(5-(N-imidazolyl)pentyl)oxy-6-methoxy-3-ethyl-1,2,3,5-tetrahydroimidazo[2,1-b]quinazolin-2-one;
7-(5-(N-imidazolyl)pentyl)oxy-6-methoxy-3-isopropyl-1,2,3,5-tetrahydroimidazo[2,1-b]quinazolin-2-one;
7-(7-(N-imidazolyl)heptyl)oxy-6-methoxy-3-methyl-1,2,3,5-tetrahydroimidazo[2,1-b]quinazolin-2-one;
7-(7-(N-imidazolyl)heptyl)oxy-6-methoxy-3-hydroxymethyl-1,2,3,5-tetrahydroimidazo[2,1-b]quinazolin-2-one;
7-(7-(N-imidazolyl)heptyl)oxy-6-methoxy-3-benzyl-1,2,3,5-tetrahydroimidazo[2,1-b]quinazolin-2-one;
7-(7-(N-imidazolyl)heptyl)oxy-6-methoxy-3-phenyl-1,2,3,5-tetrahydroimidazo[2,1-b]quinazolin-2-one;
7-(7-(N-imidazolyl)heptyl)oxy-6-methoxy-3-carbamoylmethyl-1,2,3,5-tetrahydroimidazo[2,1-b]quinazolin-2-one;
7-(7-(N-imidazolyl)heptyl)oxy-6-methoxy-3-carboxymethyl-1,2,3,5-tetrahydroimidazo[2,1-b]quinazolin-2-one;
7-(7-(N-imidazolyl)heptyl)oxy-6-methoxy-3-ethyl-1,2,3,5-tetrahydroimidazo[2,1-b]quinazolin-2-one;
7-(7-(N-imidazolyl)heptyl)oxy-6-methoxy-3-isopropyl-1,2,3,5-tetrahydroimidazo[2,1-b]quinazolin-2-one;
7-(8-(N-imidazolyl)octyl)oxy-6-methoxy-3-methyl-1,2,3,5-tetrahydroimidazo[2,1-b]quinazolin-2-one;
7-(8-(N-imidazolyl)octyl)oxy-6-methoxy-3-hydroxymethyl-1,2,3,5-tetrahydroimidazo[2,1-b]quinazolin-2-one;
7-(8-(N-imidazolyl)octyl)oxy-6-methoxy-3-benzyl-1,2,3,5-tetrahydroimidazo[2,1-b]quinazolin-2-one;
7-(8-(N-imidazolyl)octyl)oxy-6-methoxy-3-phenyl-1,2,3,5-tetrahydroimidazo[2,1-b]quinazolin-2-one;
7-(8-(N-imidazolyl)octyl)oxy-6-methoxy-3-carbamoylmethyl-1,2,3,5-tetrahydroimidazo[2,1-b]quinazolin-2-one;
7-(8-(N-imidazolyl)octyl)oxy-6-methoxy-3-carboxymethyl-1,2,3,5-tetrahydroimidazo[2,1-b]quinazolin-2-one;
7-(8-(N-imidazolyl)octyl)oxy-6-methoxy-3-ethyl-1,2,3,5-tetrahydroimidazo[2,1-b]quinazolin-2-one;
7-(8-(N-imidazolyl)octyl)oxy-6-methoxy-3-isopropyl-1,2,3,5-tetrahydroimidazo[2,1-b]quinazolin-2-one;
7-(2-(N-imidazolyl)ethyl)oxy-3-L-methyl-1,2,3,5-tetrahydroimidazo[2,1-b]quinazolin-2-one;
7-(2-(N-imidazolyl)ethyl)oxy-3-L-hydroxymethyl-1,2,3,5-tetrahydroimidazo[2,1-b]quinazolin-2-one;
7-(2-(N-imidazolyl)ethyl)oxy-3-L-benzyl-1,2,3,5-tetrahydroimidazo[2,1-b]quinazolin-2-one;
7-(2-(N-imidazolyl)ethyl)oxy-3-L-phenyl-1,2,3,5-tetrahydroimidazo[2,1-b]quinazolin-2-one;
7-(2-(N-imidazolyl)ethyl)oxy-3-L-carbamoylmethyl-1,2,3,5-tetrahydroimidazo[2,1-b]quinazolin-2-one;
7-(2-(N-imidazolyl)ethyl)oxy-3-L-carboxymethyl-1,2,3,5-tetrahydroimidazo[2,1-b]quinazolin-2-one;
7-(2-(N-imidazolyl)ethyl)oxy-3-L-ethyl-1,2,3,5-tetrahydroimidazo[2,1-b]quinazolin-2-one;
7-(2-(N-imidazolyl)ethyl)oxy-3-L-isopropyl-1,2,3,5-tetrahydroimidazo[2,1-b]quinazolin-2-one; or
7-(3-(N-imidazolyl)propyl)oxy-3-L-methyl-1,2,3,5-tetrahydroimidazo[2,1-b]quinazolin-2-one;
7-(3-(N-imidazolyl)propyl)oxy-3-L-hydroxymethyl-1,2,3,5-tetrahydroimidazo[2,1-b]quinazolin-2-one;
7-(3-(N-imidazolyl)propyl)oxy-3-L-benzyl-1,2,3,5-tetrahydroimidazo[2,1-b]quinazolin-2-one;
7-(3-(N-imidazolyl)propyl)oxy-3-L-phenyl-1,2,3,5-tetrahydroimidazo[2,1-b]quinazolin-2-one;
7-(3-(N-imidazolyl)propyl)oxy-3-L-carbamoylmethyl-1,2,3,5-tetrahydroimidazo[2,1-b]quinazolin-2-one;
7-(3-(N-imidazolyl)propyl)oxy-3-L-ethyl-1,2,3,5-tetrahydroimidazo[2,1-b]quinazolin-2-one;
7-(3-(N-imidazolyl)propyl)oxy-3-L-isopropyl-1,2,3,5-tetrahydroimidazo[2,1-b]quinazolin-2-one; or
7-(4-(N-imidazolyl)butyl)oxy-3-L-methyl-1,2,3,5-tetrahydroimidazo[2,1-b]quinazolin-2-one;
7-(4-(N-imidazolyl)butyl)oxy-3-L-hydroxymethyl-1,2,3,5-tetrahydroimidazo[2,1-b]quinazolin-2-one;
7-(4-(N-imidazolyl)butyl)oxy-3-L-benzyl-1,2,3,5-tetrahydroimidazo[2,1-b]quinazolin-2-one;
7-(4-(N-imidazolyl)butyl)oxy-3-L-phenyl-1,2,3,5-tetrahydroimidazo[2,1-b]quinazolin-2-one;
7-(4-(N-imidazolyl)butyl)oxy-3-L-carbamoylmethyl-1,2,3,5-tetrahydroimidazo[2,1-b]quinazolin-2-one;
7-(4-(N-imidazolyl)butyl)oxy-3-L-carboxymethyl-1,2,3,5-tetrahydroimidazo[2,1-b]quinazolin-2-one;
7-(4-(N-imidazolyl)butyl)oxy-3-L-ethyl-1,2,3,5-tetrahydroimidazo[2,1-b]quinazolin-2-one;
7-(4-(N-imidazolyl)butyl)oxy-3-L-isopropyl-1,2,3,5-tetrahydroimidazo[2,1-b]quinazolin-2-one; or
7-(5-(N-imidazolyl)pentyl)oxy-3-L-methyl-1,2,3,5-tetrahydroimidazo[2,1-b]quinazolin-2-one;

7-(5-(N-imidazolyl)pentyl)oxy-3-L-hydroxymethyl-1,2,3,5-tetrahydroimidazo[2,1-b]quinazolin-2-one;
7-(5-(N-imidazolyl)pentyl)oxy-3-L-benzyl-1,2,3,5-tetrahydroimidazio[2,1-b]quinazolin-2-one;
7-(5-(N-imidazolyl)pentyl)oxy-3-L-phenyl-1,2,3,5-tetrahydroimidazo[2,1-b]quinazolin-2-one;
7-(5-(N-imidazolyl)pentyl)oxy-3-L-carbamoylmethyl-1,2,3,5-tetrahydroimidazo[2,1-b]quinazolin-2-one;
7-(5-(N-imidazolyl)pentyl)oxy-3-L-carboxymethyl-1,2,3,5-tetrahydroimidazo[2,1-b]quinazolin-2-one;
7-(5-(N-imidazolyl)pentyl)oxy-3-L-ethyl-1,2,3,5-tetrahydroimidazo[2,1-b]quinazolin-2-one;
7-(5-(N-imidazolyl)pentyl)oxy-3-L-isopropyl-1,2,3,5-tetrahydroimidazo[2,1-b]quinazolin-2-one; or
7-(7-(N-imidazolyl)heptyl)oxy-3-L-methyl-1,2,3,5-tetrahydroimidazo[2,1-b]quinazolin-2-one;
7-(7-(N-imidazolyl)heptyl)oxy-3-L-hydroxymethyl-1,2,3,5-tetrahydroimidazo[2,1-b]quinazolin-2-one;
7-(7-(N-imidazolyl)heptyl)oxy-3-L-benzyl-1,2,3,5-tetrahydroimidazo[2,1-b]quinazolin-2-one;
7-(7-(N-imidazolyl)heptyl)oxy-3-L-phenyl-1,2,3,5-tetrahydroimidazo[2,1-b]quinazolin-2-one;
7-(7-(N-imidazolyl)heptyl)oxy-3-L-carbamoylmethyl-1,2,3,5-tetrahydroimidazo[2,1-b]quinazolin-2-one;
7-(7-(N-imidazolyl)heptyl)oxy-3-L-carboxymethyl-1,2,3,5-tetrahydroimidazo[2,1-b]quinazolin-2-one;
7-(7-(N-imidazolyl)heptyl)oxy-3-L-ethyl-1,2,3,5-tetrahydroimidazo[2,1-b]quinazolin-2-one;
7-(7-(N-imidazolyl)heptyl)oxy-3-L-isopropyl-1,2,3,5-tetrahydroimidazo[2,1-b]quinazolin-2-one; or
7-(8-(N-imidazolyl)octyl)oxy-3-L-methyl-1,2,3,5-tetrahydroimidazo[2,1-b]quinazolin-2-one;
7-(8-(N-imidazolyl)octyl)oxy-3-L-hydroxymethyl-1,2,3,5-tetrahydroimidazo[2,1-b]quinazolin-2-one;
7-(8-(N-imidazolyl)octyl)oxy-3-L-benzyl-1,2,3,5-tetrahydroimidazo[2,1-b]quinazolin-2-one;
7-(8-(N-imidazolyl)octyl)oxy-3-L-phenyl-1,2,3,5-tetrahydroimidazo[2,1-b]quinazolin-2-one;
7-(8-(N-imidazolyl)octyl)oxy-3-L-carbamoylmethyl-1,2,3,5-tetrahydroimidazo[2,1-b]quinazolin-2-one;
7-(8-(N-imidazolyl)octyl)oxy-3-L-carboxymethyl-1,2,3,5-tetrahydroimidazo[2,1-b]quinazolin-2-one;
7-(8-(N-imidazolyl)octyl)oxy-3-L-ethyl-1,2,3,5-tetrahydroimidazo[2,1-b]quinazolin-2-one;
7-(8-(N-imidazolyl)octyl)oxy-3-L-isopropyl-1,2,3,5-tetrahydroimidazo[2,1-b]quinazolin-2-one; or
7-(2-(N-imidazolyl)ethyl)oxy-3-D-methyl-1,2,3,5-tetrahydroimidazo[2,1-b]quinazolin-2-one;
7-(2-(N-imidazolyl)ethyl)oxy-3-D-hydroxymethyl-1,2,3,5-tetrahydroimidazo[2,1-b]quinazolin-2-one;
7-(2-(N-imidazolyl)ethyl)oxy-3-D-benzyl-1,2,3,5-tetrahydroimidazo[2,1-b]quinazolin-2-one;
7-(2-(N-imidazolyl)ethyl)oxy-3-D-phenyl-1,2,3,5-tetrahydroimidazo[2,1-b]quinazolin-2-one;
7-(2-(N-imidazolyl)ethyl)oxy-3-D-carbamoylmethyl-1,2,3,5-tetrahydroimidazo[2,1-b]quinazolin-2-one;
7-(2-(N-imidazolyl)ethyl)oxy-3-D-carboxymethyl-1,2,3,5-tetrahydroimidazo[2,1-b]quinazolin-2-one;
7-(2-(N-imidazolyl)ethyl)oxy-3-D-ethyl-1,2,3,5-tetrahydroimidazo[2,1-b]quinazolin-2-one;
7-(2-(N-imidazolyl)ethyl)oxy-3-D-isopropyl-1,2,3,5-tetrahydroimidazo[2,1-b]quinazolin-2-one; or
7-(3-(N-imidazolyl)propyl)oxy-3-D-methyl-1,2,3,5-tetrahydroimidazo[2,1-b]quinazolin-2-one;
7-(3-(N-imidazolyl)propyl)oxy-3-D-hydroxymethyl-1,2,3,5-tetrahydroimidazo[2,1-b]quinazolin-2-one;
7-(3-(N-imidazolyl)propyl)oxy-3-D-benzyl-1,2,3,5-tetrahydroimidazo[2,1-b]quinazolin-2-one;
7-(3-(N-imidazolyl)propyl)oxy-3-D-phenyl-1,2,3,5-tetrahydroimidazo[2,1-b]quinazolin-2-one;
7-(3-(N-imidazolyl)propyl)oxy-3-D-carbamoylmethyl-1,2,3,5-tetrahydroimidazo[2,1-b]quinazolin-2-one;
7-(3-(N-imidazolyl)propyl)oxy-3-D-carboxymethyl-1,2,3,5-tetrahydroimidazo[2,1-b]quinazolin-2-one;
7-(3-(N-imidazolyl)propyl)oxy-3-D-ethyl-1,2,3,5-tetrahydroimidazo[2,1-b]quinazolin-2-one;
7-(3-(N-imidazolyl)propyl)oxy-3-D-isopropyl-1,2,3,5-tetrahydroimidazo[2,1-b]quinazolin-2-one; or
7-(4-(N-imidazolyl)butyl)oxy-3-D-methyl-1,2,3,5-tetrahydroimidazo[2,1-b]quinazolin-2-one;
7-(4-(N-imidazolyl)butyl)oxy-3-D-hydroxymethyl-1,2,3,5-tetrahydroimidazo[2,1-b]quinazolin-2-one;
7-(4-(N-imidazolyl)butyl)oxy-3-D-benzyl-1,2,3,5-tetrahydroimidazo[2,1-b]quinazolin-2-one;
7-(4-(N-imidazolyl)butyl)oxy-3-D-phenyl-1,2,3,5-tetrahydroimidazo[2,1-b]quinazolin-2-one;
7-(4-(N-imidazolyl)butyl)oxy-3-D-carbamoylmethyl-1,2,3,5-tetrahydroimidazo[2,1-b]quinazolin-2-one;
7-(4-(N-imidazolyl)butyl)oxy-3-D-carboxymethyl-1,2,3,5-tetrahydroimidazo[2,1-b]quinazolin-2-one;
7-(4-(N-imidazolyl)butyl)oxy-3-D-ethyl-1,2,3,5-tetrahydroimidazo[2,1-b]quinazolin-2-one;
7-(4-(N-imidazolyl)butyl)oxy-3-D-isopropyl-1,2,3,5-tetrahydroimidazo[2,1-b]quinazolin-2-one; or
7-(5-(N-imidazolyl)pentyl)oxy-3-D-methyl-1,2,3,5-tetrahydroimidazo[2,1-b]quinazolin-2-one;
7-(5-(N-imidazolyl)pentyl)oxy-3-D-hydroxymethyl-1,2,3,5-tetrahydroimidazo[2,1-b]quinazolin-2-one;
7-(5-(N-imidazolyl)pentyl)oxy-3-D-benzyl-1,2,3,5-tetrahydroimidazo[2,1-b]quinazolin-2-one;
7-(5-(N-imidazolyl)pentyl)oxy-3-D-phenyl-1,2,3,5-tetrahydroimidazo[2,1-b]quinazolin-2-one;
7-(5-(N-imidazolyl)pentyl)oxy-3-D-carbamoylmethyl-1,2,3,5-tetrahydroimidazo[2,1-b]quinazolin-2-one;
7-(5-(N-imidazolyl)pentyl)oxy-3-D-carboxymethyl-1,2,3,5-tetrahydroimidazo[2,1-b]quinazolin-2-one;
7-(5-(N-imidazolyl)pentyl)oxy-3-D-ethyl-1,2,3,5-tetrahydroimidazo[2,1-b]quinazolin-2-one;
7-(5-(N-imidazolyl)pentyl)oxy-3-D-isopropyl-1,2,3,5-tetrahydroimidazo[2,1-b]quinazolin-2-one; or
7-(7-(N-imidazolyl)heptyl)oxy-3-D-methyl-1,2,3,5-tetrahydroimidazo[2,1-b]quinazolin-2-one;
7-(7-(N-imidazolyl)hepthyl)oxy-3-D-hydroxymethyl-1,2,3,5-tetrahydroimidazo[2,1-b]quinazolin-2-one;
7-(7-(N-imidazolyl)heptyl)oxy-3-D-benzyl-1,2,3,5-tetrahydroimidazo[2,1-b]quinazolin-2-one;
7-(7-(N-imidazolyl)heptyl)oxy-3-D-phenyl-1,2,3,5-tetrahydroimidazo[2,1-b]quinazolin-2-one;
7-(7-(N-imidazolyl)heptyl)oxy-3-D-carbamoylmethyl-1,2,3,5-tetrahydroimidazo[2,1-b]quinazolin-2-one;
7-(7-(N-imidazolyl)heptyl)oxy-3-D-carboxymethyl-1,2,3,5-tetrahydroimidazo[2,1-b]quinazolin-2-one;
7-(7-(N-imidazolyl)heptyl)oxy-3-D-ethyl-1,2,3,5-tetrahydroimidazo[2,1-b]quinazolin-2-one;
7-(7-(N-imidazolyl)heptyl)oxy-3-D-isopropyl-1,2,3,5-tetrahydroimidazo[2,1-b]quinazolin-2-one; or
7-(8-(N-imidazolyl)octyl)oxy-3-D-methyl-1,2,3,5-tetrahydroimidazo[2,1-b]quinazolin-2-one;
7-(8-(N-imidazolyl)octyl)oxy-3-D-hydroxymethyl-1,2,3,5-tetrahydroimidazo[2,1-b]quinazolin-2-one;
7-(8-(N-imidazolyl)octyl)oxy-3-D-benzyl-1,2,3,5-tetrahydroimidazo[2,1-b]quinazolin-2-one;
7-(8-(N-imidazolyl)octyl)oxy-3-D-phenyl-1,2,3,5-tetrahydroimidazo[2,1-b]quinazolin-2-one;
7-(8-(N-imidazolyl)octyl)oxy-3-D-carbamoylmethyl-1,2,3,5-tetrahydroimidazo[2,1-b]quinazolin-2-one;

7-(8-(N-imidazolyl)octyl)oxy-3-D-carboxymethyl-1,2,3,5-tetrahydroimidazo[2,1-b]quinazolin-2-one;

7-(8-(N-imidazolyl)octyl)oxy-3-D-ethyl-1,2,3,5-tetrahydroimidazo[2,1-b]quinazolin-2-one;

7-(8-(N-imidazolyl)octyl)oxy-3-D-isopropyl-1,2,3,5-tetrahydroimidazo[2,1-b]quinazolin-2-one; and other compounds depending on the $R_3$ substitution.

EXAMPLE 11

Conversion of Compound I to Compound I With Various $R_4$ Substitution

The compounds of formula I wherein $R_4$ is hydrogen are converted to those wherein $R_4$ is alkyl of 1 to 6 carbon atoms, benzyl or hydroxy lower alkyl by the following procedure.

I. Preparation of 7-(6-(N-Imidazolyl)hexyl)oxy-1-butyl-1,2,3,5-tetrahydroimidazo[2,1-b]quinazolin-2-one To a solution of 7-(6-(N-imidazolyl)hexyl)oxy-1,2,3,5-tetrahydroimidazo[2,1-b]quinazolin-2-one in dry dimethylformamide is added sodium hydride (1.05 equivalents). The mixture is stirred at 60° C. for 30 minutes to give a homogeneous solution. 1-bromobutane (1.1 equivalents) is added via a syringe after which the mixture is stirred at 60° C. for 2 hours. The solvent is evaporated and the residue taken up in ethyl acetate which is washed with saturated brine, dried and filtered. Evaporation of the solvent affords 7-(6-(N-imidazolyl)-hexyl)oxy-1-butyl-1,2,3,5-tetrahydroimidazo[2,1-b]-quinazolin-2-one.

EXAMPLE 12

Conversion of Free Base to Salt

A two-fold stoichiometric excess of 3% hydrogen chloride in methanol is added to a solution of 1.0 g. of 7-(6-(N-imidazolyl)hexyl)oxy-1,2,3,5-tetrahydroimidazo[2,1-b]quinazolin-2-one in 50 ml methanol. Diethyl ether is added until precipitation is complete. The product is filtered, washed with ether, air dried and recrystallized to give 7-(6-(N-imidazolyl)hexyl)oxy-1,2,3,5-tetrahydroimidazo-[2,1-b]-quinazolin-2-one.

In a similar manner, all compounds of formula I in free base form may be converted to the acid addition salt by treatment with hydrogen chloride or another pharmaceutically acceptable acid addition salt-forming acid such as exemplified herein earlier.

EXAMPLE 13

Conversion of Salt to Free Base 1.0 g of 7-(6-(N-imidazolyl)hexyl)oxy-1,2,3,5-tetrahydroimidazo[2,1-b]quinazolin-2-one HCl suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 7-(6-(N-imidazolyl)hexyl)oxy-1,2,3,5-tetrahydroimidazo[2,1-b]quinazolin-2-one as the free base.

EXAMPLE 14

Direct interchange of acid addition salts 7-(6-(N-imidazolyl)hexyl)oxy-1,2,3,5-tetrahydroimidazo[2,1-b]quinazolin-2-one acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield 7-(6-(N-imidazolyl)hexyl)oxy-1,2,3,5-tetrahydroimidazo[2,1-b]quinazolin-2-one sulfate.

In Examples 15-22, active ingredient is 7-(6-(N-imidazolyl)hexyl)oxy-1,2,3,5-tetrahydroimidazo[2,1-b]quinazolin-2-one dihydrochloride.

EXAMPLE 15

Preparation of Oral Pharmaceutical Composition in The Form of a Tablet

Compounds of the present invention, either the free base or a pharmaceutically acceptable acid addition salt, may be orally administered to a subject as a tablet. While the active ingredient may comprise anywhere between 5 and 90 percent of the formation that percentage preferably will be an amount which will cause to be delivered to the subject, the active ingredient in an amount of between 20 mg and 100 mg per tablet. Following is a representative tablet formulation in which the active ingredient is 7-(6-(N-imidazolyl)hexyl)oxy-1,2,3,5-tetrahydroimidazo[2,1-b]quinazolin-2-one dihydrochloride. However, the formulation profile given below may be used to formulate a tablet for any of the compounds represented by Formula I.

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 16

Preparation of Oral Pharmaceutical Composition in The Form of Gelatin Compounds

An alternative oral dosage form is to fill hard shell gelatin capsules with a powder containing the active ingredient in the desired amount. Using the active ingredient mentioned in Example 6 above, the acid addition salts, or any other compound according to Formula I there may be prepared an exemplary hard shell gelatin capsule formulation using the following ingredients:

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 17

Preparation of Pharmaceutical Composition in The Form of a Suspension

Alternatively, compounds of the present invention may be prepared as a suspension for oral administration. Any of the compounds of Formula I, either in freelance form or as the acid addition salt, may be used in this formulation.

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |

EXAMPLE 18

| Ingredients | Quantity per tablet, mgs. |
|---|---|
| Active ingredient | 200 |
| cornstarch | 50 |
| lactose | 145 |
| magnesium stearate | 5 |

The above ingredients are mixed intimately and pressed into single scored tablets.

EXAMPLE 19

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 20

| Ingredients | Quantity per tablet, mgs |
|---|---|
| Active ingredient | 150 |
| lactose | 92 |

The above ingredients are mixed and introduced into a hard-shell gelatin capsule.

EXAMPLE 21

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) q.s. to | pH 7 |
| water (distilled, sterile) q.s. to | 20 ml |

EXAMPLE 22

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water q.s. to | 100 ml |

EXAMPLE 23

In Vitro Human Platelet Aggregation Inhibition

Biological activity of the claimed compounds was tested by in vitro human platelet aggregation assay. This assay determines the effectiveness of the compounds in inhibiting the platelet aggregation.

The assay employs modified turbidimetric methods of Born (*J. Physiol.*, 67P (1962) and Evans et al, *J. Exp. Med.*, 128, 877P (1968), and it is based on the physiological response of the blood platelets to a certain stimuli. In normal circulating blood, platelets are carried along separately from each other and they do not adhere to undamaged endothelium. In response to any direct damage to the vascular wall, however, the blood platelets will start to aggregate. Thus, whenever there occurs an injury causing bleeding, rupture, cut or another type of damage to vascular wall, the collagen fibers in the wall become exposed and platelets immediately start to adhere to them and begin to form a platelet thrombi. Immediately thereafter, the platelets start to secrete large quantities of adenosine diphosphate (ADP) which, in turn activates the other platelets that adhere to the original platelets and eventually form the plug which closes the rupture of the vascular wall. In medical parlance the first process is called collagen-induced primary platelet aggregation, the second process is called ADP-mediated secondary platelet aggregation. This situation can be artificially simulated by natural platelet aggregation inducers such as collagen, ADP, or arachidonic acid to the human platelet-rich plasma.

Experimental Protocol

A. Preparation of human platelets-rich plasma

The blood samples used for the assay were collected into sodium citrate anticoagulant of a final concentration of 0.38%. The platelet-rich plasma was collected after centrifugation at 200 rpm at room temperature. To determine whether the platelet-rich plasma needs dilution to obtain optimal optical density, citrated plasma containing $10^{-8}$–$10^{-9}$ platelets per milliliter was pipetted into a Spinco transparent plastic centrifuge tube. The tube was inserted into a Unicam SP 400 absorptiometer and the light at the wave-length of 600 m was passed through the tube. The dark current was set at infinity and the optical density of distilled water at zero. The plasma was stirred by a magnetic stirrer. When necessary, platelet-rich plasma is diluted with 0.154M sodium chloride to obtain appropriate optical density.

B. Platelet aggregation procedure

Platelet-rich plasma of appropriate optical density was mixed with appropriate concentration of tested compounds to make up 1 ml of mixture of platelet-rich plasma and tested compound. The concentration of each tested compound varied from $1.0 \times 10^{-5}$ moles to $1.0 \times 10^{-9}$ moles. Each concentration was tested individually by number of repetitions varying from 1 to 6.

Each sample mixture consisting of platelet-rich plasma and tested compound was incubated for about 3 to 5 minutes under constant stirring at 500 rpm at 30° C. Thereafter, a predetermined optimal concentration of platelet aggregation inducer was added to each sample mixture. Inducers which were used for testing may be chosen from:

1. Collagen Suspension Inducer

Collagen suspension was prepared by dissolving 2 g of commercial collagen (Sigma Chemical Company) in 100 ml of modified Tyrode's solution at 0° C. and homogenized in the Waring blender for a total of 5 minutes. To remove coarse particle matter the mixture was centrifuged at 810 rpm for 10 minutes. The supernatant suspension was then diluted with modified Tyrode's solution to a concentration which produce maximum aggregation of the platelets being tested, but which, on further dilution, cause less than maximum aggregation.

2. Adenosine Diphosphate Inducer

Adenosine Diphosphate (ADP) was purchased from Sigma Chemical Company. ADP inducer solution of final concentration of 5 $\mu$mol is prepared by dissolving 214 mg of ADP in 1 ml of tris buffer (0.01M at pH 9 at 22 C O). Optimal amount of ADP inducer was found to be 5 $\mu$mol.

3. Arachidonic Acid Inducer

Arachidonic acid (Nu Chek Prep Co.) inducer solution is prepared by dissolving 150–300 $\mu$g of arachidonic acid in 1 ml of a mixture of 10% of ethanol and 90% of 65.6 mmol of sodium carbonate buffer to achieve concentration 0.5 to 1 mmol.

A tube with the mixture of platelet-rich plasma, tested compound and ADP inducer (5 $\mu$mol/10 $\mu$l) was inserted into the absorptiometer and optical density changes were recorded on chart. Aggregation of the platelets was determined from maximal optical density change. Maximal optical density of a mixture of platelet-rich plasma with inducer, but without the tested compounds, was taken as 100% of platelet aggregation. The maximal optical density of the sample mixture of platelet-rich plasma, ADP inducer and appropriate amount of tested compound was compared to the maximal optical density of the sample without tested compound and inhibitory effectiveness of tested compounds was calculated. For each sample the percentage of platelet aggregation was calculated and if more than one measurement with the same concentration of the tested compounds were done, the final value was expressed as an average of all measurements with $\pm$S.E. The inhibitory concentration was the effective concentration of tested compound which was able to prevent 50% of the platelet aggregation, where, without the tested compound, the platelet aggregation would have been 100%. The Potency of Inhibitor or IC$_{50}$ is expressed in relationship to inhibitory effectiveness of PGE$_1$ which is arbitrarily denominated as 1.

C. Results

The compounds of this invention were tested by this procedure and were found to be active inhibitors of platelet aggregation. IC$_{50}$ was 40 $\mu$moles.

EXAMPLE 24

In Vitro Inhibition of Cyclic AMP Phosphodiesterase Activity

This example illustrates the inhibition of cyclic AMP phosphodiesterase by the compounds of this invention. Cyclic AMP phosphodiesterase activity and inhibition of platelet aggregation were determined as follows.

A. Experimental Protocol

The inhibition of cyclic AMP phosphodiesterase activity by the compounds of the current invention is assayed by the method of Filburn and Karn, *Analyt. Biochem.*, 52:505–516 (1973), using 1 $\mu$M cyclic AMP as the substrate.

Human platelet cyclic AMP phosphodiesterase used in the procedure is obtained from human donors. Platelets are isolated and washed by centrifugation, the membranes ruptured by a sequential freeze-thaw procedure and hypotonic lysis and the soluble enzyme isolated by high speed centrifugation. The enzyme is stored in aliquots at $-20$° C.

B. Results

Compounds of this invention are potent inhibitors of cyclic AMP phosphodiesterase.

EXAMPLE 25

In Vitro Thromboxane A$_2$ Synthetase Activity

This example illustrates the ability of compounds of this invention to inhibit thromboxane synthetase.

It has been previously discovered that collagen induces aggregation of the human platelet-rich plasma (PRP) and that during this process large amounts of thromboxane A$_2$ (TxA$_2$) are produced. Thromboxane can be quantitated by measuring the inactive spontaneous degradation product TxB$_2$.

A. Experimental Protocol

Platelet aggregation induced by collagen as described in Example 23, was followed by the method of Born, *J. Physiol.*, 162:67P, 1962), using a Payton Dual Channel aggregometer.

At appropriate time intervals, aliquot of the PRP were withdrawn and immediately killed by addition to an equal volume of ethanol. After sedimentation of the resulting precipitate, TxB$_2$ in the supernatant was assayed by radioimmuno-assay according to the procedure supplied with RIA kits from New England Nuclear Corp.

Thromboxane synthetase inhibiting activity was compared with that of the experimental drug dazoxiben. The activity of dazoxiben has arbitrarily been designated as 1.

B. Results

Compounds of the current invention were found to be potent inhibitors of thromboxane A$_2$ synthetase. IC$_{50}$ was 0.4 $\mu$mol, approximately 5 to 6 times more potent than dazoxiben.

EXAMPLE 26

Inotropic Activity of the Compounds of the present Invention

A. Experimental Protocol

Mongrel dogs are anesthetized i.v. with 35 mg/kg sodium pentobarbital and supplemented as needed. Blood pressure ia measured with a Statham pressure transducer via a cannula inserted from a femoral artery into the abdominal aorta. Heart rate is recorded by a cardiotachometer from a lead II electrocardiogram. Right ventricular contractile force is recorded from a Walton-Brodie strain gauge sutured to the right ventricle following a midsternal thoracotomy. A Harvard respirator is used to ventilate the dogs with room air through an endotracheal tube. The dog is bilaterally vagotomized. Following a midline laparotomy, a cannula is sutured into the duodenum for intraduodenal administration of test compound. A femoral vein is cannulated for administration of isoproterenol. All data are recorded on a Beckman R611 Dynograph.

To assess the responsiveness of each dog, isoproterenol is given i.v. at half-log interval doses from 0.007 to 2.1 or 6.67 μg/Kg. The test compound is then administered intraduodenally, usually at a low dose of 2 mg/Kg and subsequently at higher doses of 6.32 and/or 20 mg/Kg, if necessary. In a few instances, some compounds are administered intraduodenally at dose levels from 0.316 to 3.16 mg/Kg.

B. Results

The compounds of this invention have positive inotropic effect.

EXAMPLE 27

Antimetastatic activity against Lewis Lung Carcinoma (Spontaneous Metastases)

A. Experimental Protocol

Mice (female, C57B1/6, 16–18 gm) are inoculated subcutaneously between the inguinal and axillary areas with 0.2 ml of a freshly prepared tumor brei. Mice are treated orally with control vehicle (0.5% carboxymethylcellulose (CMC)) or with test compound in suspension in 0.5% CMC. Treatments are initiated one day after tumor implantation, and continued every other day throughout the experiment. 20–21 days after initial implantation of the tumor, mice are sacrificed, weight of the primary tumor is determined, and the number of lung metastases is determined by counting under a disecting microscope.

B. Results

The compounds of this invention have positive antitumor activity.

EXAMPLE 28

Antimetastatic activity against B-16 Melanoma

A. Experimental Protocol

Mice (female, C57B1/6, 16–18 gm) are injected intravenously with either $7.5 \times 10^4$ viable B16-BL6 or B16-F10 melanoma cells, as indicated. The mice are orally treated with vehicle or drug, starting one day after tumor cell injection, and continuing every other day until the mice are sacrificed 20–21 days after tumor cell inoculation. The number of lung metastases is determined as described above.

B. Results

Compounds of this invention are able to decrease the number of metastases.

What is claimed is:

1. A compound of the formula

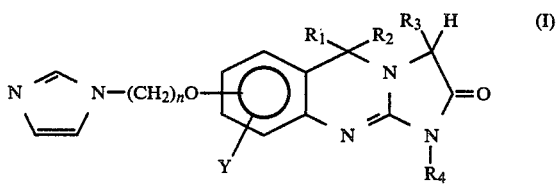

wherein:
n is an integer of 1 to 8;
$R_1$ is hydrogen or alkyl of 1–6 carbons;
$R_2$ is hydrogen;
$R_3$ is hydrogen, alkyl of 1–6 carbons, phenyl, benzyl, hydroxy lower alkyl, carbamoylalkyl, carboxyalkyl, alkoxycarbonylalkyl;
$R_4$ is hydrogen, alkyl of 1–6 carbons, benzyl, or hydroxy lower alkyl;
Y is hydrogen, alkyl of 1 to 4 carbon atoms, halo or lower alkoxy;
any of its optical isomers, the mixture thereof, or a pharmaceutically acceptable acid addition salt.

2. The compound of claim 1 wherein n is an integer of 2 to 6.

3. The compound of claim 2 wherein n is 2 and $R_1$, $R_2$ and $R_4$ are hydrogen.

4. The compound of claim 3 wherein $R_3$ is hydrogen.

5. The compound of claim 4 wherein Y is hydrogen, namely 7-[2-(N-imidazolyl)ethyl]oxy-1,2,3,5-tetrahydroimidazo[2,1-b]quinazolin-2-one.

6. The compound of claim 4 wherein Y is chloro, namely 7-[2-(N-imidazolyl)ethyl]oxy-6-chloro-1,2,3,5-tetrahydroimidazo[2,1-b]quinazolin-2-one.

7. The compound of claim 4 wherein Y is methoxy, namely 7-[2-(N-imidazolyl)ethyl]oxy-6-methoxy-1,2,3,5-tetrahydroimidazo[2,1-b]quinazolin-2-one.

8. The compound of claim 3 wherein $R_3$ is methyl.

9. The compound of claim 8 wherein Y is hydrogen, namely 7-[2-(N-imidazolyl)ethyl]oxy-3-methyl-1,2,3,5-tetrahydroimidazo[2,1-b]quinazolin-2-one.

10. The compound of claim 8 wherein Y is chloro, namely 7-[2-(N-imidazolyl)ethyl]oxy-6-chloro-3-methyl-1,2,3,5-tetrahydroimidazo[2,1-b]quinazolin-2-one.

11. The compound of claim 8 wherein Y is methoxy, namely 7-[2-(N-imidazolyl)ethyl]oxy-6-methoxy-3-methyl-1,2,3,5-tetrahydroimidazo[2,1-b]quinazolin-2-one.

12. The compound of claim 3 wherein $R_3$ is ethyl.

13. The compound of claim 12 wherein Y is hydrogen, namely 7-[2-(N-imidazolyl)ethyl]oxy-3-ethyl-1,2,3,5-tetrahydroimidazo[2,1-b]quinazolin-2-one.

14. The compound of claim 12 wherein Y is chloro, namely 7-[2-(N-imidazolyl)ethyl]oxy-6-chloro-3-ethyl-1,2,3,5-tetrahydroimidazo[2,1-b]quinazolin-2-one.

15. The compound of claim 12 wherein Y is methoxy, namely 7-[2-(N-imidazolyl)ethyl]oxy-6-methoxy-3-ethyl-1,2,3,5-tetrahydroimidazo[2,1-b]quinazolin-2-one.

16. The compound of claim 3 wherein $R_3$ is hydroxymethyl.

17. The compound of claim 16 wherein Y is hydrogen, namely 7-[2-(N-imidazolyl)ethyl]oxy-3-hydroxymethyl-1,2,3,5-tetrahydroimidazo[2,1-b]quinazolin-2-one.

18. The compound of claim 16 wherein Y is chloro, namely 7-[2-(N-imidazolyl)ethyl]oxy-6-chloro-3-hydroxy-methyl-1,2,3,5-tetrahydroimidazo[2,1-b]quinazolin-2-one.

19. The compound of claim 12 wherein Y is methoxy, namely 7-[2-(N-imidazolyl)ethyl]oxy-6-methoxy-3-hydroxy-methyl-1,2,3,5-tetrahydroimidazo[2,1-b]quinazolin-2-one.

20. The compound of claim 2 wherein n is 3 and $R_1$, $R_2$ and $R_4$ are hydrogen.

21. The compound of claim 20 wherein $R_3$ is hydrogen.

22. The compound of claim 21 wherein Y is hydrogen, namely 7-[3-(N-imidazolyl)propyl]oxy-1,2,3,5-tetrahydroimidazo[2,1-b]quinazolin-2-one.

23. The compound of claim 21 wherein Y is chloro, namely 7-[3-(N-imidazolyl)propyl]oxy-6-chloro-1,2,3,5-tetrahydroimidazo[2,1-b]quinazolin-2-one.

24. The compound of claim 21 wherein Y is methoxy, namely 7-[3-(N-imidazolyl)propyl]oxy-6-methoxy-1,2,3,5-tetrahydroimidazo[2,1-b]quinazolin-2-one.

25. The compound of claim 20 wherein $R_3$ is methyl.

26. The compound of claim 25 wherein Y is hydrogen, namely 7-[3-(N-imidazolyl)propyl]oxy-3-methyl-1,2,3,5-tetrahydroimidazo[2,1-b]quinazolin-2-one.

27. The compound of claim 25 wherein Y is chloro, namely 7-[3-(N-imidazolyl)propyl]oxy-6-chloro-3-methyl-1,2,3,5-tetrahydroimidazo[2,1-b]quinazolin-2-one.

28. The compound of claim 25 wherein Y is methoxy, namely 7-[3-(N-imidazolyl)propyl]oxy-6-methoxy-3-methyl-1,2,3,5-tetrahydroimidazo[2,1-b]quinazolin-2-one.

29. The compound of claim 20 wherein $R_3$ is ethyl.

30. The compound of claim 29 wherein Y is hydrogen, namely 7-[3-(N-imidazolyl)propyl]oxy-3-ethyl-1,2,3,5-tetrahydroimidazo[2,1-b]quinazolin-2-one.

31. The compound of claim 29 wherein Y is chloro, namely 7-[3-(N-imidazolyl)propyl]oxy-6-chloro-3-ethyl-1,2,3,5-tetrahydroimidazo[2,1-b]quinazolin-2-one.

32. The compound of claim 29 wherein Y is methoxy, namely 7-[3-(N-imidazolyl)propyl]oxy-6-methoxy-3-methyl-1,2,3,5-tetrahydroimidazo[2,1-b]quinazolin-2-one.

33. The compound of claim 20 wherein $R_3$ is hydroxymethyl.

34. The compound of claim 33 wherein Y is hydrogen, namely 7-[3-(N-imidazolyl)propyl]oxy-3-hydroxymethyl-1,2,3,5-tetrahydroimidazo[2,1-b]quinazolin-2-one.

35. The compound of claim 33 wherein Y is chloro, namely 7-[3-(N-imidazolyl)propyl]oxy-6-chloro-3-hydroxymethyl-1,2,3,5-tetrahydroimidazo[2,1-b]quinazolin-2-one.

36. The compound of claim 33 wherein Y is methoxy, namely 7-[3-(N-imidazolyl)propyl]oxy-6-methoxy-3-hydroxymethyl-1,2,3,5-tetrahydroimidazo[2,1-b]quinazolin-2-one.

37. The compound of claim 2 wherein n is 4 and $R_1$, $R_2$ and $R_4$ are hydrogen.

38. The compound of claim 37 wherein $R_3$ is hydrogen.

39. The compound of claim 38 wherein Y is hydrogen, namely 7-[4-(N-imidazolyl)butyl]oxy-1,2,3,5-tetrahydroimidazo[2,1-b]quinazolin-2-one.

40. The compound of claim 38 wherein Y is chloro, namely 7-[4-(N-imidazolyl)butyl]oxy-6-chloro-1,2,3,5-tetrahydroimidazo[2,1-b]quinazolin-2-one.

41. The compound of claim 38 wherein Y is methoxy, namely 7-[4-(N-imidazolyl)butyl]oxy-6-methoxy-1,2,3,5-tetrahydroimidazo[2,1-b]quinazolin-2-one.

42. The compound of claim 37 wherein $R_3$ is methyl.

43. The compound of claim 42 wherein Y is hydrogen, namely 7-[4-(N-imidazolyl)butyl]oxy-3-methyl-1,2,3,5-tetrahydroimidazo[2,1-b]quinazolin-2-one.

44. The compound of claim 42 wherein Y is chloro, namely 7-[4-(N-imidazolyl)butyl]oxy-6-chloro-3-methyl-1,2,3,5-tetrahydroimidazo[2,1-b]quinazolin-2-one.

45. The compound of claim 42 wherein Y is methoxy, namely 7-[4-(N-imidazolyl)butyl]oxy-6-methoxy-3-methyl-1,2,3,5-tetrahydroimidazo[2,1-b]quinazolin-2-one.

46. The compound of claim 37 wherein $R_3$ is ethyl.

47. The compound of claim 46 wherein Y is hydrogen, namely 7-[4-(N-imidazolyl)butyl]oxy-3-ethyl-1,2,3,5-tetrahydroimidazo[2,1-b]quinazolin-2-one.

48. The compound of claim 46 wherein Y is chloro, namely 7-[4-(N-imidazolyl)butyl]oxy-6-chloro-3-ethyl-1,2,3,5-tetrahydroimidazo[2,1-b]quinazolin-2-one.

49. The compound of claim 46 wherein Y is methoxy, namely 7-[4-(N-imidazolyl)butyl]oxy-6-methoxy-3-methyl-1,2,3,5-tetrahydroimidazo[2,1-b]quinazolin-2-one.

50. The compound of claim 37 wherein $R_3$ is hydroxymethyl.

51. The compound of claim 50 wherein Y is hydrogen, namely 7-[4-(N-imidazolyl)butyl]oxy-3-hydroxymethyl-1,2,3,5-tetrahydroimidazo[2,1-b]quinazolin-2-one.

52. The compound of claim 50 wherein Y is chloro, namely 7-[4-(N-imidazolyl)butyl]oxy-6-chloro-3-hydroxymethyl-1,2,3,5-tetrahydroimidazo[2,1-b]quinazolin-2-one.

53. The compound of claim 50 wherein Y is methoxy, namely 7-[4-(N-imidazolyl)butyl]oxy-6-methoxy-3-hydroxymethyl-1,2,3,5-tetrahydroimidazo[2,1-b]quinazolin-2-one.

54. The compound of claim 2 wherein n is 5 and $R_1$, $R_2$ and $R_4$ are hydrogen.

55. The compound of claim 54 wherein $R_3$ is hydrogen.

56. The compound of claim 55 wherein Y is hydrogen, namely 7-[5-(N-imidazolyl)pentyl]oxy-1,2,3,5-tetrahydroimidazo[2,1-b]quinazolin-2-one.

57. The compound of claim 55 wherein Y is chloro, namely 7-[5-(N-imidazolyl)pentyl]oxy-6-chloro-1,2,3,5-tetrahydroimidazo[2,1-b]quinazolin-2-one.

58. The compound of claim 55 wherein Y is methoxy, namely 7-[5-(N-imidazolyl)pentyl]oxy-6-methoxy-1,2,3,5-tetrahydroimidazo[2,1-b]quinazolin-2-one.

59. The compound of claim 54 wherein $R_3$ is methyl.

60. The compound of claim 59 wherein Y is hydrogen, namely 7-[5-(N-imidazolyl)pentyl]oxy-3-methyl-1,2,3,5-tetrahydroimidazo[2,1-b]quinazolin-2-one.

61. The compound of claim 59 wherein Y is chloro, namely 7-[5-(N-imidazolyl)pentyl]oxy-6-chloro-3-methyl-1,2,3,5-tetrahydroimidazo[2,1-b]quinazolin-2-one.

62. The compound of claim 59 wherein Y is methoxy, namely 7-[5-(N-imidazolyl)pentyl]oxy-6-methoxy-3- methyl-1,2,3,5-tetrahydroimidazo[2,1-b]quinazolin-2-one.

63. The compound of claim 54 wherein $R_3$ is ethyl.

64. The compound of claim 63 wherein Y is hydrogen, namely 7-[5-(N-imidazolyl)pentyl]oxy-3-ethyl-1,2,3,5-tetrahydroimidazo[2,1-b]quinazolin-2-one.

65. The compound of claim 63 wherein Y is chloro, namely 7-[5-(N-imidazolyl)pentyl]oxy-6-chloro-3-ethyl-1,2,3,5-tetrahydroimidazo[2,1-b]quinazolin-2-one.

66. The compound of claim 63 wherein Y is methoxy, namely 7-[5-(N-imidazolyl)pentyl]oxy-6-methoxy-3-methyl-1,2,3,5-tetrahydroimidazo[2,1-b]quinazolin-2-one.

67. The compound of claim 54 wherein $R_3$ is hydroxymethyl.

68. The compound of claim 67 wherein Y is hydrogen, namely 7-[5-(N-imidazolyl)pentyl]oxy-3-hydroxymethyl-1,2,3,5-tetrahydroimidazo[2,1-b]quinazolin-2-one.

69. The compound of claim 67 wherein Y is chloro, namely 7-[5-(N-imidazolyl)pentyl]oxy-6-chloro-3-hydroxymethyl-1,2,3,5-tetrahydroimidazo[2,1-b]quinazolin-2-one.

70. The compound of claim 67 wherein Y is methoxy, namely 7-[5-(N-imidazolyl)pentyl]oxy-6-methoxy-3-hydroxy-methyl-1,2,3,5-tetrahydroimidazo[2,1-b]quinazolin-2-one.

71. The compound of claim 2 wherein n is 6 and $R_1$, $R_2$ and $R_4$ are hydrogen.

72. The compound of claim 71 wherein $R_3$ is hydrogen.

73. The compound of claim 72 wherein Y is hydrogen, namely 7-[6-(N-imidazolyl)hexyl]oxy-1,2,3,5-tetrahydroimidazo[2,1-b]quinazolin-2-one.

74. The compound of claim 72 wherein Y is chloro, namely 7-[6-(N-imidazolyl)hexyl]oxy-6-chloro-1,2,3,5-tetrahydroimidazo[2,1-b]quinazolin-2-one.

75. The compound of claim 72 wherein Y is methoxy, namely 7-[6-(N-imidazolyl)hexyl]oxy-6-methoxy-1,2,3,5-tetrahydroimidazo[2,1-b]quinazolin-2-one.

76. The compound of claim 71 wherein $R_3$ is methyl.

77. The compound of claim 76 wherein Y is hydrogen, namely 7-[6-(N-imidazolyl)hexyl]oxy-3-methyl-1,2,3,5-tetrahydroimidazo[2,1-b]quinazolin-2-one.

78. The compound of claim 76 wherein Y is chloro, namely 7-[6-(N-imidazolyl)hexyl]oxy-6-chloro-3-methyl-1,2,3,5-tetrahydroimidazo[2,1-b]quinazolin-2-one.

79. The compound of claim 76 wherein Y is methoxy, namely 7-[6-(N-imidazolyl)hexyl]oxy-6-methoxy-3-methyl-1,2,3,5-tetrahydroimidazo[2,1-b]quinazolin-2-one.

80. The compound of claim 71 wherein $R_3$ is ethyl.

81. The compound of claim 80 wherein Y is hydrogen, namely 7-[6-(N-imidazolyl)hexyl]oxy-3-ethyl-1,2,3,5-tetrahydroimidazo[2,1-b]quinazolin-2-one.

82. The compound of claim 80 wherein Y is chloro, namely 7-[6-(N-imidazolyl)hexyl]oxy-6-chloro-3-ethyl-1,2,3,5-tetrahydroimidazo[2,1-b]quinazolin-2-one.

83. The compound of claim 80 wherein Y is methoxy, namely 7-[6-(N-imidazolyl)hexyl]oxy-6-methoxy-3-methyl-1,2,3,5-tetrahydroimidazo[2,1-b]quinazolin-2-one.

84. The compound of claim 71 wherein $R_3$ is hydroxymethyl.

85. The compound of claim 84 wherein Y is hydrogen, namely 7-[6-(N-imidazolyl)hexyl]oxy-3-hydroxymethyl-1,2,3,5-tetrahydroimidazo[2,1-b]quinazolin-2-one.

86. The compound of claim 84 wherein Y is chloro, namely 7-[6-(N-imidazolyl)hexyl]oxy-6-chloro-3-hydroxymethyl-1,2,3,5-tetrahydroimidazo[2,1-b]quinazolin-2-one.

87. The compound of claim 84 wherein Y is methoxy, namely 7-[6-(N-imidazolyl)hexyl]oxy-6-methoxy-3-hydroxy-methyl-1,2,3,5-tetrahydroimidazo[2,1-b]quinazolin-2-one.

88. The compound of claim 2 wherein n is 1 and $R_1$, $R_2$ and $R_4$ are hydrogen.

89. The compound of claim 88 wherein $R_3$ is hydrogen.

90. The compound of claim 89 wherein Y is hydrogen, namely 7-[1-(N-imidazolyl)methyl]oxy-1,2,3,5-tetrahydroimidazo[2,1-b]quinazolin-2-one.

91. The compound of claim 89 wherein Y is chloro, namely 7-[1-(N-imidazolyl)methyl]oxy-6-chloro-1,2,3,5-tetrahydroimidazo[2,1-b]quinazolin-2-one.

92. The compound of claim 89 wherein Y is methoxy, namely 7-[1-(N-imidazolyl)methyl]oxy-6-methoxy-1,2,3,5-tetrahydroimidazo[2,1-b]quinazolin-2-one.

93. The compound of claim 88 wherein $R_3$ is methyl.

94. The compound of claim 93 wherein Y is hydrogen, namely 7-[1-(N-imidazolyl)methyl]oxy-3-methyl-1,2,3,5-tetrahydroimidazo[2,1-b]quinazolin-2-one.

95. The compound of claim 93 wherein Y is chloro, namely 7-[1-(N-imidazolyl)methyl]oxy-6-chloro-3-methyl-1,2,3,5-tetrahydroimidazo[2,1-b]quinazolin-2-one.

96. The compound of claim 93 wherein Y is methoxy, namely 7-[1-(N-imidazolyl)methyl]oxy-6-methoxy-3-methyl-1,2,3,5-tetrahydroimidazo[2,1-b]quinazolin-2-one.

97. The compound of claim 88 wherein $R_3$ is ethyl.

98. The compound of claim 97 wherein Y is hydrogen, namely 7-[1-(N-imidazolyl)methyl]oxy-3-ethyl-1,2,3,5-tetrahydroimidazo[2,1-b]quinazolin-2-one.

99. The compound of claim 97 wherein Y is chloro, namely 7-[1-(N-imidazolyl)methyl]oxy-6-chloro-3-ethyl-1,2,3,5-tetrahydroimidazo[2,1-b]quinazolin-2-one.

100. The compound of claim 97 wherein Y is methoxy, namely 7-[1-(N-imidazolyl)methyl]oxy-6-methoxy-3-methyl-1,2,3,5-tetrahydroimidazo[2,1-b]quinazolin-2-one.

101. The compound of claim 88 wherein $R_3$ is hydroxymethyl.

102. The compound of claim 101 wherein Y is hydrogen, namely 7-[1-(N-imidazolyl)methyl]oxy-3-hydroxymethyl-1,2,3,5-tetrahydroimidazo[2,1-b]quinazolin-2-one.

103. The compound of claim 101 wherein Y is chloro, namely 7-[1-(N-imidazolyl)methyl]oxy-6-chloro-3-hydroxy-methyl-1,2,3,5-tetrahydroimidazo[2,1-b]quinazolin-2-one.

104. The compound of claim 101 wherein Y is methoxy, namely 7-[1-(N-imidazolyl)methyl]oxy-6-methoxy-3-hydroxy-methyl-1,2,3,5-tetrahydroimidazo[2,1-b]quinazolin-2-one.

105. The compound of claim 2 wherein n is 7 and $R_1$, $R_2$ and $R_4$ are hydrogen.

106. The compound of claim 105 wherein $R_3$ is hydrogen.

107. The compound of claim 106 wherein Y is hydrogen, namely 7-[7-(N-imidazolyl)heptyl]oxy-1,2,3,5-tetrahydroimidazo[2,1-b]quinazolin-2-one.

108. The compound of claim 106 wherein Y is chloro, namely 7-[7-(N-imidazolyl)heptyl]oxy-6-chloro-1,2,3,5-tetrahydroimidazo[2,1-b]quinazolin-2-one.

109. The compound of claim 106 wherein Y is methoxy, namely 7-[7-(N-imidazolyl)heptyl]oxy-6-methoxy-1,2,3,5-tetrahydroimidazo[2,1-b]quinazolin-2-one.

110. The compound of claim 105 wherein $R_3$ is methyl.

111. The compound of claim 110 wherein Y is hydrogen, namely 7-[7-(N-imidazolyl)heptyl]oxy-3-methyl-1,2,3,5-tetrahydroimidazo[2,1-b]quinazolin-2-one.

112. The compound of claim 110 wherein Y is chloro, namely 7-[7-(N-imidazolyl)heptyl]oxy-6-chloro-3-methyl-1,2,3,5-tetrahydroimidazo[2,1-b]quinazolin-2-one.

113. The compound of claim 110 wherein Y is methoxy, namely 7-[7-(N-imidazolyl)heptyl]oxy-6-methoxy-3-methyl-1,2,3,5-tetrahydroimidazo[2,1-b]quinazolin-2-one.

114. The compound of claim 105 wherein $R_3$ is ethyl.

115. The compound of claim 114 wherein Y is hydrogen, namely 7-[7-(N-imidazolyl)heptyl]oxy-3-ethyl-1,2,3,5-tetrahydroimidazo[2,1-b]quinazolin-2-one.

116. The compound of claim 114 wherein Y is chloro, namely 7-[7-(N-imidazolyl)heptyl]oxy-6-chloro-3-ethyl-1,2,3,5-tetrahydroimidazo[2,1-b]quinazolin-2-one.

117. The compound of claim 114 wherein Y is methoxy, namely 7-[7-(N-imidazolyl)heptyl]oxy-6-methoxy-3-methyl-1,2,3,5-tetrahydroimidazo[2,1-b]quinazolin-2-one.

118. The compound of claim 105 wherein $R_3$ is hydroxymethyl.

119. The compound of claim 118 wherein Y is hydrogen, namely 7-[7-(N-imidazolyl)heptyl]oxy-3-hydroxymethyl-1,2,3,5-tetrahydroimidazo[2,1-b]quinazolin-2-one.

120. The compound of claim 118 wherein Y is chloro, namely 7-[7-(N-imidazolyl)heptyl]oxy-6-chloro-3-hydroxy-methyl-1,2,3,5-tetrahydroimidazo[2,1-b]quinazolin-2-one.

121. The compound of claim 118 wherein Y is methoxy, namely 7-[7-(N-imidazolyl)heptyl]oxy-6-methoxy-3-hydroxy-methyl-1,2,3,5-tetrahydroimidazo[2,1-b]quinazolin-2-one.

122. The compound of claim 2 wherein n is 8 and $R_1$, $R_2$ and $R_4$ are hydrogen.

123. The compound of claim 122 wherein $R_3$ is hydrogen.

124. The compound of claim 123 wherein Y is hydrogen, namely 7-[8-(N-imidazolyl)octyl]oxy-1,2,3,5-tetrahydroimidazo[2,1-b]quinazolin-2-one.

125. The compound of claim 123 wherein Y is chloro, namely 7-[8-(N-imidazolyl)octyl]oxy-6-chloro-1,2,3,5-tetrahydroimidazo[2,1-b]quinazolin-2-one.

126. The compound of claim 123 wherein Y is methoxy, namely 7-[8-(N-imidazolyl)octyl]oxy-6-methoxy-1,2,3,5-tetrahydroimidazo[2,1-b]quinazolin-2-one.

127. The compound of claim 122 wherein $R_3$ is methyl.

128. The compound of claim 127 wherein Y is hydrogen, namely 7-[8-(N-imidazolyl)octyl]oxy-3-methyl-1,2,3,5-tetrahydroimidazo[2,1-b]quinazolin-2-one.

129. The compound of claim 127 wherein Y is chloro, namely 7-[8-(N-imidazolyl)octyl]oxy-6-chloro-3-methyl-1,2,3,5-tetrahydroimidazo[2,1-b]quinazolin-2-one.

130. The compound of claim 127 wherein Y is methoxy, namely 7-[8-(N-imidazolyl)octyl]oxy-6-methoxy-3-methyl-1,2,3,5-tetrahydroimidazo[2,1-b]equianzolin-2-one.

131. The compound of claim 122 wherein $R_3$ is ethyl.

132. The compound of claim 131 wherein Y is hydrogen, namely 7-[8-(N-imidazolyl)octyl]oxy-3-ethyl-1,2,3,5-tetrahydroimidazo[2,1-b]quinazolin-2-one.

133. The compound of claim 131 wherein Y is chloro, namely 7-[8-(N-imidazolyl)octyl]oxy-6-chloro-3-ethyl-1,2,3,5-tetrahydroimidazo[2,1-b]quinazolin-2-one.

134. The compound of claim 131 wherein Y is methoxy, namely 7-[8-(N-imidazolyl)octyl]oxy-6-methoxy-3-methyl-1,2,3,5-tetrahydroimidazo[2,1-b]quinazolin-2-one.

135. The compound of claim 122 wherein $R_3$ is hydroxymethyl.

136. The compound of claim 135 wherein Y is hydrogen, namely 7-[8-(N-imidazolyl)octyl]oxy-3-hydroxymethyl-1,2,3,5-tetrahydroimidazo[2,1-b]quinazolin-2-one.

137. The compound of claim 135 wherein Y is chloro, namely 7-[8-(N-imidazolyl)octyl]oxy-6-chloro-3-hydroxy-methyl-1,2,3,5-tetrahydroimidazo[2,1-b]quinazolin-2-one.

138. The compound of claim 135 wherein Y is methoxy, namely 7-[8-(N-imidazolyl)octyl]oxy-6-methoxy-3-hydroxy-methyl-1,2,3,5-tetrahydroimidazo[2,1-b]quinazolin-2-one.

139. The compound of claim 1 wherein $R_1$, $R_2$, $R_3$, and $R_4$ are hydrogen, Y is hydrogen and n is an integer of 1–8 wherein the imidazolylalkyloxy is attached to the 1,2,3,5-tetrahydroimidazo[2,1-b]quinazolin-2-one at the position 6, 8 or 9.

140. The compound of claim 1 wherein $R_1$, $R_2$, $R_3$, and $R_4$ are hydrogen, Y is chloro and n is an integer of 1–8 and wherein the imidazolylalkyloxy is attached to the 1,2,3,5-tetrahydroimidazo[2,1-b]quinazolin-2-one at the position 6, 8 or 9.

141. The compound of claim 1 wherein $R_1$, $R_2$, $R_3$, and $R_4$ are hydrogen, Y is methoxy and n is an integer of 1–8 and wherein the imidazolylalkyloxy is attached to the 1,2,3,5-tetrahydroimidazo[2,1-b]quinazolin-2-one at the position 6, 8 or 9.

142. The compound of claim 1 wherein $R_1$, $R_2$, $R_3$, and $R_4$ are hydrogen, n is an integer of 1–8 and wherein the imidazolylalkyloxy is attached to the 1,2,3,5-tetrahydroimidazo[2,1-b]quinazolin-2-one at the position 6, 7, 8 or 9.

143. The compound of claim 1 wherein $R_1$, $R_2$, $R_4$ and Y are hydrogen, n is an integer of 1–8 and wherein the imidazolylalkyloxy is attached to the 1,2,3,5-tetrahydroimidazo[2,1-b]quinazolin-2-one at the position 6, 7, 8 or 9.

144. A method for inhibiting 3′,5′-cyclic AMP phosphodiesterase which method comprises administering a cyclic AMP phosphodiesterase inhibiting amount of a compound of the formula

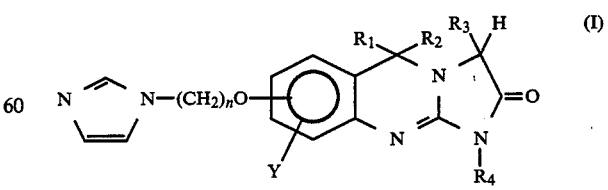

wherein:
n is an integer of 1 to 8;
$R_1$ is hydrogen or alkyl of 1–6 carbons;
$R_2$ is hydrogen;

$R_3$ is hydrogen, alkyl of 1-6 carbons, phenyl, benzyl, hydroxy lower alkyl, carbamoylalkyl, carboxyalkyl, alkoxycarbonylalkyl;

$R_4$ is hydrogen, alkyl of 1-6 carbons, benzyl, or hydroxy lower alkyl;

Y is hydrogen, alkyl of 1 to 4 carbon atoms, halo or lower alkoxy;

any of its optical isomers, the mixture thereof, or the pharmaceutically acceptable acid addition salt.

145. The method of claim 144 wherein the inhibition of said phosphodiesterase activity results in antithrombotic activity.

146. A method for treating heart failure which method comprises administering to a subject in need of such treatment a therapeutically effective amount of a compound of the formula

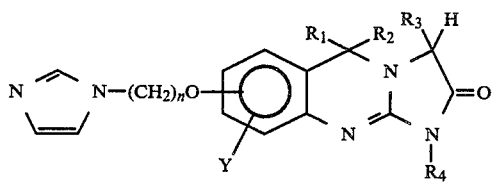

wherein:
n is an integer of 1 to 8;
$R_1$ is hydrogen or alkyl of 1-6 carbons;
$R_2$ is hydrogen;
$R_3$ is hydrogen, alkyl of 1-6 carbons, phenyl, benzyl, hydroxy lower alkyl, carbamoylalkyl, carboxyalkyl, alkoxycarbonylalkyl;
$R_4$ is hydrogen, alkyl of 1-6 carbons, benzyl, or hydroxy lower alkyl;
Y is hydrogen, alkyl of 1 to 4 carbon atoms, halo or lower alkoxy;
any of its optical isomers, the mixture thereof, or the pharmaceutically acceptable acid addition salt.

147. A method for treating hypertension which method comprises administering to a subject in need of such treatment a therapeutically effective amount of a compound of the formula

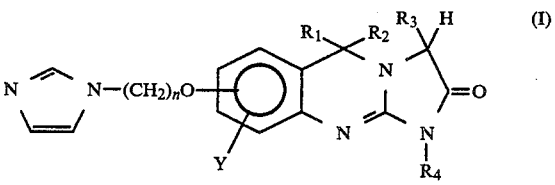

wherein:
n is an integer of 1 to 8;
$R_1$ is hydrogen or alkyl of 1-6 carbons;
$R_2$ is hydrogen;
$R_3$ is hydrogen, alkyl of 1-6 carbons, phenyl, benzyl, hydroxy lower alkyl, carbamoylalkyl, carboxyalkyl, alkoxycarbonylalkyl;
$R_4$ is hydrogen, alkyl of 1-6 carbons, benzyl, or hydroxy lower alkyl;
Y is hydrogen, alkyl of 1 to 4 carbon atoms, halo or lower alkoxy;
any of its optical isomers, the mixture thereof, or the pharmaceutically acceptable acid addition salt.

* * * * *